(12) United States Patent
Mittmann et al.

(10) Patent No.: US 7,157,564 B1
(45) Date of Patent: Jan. 2, 2007

(54) TAG NUCLEIC ACIDS AND PROBE ARRAYS

(75) Inventors: Michael Mittmann, Palo Alto, CA (US); MacDonald Morris, Felton, CA (US); Thomas B. Ryder, Los Gatos, CA (US); David Lockhart, Del Mar, CA (US)

(73) Assignee: Affymetrix, Inc., Santa Clara, CA (US)

( * ) Notice: Subject to any disclaimer, the term of this patent is extended or adjusted under 35 U.S.C. 154(b) by 865 days.

(21) Appl. No.: 09/827,383

(22) Filed: Apr. 4, 2001

Related U.S. Application Data

(60) Provisional application No. 60/195,585, filed on Apr. 6, 2000.

(51) Int. Cl.
C07H 21/02 (2006.01)

(52) U.S. Cl. .................................................... 536/23.1

(58) Field of Classification Search ................ 536/23.1, 536/24.3, 24.31, 24.33; 435/6, 810, 91.2
See application file for complete search history.

(56) References Cited

U.S. PATENT DOCUMENTS

| | | | |
|---|---|---|---|
| 4,359,353 A | 11/1982 | Kydd | |
| 4,441,943 A | 4/1984 | Kydd | |
| 5,143,854 A | 9/1992 | Pirrung et al. | |
| 5,149,625 A | 9/1992 | Church et al. | |
| 5,242,979 A | 9/1993 | Barnum et al. | |
| 5,252,743 A | 10/1993 | Barrett et al. | |
| 5,324,663 A | 6/1994 | Lowe | |
| 5,384,261 A | 1/1995 | Winkler et al. | |
| 5,405,783 A | 4/1995 | Pirrung et al. | |
| 5,412,087 A | 5/1995 | McGall et al. | |
| 5,424,186 A | 6/1995 | Fodor et al. | |
| 5,445,934 A | 8/1995 | Fodor et al. | |
| 5,451,505 A | 9/1995 | Dollinger | |
| 5,451,683 A | 9/1995 | Barrett et al. | |
| 5,482,867 A | 1/1996 | Barrett et al. | |
| 5,489,678 A | 2/1996 | Fodor et al. | |
| 5,491,074 A | 2/1996 | Aldwin et al. | |
| 5,510,270 A | 4/1996 | Fodor et al. | |
| 5,527,681 A | 6/1996 | Holmes | |
| 5,550,215 A | 8/1996 | Holmes | |
| 5,571,639 A | 11/1996 | Hubbell et al. | |
| 5,593,839 A | 1/1997 | Hubbell et al. | |
| 5,599,695 A | 2/1997 | Pease et al. | |
| 5,604,097 A | 2/1997 | Brenner | |
| 5,624,711 A | 4/1997 | Sundberg et al. | |
| 5,631,734 A | 5/1997 | Stern et al. | |
| 5,635,400 A | 6/1997 | Brenner | |
| 5,654,413 A | 8/1997 | Brenner | |
| 5,677,195 A | 10/1997 | Winkler et al. | |
| 5,744,101 A | 4/1998 | Fodor et al. | |
| 5,744,305 A | 4/1998 | Fodor et al. | |
| 5,744,992 A | 4/1998 | Baumann | |
| 5,753,788 A | 5/1998 | Fodor et al. | |
| 5,770,456 A | 6/1998 | Holmes | |
| 5,800,992 A | 9/1998 | Fodor et al. | |
| 5,807,683 A | 9/1998 | Brenner | |
| 5,831,070 A | 11/1998 | Pease et al. | |
| 5,846,719 A | 12/1998 | Brenner | |
| 5,856,011 A | 1/1999 | Sogabe | |
| 5,856,092 A | 1/1999 | Dale | |
| 5,863,722 A | 1/1999 | Brenner | |
| 5,981,176 A | 11/1999 | Wallace | |
| 6,013,431 A | 1/2000 | Soderlund | |
| 6,013,445 A | 1/2000 | Albrecht | |
| 6,040,138 A | 3/2000 | Lockhart et al. | |
| 6,040,193 A | 3/2000 | Winkler et al. | |
| 6,103,463 A | 8/2000 | Chetverin | |
| 6,150,516 A | 11/2000 | Brenner | |
| 6,156,502 A | 12/2000 | Beattie | |
| 6,269,846 B1 | 8/2001 | Montagu | |
| 6,440,667 B1 | 8/2002 | Fodor | |
| 6,458,630 B1 | 10/2002 | Davis et al. | |
| 6,607,878 B1 | 8/2003 | Sorge | |
| 6,627,402 B1 | 9/2003 | Wallace | |

FOREIGN PATENT DOCUMENTS

| | | |
|---|---|---|
| WO | WO US99/00730 | 1/1999 |
| WO | WO 99/00730 | 7/1999 |
| WO | WO 00/58516 | 5/2000 |

OTHER PUBLICATIONS

Dujon et al, "The yeast genome groject: what did we learn?" Trends in Genetics, (1996) 12(7):263-270.*

Lipshutz RJ: Letter from Dr. Lipshutz to Dr. Carrano, Aug. 22, 1994. *Link*.

AFFYMETRIX: GeneChip® Assays and Controls Price List, Nov. 1997. *Link*.

AFFYMETRIX: GeneChip® Arrays and Assays Product List, Jan. 1998. *Link*.

AFFYMETRIX: GeneChip® Arrays and Assays Product List, Nov. 1998. *Link*.

AFFYMETRIX: GeneChip® Arrays and Reagents, Feb. 1999. *Link*.

(Continued)

*Primary Examiner*—Jeffrey Fredman
(74) *Attorney, Agent, or Firm*—Sandra E. Wells

(57) ABSTRACT

The invention provides a unique set of nucleic acid sequences which is appropriate for use for a wide variety of applications requiring nucleic acid tags. As such, the sequence tags of the presently claimed invention may be used, for example, to label biological and nonbiological materials, in genotyping applications and in a variety of other analyses.

8 Claims, 7 Drawing Sheets

OTHER PUBLICATIONS

AFFYMETRIX: GeneChip® Price Catalog (U.S. and Canada), Jul. 1999. Link.
AFFYMETRIX: Addendum (U.S. and Canada) GeneChip® Arrays and Reagents, Aug. 1999. Link.
AFFYMETRIX: GeneChip® Price Catalog (U.S. and Canada), Jan. 2000. Link.
AFFYMETRIX: Affymetrix® Catalog Addendum GeneChip® Arrays and Reagents (U.S. and Canada), Feb. 2000. Link.
AFFYMETRIX: Affymetrix® Product Catalog (Global), Aug. 2000. Link.
AFFYMETRIX: Affymetrix® Product Catalog (Global), Jan. 2001. Link.
AFFYMETRIX: Affymetrix® Product Catalog (Global), Jan. 2002. Link.
AFFYMETRIX: Affymetrix® Product Catalog (Global), Jul. 2002. Link.
AFFYMETRIX: Product Information GeneChip® HuSNP Mapping Assay, 1999. Link.
AFFYMETRIX: Product Information GeneChip® GenFlex™ Tag Array, 2000. Link.
AFFYMETRIX: Product Information GeneChip® Yeast Genome S98 Array, 2000. Link.
AFFYMETRIX: Product Information GeneChip® HIV PRT Assay, 1997. Link.
AFFYMETRIX: Product Information GeneChip® HIV PRT Plus, 1998. Link.
AFFYMETRIX: Product Information GeneChip® p53 Assay, 1997. Link.
AFFYMETRIX: Product Information GeneChip® p53 Probe Array and Reagents, 1998. Link.
AFFYMETRIX: Product Information GeneChip® CYP450 Assay, 1997. Link.
AFFYMETRIX: Product Information GeneChip® CYP450 Probe Array and Reagents, 1998. Link.
AFFYMETRIX: Product Information GeneChip® Hu6800 Array, 1998. Link.
AFFYMETRIX: Product Information Human Genome U95 Set, 2000. Link.
AFFYMETRIX: Product Information GeneChip® Human Genome U133 Set, 2001. Link.
AFFYMETRIX: Product Information GeneChip® Human Genome Focus Array, 2002. Link.
AFFYMETRIX: Product Information GeneChip® Human Cancer G110 Array, 1999. Link.
AFFYMETRIX: Product Information Rat Neurobiology U34 Array, 2000. Link.
AFFYMETRIX: Product Information GeneChip® Rat Genome U34 Array Set, 1999. Link.
AFFYMETRIX: Product Information GeneChip® Test1, 1998. Link.
AFFYMETRIX: Product Information GeneChip® Test2 Array, 1999. Link.
AFFYMETRIX: Product Information GeneChip® Test3 Array, 2001. Link.
AFFYMETRIX: Product Information GeneChip® Yeast Genome S98 Array, 1999. Link.
AFFYMETRIX: Product Information GeneChip® Mu6500 Set, 1998. Link.
AFFYMETRIX: Product Information GeneChip® Murine Genome U74 Set, 2001. Link.
AFFYMETRIX: Product Information GeneChip® Murine 11K Set, 1998. Link.
AFFYMETRIX: Product Information GeneChip® Murine 11K Set, 2001. Link.
AFFYMETRIX: Product Information GeneChip® Murine 19K Set, 1998. Link.
AFFYMETRIX: Product Information Arabidopsis Genome Array, 2000. Link.
AFFYMETRIX: Product Information GeneChip® Arabidopsis ATH1 Genome Array, 2002. Link.
AFFYMETRIX: Product Information E. coli Genome Array, 2000. Link.
AFFYMETRIX: Product Information GeneChip® E. coli Antisense Genome Array, 2001. Link.
AFFYMETRIX: Product Information GeneChip® P. aeruginosa Genome Array, 2001. Link.
AFFYMETRIX: Product Information P. aeruginosa Genome Array, 2001. Link.
AFFYMETRIX: Product Information Drosophila Genome Array, 2000. Link.
AFFYMETRIX: Product Information GeneChip® B. subtilis Genome Array, 2002. Link.
AFFYMETRIX: Product Information GeneChip® C. elegans Genome Array, 2002. Link.
AFFYMETRIX: Product Information GeneChip® Custom Arrays, 1998. Link.
AFFYMETRIX: Product Information GeneChip® Custom Arrays, 2002. Link.
AFFYMETRIX: Product Information Genehip® Ye6100 Set, 1998. Link.
AFFYMETRIX: Product Information GeneChip® Human 35K Set, 1998. Link.
Cronin MT, et al. "*Cystic fibrosis* mutation detection by hybridization to light-generated DNA probe arrays", Human Mutation, 1996, 7, 3, 244-55, Link.
Hacia JG, et al, "Detection of heterozygous mutations in BRCA1 using high density oligonucleotide arrays and two-colour fluorescence analysis", Nature Genetics, 1996, 14, 4, 441-7. Link.
Kozal MJ, et al. "Extensive polymorphisms observed in HIV-1 clade B protease gene using high-density oligonucleotide arrays", Nature Medicine, 1996, 2, 7, 753-9. Link.
Lockhart DJ, et al, "Expression monitoring by hybridization to high-density oligonucleotide arrays", Nature Biotechnology, 1996, 14, 13, 1675-80. Link.
Shoemaker DD, et al, "Quantitative phenotypic analysis of yeast deletion mutants using a highly parallel molecular bar-coding strategy", Nature Genetics, 1996, 14, 4, 450-6. Link.
Wodicka L, et al, "Genome-wide expression monitoring in *Saccharomyces cerevisiae*", Nature Biotechnology, 1997, 15, 13, 1359-67. Link.
De Saizieu A, et al, "Bacterial transcript Imaging by hybridization of total RNA to oligonucleotide arrays", Nature Biotechnology, 1998, 16, 1, 45-8. Link.
Fan JB, et al, "Parallel genotyping of human SNPs using generic high-density oligonucleotide tag arrays", Genome Research, 2000, 10, 6, 853-60. Link.
Harmer SL, et al, "Orchestrated transcription of key pathways in Arabidopsis by the circadian clock", Science, 2000, 290, 5499, 2110-3. Link.
Rieneck K, et al, "Massive parallel gene expression profiling of RINm5F pancreatic islet beta-cells stimulated with interleukin-1beta", Apmis, 2000, 108, 12, 855-72. Link.
Rudd KE, "New tools for an old workhorse", Nature Biotechnology, 2000, 18, 12, 1241-2. Link.
Selinger DW, et al, "RNA expression analysis using a 30 base pair resolution *Escherichia coli* genome array", Nature Biotechnology, 2000, 18, 12, 1262-8. Link.
Travers KJ, et al, "Functional and genomic analyses reveal an essential coordination between the unfolded protein response and ER-associated degradation", Cell, 2000, 101, 3, 249-58. Link.
Hakak Y, et al, "Genome-wide expression analysis reveals dysregulation of myelination-related genes in chronic schizophrenia", Proceedings of the National Academy of Sciences, USA, 2001, 98, 8, 4746-51. Link.
Lu SC, et al, "Methionine adenosyltransferase 1A knockout mice are predisposed to liver injury and exhibit increased expression of genes involved in proliferation", Proceedings of the National Academy of Sciences, USA, 2001, 98, 10, 5560-5. Link.
MacDonald TJ, et al, "Expression profiling of medulloblastoma: PDGFRA and the RAS/MAPK pathway as therapeutic targets for metastatic disease", Nature Genetics, 2001, 29, 2, 143-52. Link.

Niculescu AB, 3rd, et al, "The human genome: genetic testing and animal models", American Journal of Psychiatry, 2001, 158, 10, 1587. *Link.*

Stamey TA, et al, "Molecular genetic profiling of Gleason grade 4/5 prostate cancers compared to benign prostatic hyperplasia", Journal of Urology, 2001, 166, 6, 2171-7. *Link.*

Welsh JB, et al, "Analysis of gene expression profiles in normal and neoplastic ovarian tissue samples identifies candidate molecular markers of epithelial ovarian cancer", Proceedings of the National Academy of Sciences, USA, 2001, 98, 3, 1176-81. *Link.*

Chee M, et al, "Accessing genetic information with high-density DNA arrays", Science, 1996, 274, 5287, 610-4. *Link.*

Cho RJ, et al, "Parallel analysis of genetic selections using whole genome oligonucleotide arrays", Proceedings of the National Academy of Sciences of the United States of America, 1998, 95, 7, 3752-7. *Link.*

Bakay, et al, "Sources of variability and effect of experimental approach on expression profiling data interpretation", 2002, 3:4. *Link.*

Carmel, et al, "Gene expression profiling of acute spinal cord injury reveals spreading inflammatory signals and neuron loss", Pyhysiol Genomics 2001, 7:201-213. *Link.*

Affymetrix, Inc. Securities and Exchange Commission Filing S-3 filed on Oct. 17, 1997, also available at http://www.sec.gov/Archives/edgar/data/913077/0001047469-97-001100.txt. *Link.*

U.S. Appl. No. 09/079,324, Overbeck et al.

U.S. Appl. No. 09/122,216, Montagu.

U.S. Appl. No. 60/176,520, Balaban et al.

U.S. Appl. No. 08/626,285, Davis et al.

U.S. Appl. No. 60/140,359, Fan et al.

Dollinger, The Polymerase Chain Reaction, 1994, 265-274, Mullis et al., editors (Birkhauser, Boston).

Alper, Science, 1994, 1399-1401, vol. 264.

Needels et al., PNAS, 1993, 10700-10704, vol. 90.

J. Sambrook et al., EDS., Molecular Cloning. A Laboratory Manual, Second Ed., 1989, Cold Spring Harbor Laboratory Press.

Berger and Kimmel, Guide to Molecular Cloning Techniques, Methods in Enzymology, 1987, Academic Press, Inc., San Diego, CA, vol. 152.

Young and Davis, Proc. Natl. Acad. Sci., p. 1194, 1983, U.S.A., vol. 80.

Brenner and Lerner, PNAS, 5281-5383, 1992, vol. 89.

Alper, Science, 1399-1401, 1994, vol. 264.

U.S. Appl. No. 09/079,324, filed May 14, 1998, Overback, et al.

U.S. Appl. No. 60/176,520, filed Jan. 13, 2000, Balaban et al.

U.S. Appl. No. 60/140,359, filed Jun. 23, 1999, Fan et al.

Alper, Science, 1984, 1399-1401, vol. 264.

Young and Davis, Proc. Natl. Acad, Sci., p. 1194, 1983, U.S.A., vol. 80.

\* cited by examiner

US 7,157,564 B1

TAG NUCLEIC ACIDS AND PROBE ARRAYS

PRIORITY CLAIM

This application claims priority of U.S. Provisional Application 60/195,585 filed Apr. 6, 2000 entitled "Tag Nucleic Acids and Probe Arrays", which is incorporated herein by reference for all purposes in its entirety.

FIELD OF THE INVENTION

This invention provides sets of nucleic acid tags, arrays of oligonucleotide probes, nucleic acid-tagged sets of recombinant cells and other compositions. The invention relates to the selection and interaction of nucleic acids, and nucleic acids immobilized to solid substrates, including related chemistry, biology, and medical diagnostic uses.

REFERENCE TO SEQUENCE LISTING

The sequenced listing submitted on compact disc is hereby incorporated by reference. The two identical compact discs (Copy 1 and Copy 2) contain a single file named: "seqlistv2.txt", created on Feb. 11, 2003 and containing 365 KB.

BACKGROUND OF THE INVENTION

The use of short nucleic acid sequences as "tags" to identify specific biological substances in a sample is known. For example, tags may be used as a method of or as labels for a wide variety of biological and nonbiological materials, see, for example, Dollinger, The Polymerase Chain Reaction pp. 265–274 Mullis et al., editors (Birkhauser, Boston, 1994) or as a method of screening complex chemical libraries. See, for example, Alper, Science, 264: 1399–1401 (1994); and Needels et al. PNAS 90, 10700–10704 (1993). See also U.S. Pat. Nos. 4,359,353, 4,441,943, 5,451,505 and 5,654,413.

There is great necessity for sets of tag sequences which are known to hybridize effectively to their complementary probe sequences with minimal cross-hybridization between the different tag sequences. The presently claimed invention provides sets of tag sequences, tag sequence kits, and methods of using tag sequences which fulfill these requirements.

SUMMARY OF THE INVENTION

The presently claimed invention provides 2050 unique sequences which have been specifically chosen according to strict criteria to produce sequences suitable for a wide variety of "tagging" applications. These sequences are provided as SEQ ID NOs 1–2050.

In one embodiment, some or all of SEQ ID Nos 1–2050 comprise tag sequences. In a further embodiment, some or all of SEQ ID Nos 1–2050 comprise tag-probe sequences. In a further embodiment, the tag-probe sequences are immobilized to a solid support.

The unique sequences of the presently claimed invention may be used alone or in combinations of 10 or more, 100 or more, 200 or more, 500 or more, 1000 or more, 1500 or more, or 2000 or more as nucleic acid tags and/or tag-probes.

DETAILED DESCRIPTION OF THE PREFERRED EMBODIMENTS

I. Definitions

Figure 1:
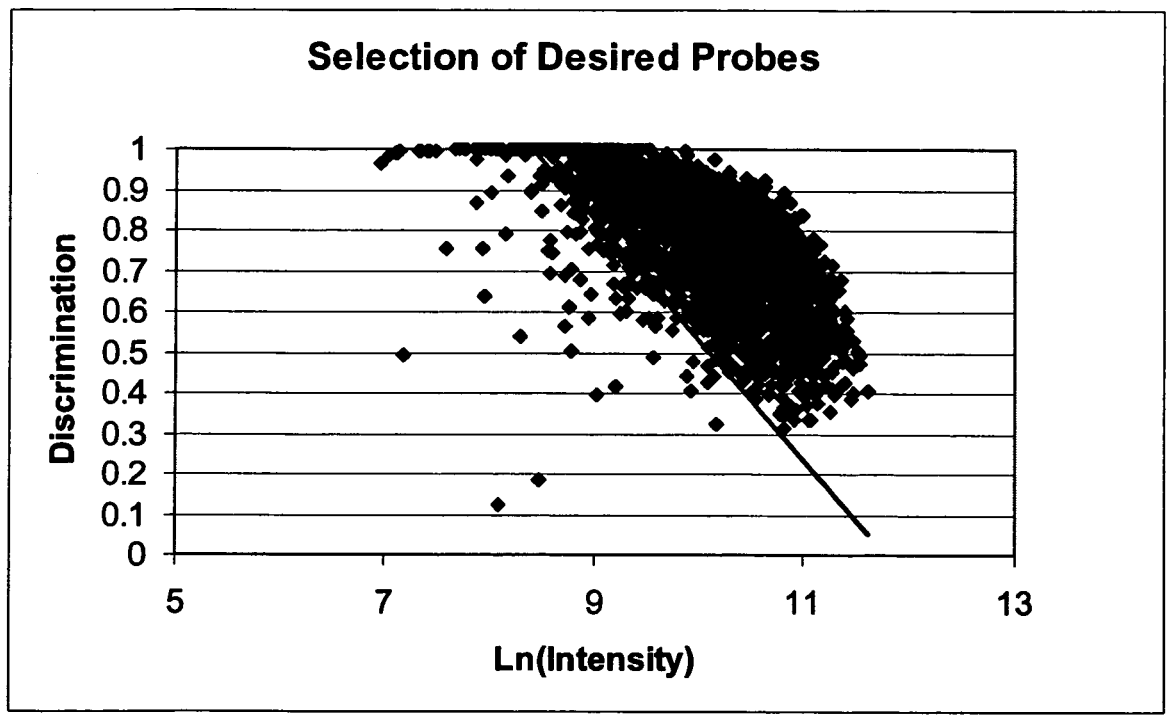
FIG. 1 shows a plot of the discrimination score and the signal intensity for 2200 candidate sequences.

As used herein, certain terms may have the following defined meanings.

As used in the specification and claims, the singular forms "a", "an" and "the" include plural references unless the context clearly dictates otherwise. For example, the term "an array" may include a plurality of arrays unless the context clearly dictates otherwise.

An "array" represents an intentionally created collection of molecules which can be prepared either synthetically or biosynthetically. In particular, the term "array" herein means an intentionally created collection of polynucleotides attached to at least a first surface of at least one solid support wherein the identity of each polynucleotide at a given predefined region is known. The terms "array," "biological chip" and "chip" are used interchangeably.

The array of molecules can be screened for biological activity in a variety of different formats (e.g., libraries of soluble molecules, libraries of compounds tethered to resin beads, fibers, silica chips, or other solid supports). The fabrication of polynucleotide arrays on a solid substrate, and methods of use of the arrays in different assays, are described in U.S. Pat. Nos. 5,143,854, 5,242,979, 5,252,743, 5,324,663, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,744,992, 5,753,788, 5,770,456, 5,831,070, 5,856,011, 6,040,138 and 6,040,193 all of which are incorporated by reference herein in their entireties for all purposes. See also, U.S. Ser. No. 09/079,324, U.S. Pat. No. 6,269,846, and PCT Application WO US99/00730 each of which is incorporated by reference herein in its entirety for all purposes. Preferred arrays contemplated by the presently claimed invention have the probe densities as described in the above referenced patents. For example, the '305 patent discloses 100, 400, 1,000 and 10,000 probes/cm$^2$.

"Solid support," "support," and "substrate" refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, fibers or other geometric configurations.

A "discrete, known location" refers to a localized area on a solid support which is, was, or is intended to be used for placement or fabrication of a selected molecule and is otherwise referred to herein in the alternative as a "selected" region. The discrete, known location may have any convenient shape, e.g., circular, rectangular, elliptical, wedge-shaped, etc. For the sake of brevity herein, "discrete, known locations" are sometimes referred to as "predefined regions," "regions," or "features." In some embodiments, a discrete, known location and, therefore, the area upon which each distinct compound is synthesized is smaller than about 1 cm$^2$ or even less than 1 mm$^2$. In additional embodiments, a discrete, known location can be achieved by physically separating the regions (i.e., beads, fibers, resins, gels, etc.) into wells, trays, etc.

As used herein, a "polynucleotide" is a sequence of two or more nucleotides. Polynucleotides of the present invention include sequences of deoxyribonucleic acid (DNA) or ribonucleic acid (RNA) which may be isolated from natural sources, recombinantly produced, or artificially synthesized. A further example of a polynucleotide of the present invention may be polyamide polynucleotide or peptide nucleic acid (PNA). This invention also encompasses situations in which there is nontraditional base pairing such as Hoogsteen base pairing which has been identified in certain tRNA molecules and postulated to exist in a triple helix. "Polynucleotide" is used interchangeably with "oligonucleotide" is this application.

The terms "nucleotide" and "nucleic acid base" include deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs may have one or more modified bases, as well as modified forms of ribose and phosphodiester moieties. The changes can be tailor made to stabilize or destabilize hybrid formation, enhance the specificity of hybridization with a complementary polynucleotide sequence as desired, or enhance stability of the polynucleotide.

The terms "nucleic acid," "nucleic acid molecule," or "nucleic acid sequence," refer to a deoxyribonucleotide or ribonucleotide polymer in either single-or double-stranded form, and unless otherwise limited, would encompass analogs of natural nucleotides that can function in a similar manner as naturally occurring nucleotides. Nucleic acids may be derived from a variety or sources including, but not limited to, naturally occurring nucleic acids, clones, synthesis in solution or solid phase synthesis.

As used herein a "probe" is defined as a nucleic acid capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

The term "target nucleic acid" or "target sequence" refers to a nucleic acid or nucleic acid sequence which is to be analyzed. A target can be a nucleic acid to which a probe will hybridize. The probe may or may not be specifically designed to hybridize to the target. It is either the presence or absence of the target nucleic acid that is to be detected, or the amount of the target nucleic acid that is to be quantified. The term target nucleic acid may refer to the specific subsequence of a larger nucleic acid to which the probe is directed or to the overall sequence (e.g., gene or mRNA) whose expression level it is desired to detect. The difference in usage will be apparent from context.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybrids can contain two DNA strands, two RNA strands, or one DNA and one RNA strand.

Methods for conducting polynucleotide hybridization assays have been well developed in the art. Hybridization assay procedures and conditions will vary depending on the application and are selected in accordance with the general binding methods known including those referred to in: Molecular Cloning, A Laboratory Manual, Second Ed., J. Sambrook et al., Eds., Cold Spring Harbor Laboratory Press, 1989 ("Sambrook et al."); Berger and Kimmel, "Methods in Enzymology," Vol. 152, "Guide to Molecular Cloning Techniques", Academic Press, Inc., San Diego, Calif., 1987; Young and Davis, *Proc. Natl. Acad. Sci., U.S.A.*, 80:1194 (1983), each of which are incorporated herein by reference.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

A nucleic acid "tag" is a selected nucleic acid with a specified nucleic acid sequence. A nucleic acid "probe" hybridizes to a nucleic acid "tag."

A nucleic acid "tag-probe" is a specific sequence capable of hybridizing to a specific "tag." Typically, the "tag-probe" is the complement or a partial complement of the "tag." In one typical configuration, nucleic acid tags are incorporated as labels into biological libraries, and the tag nucleic acids are detected using a microarray.

Throughout this disclosure, various aspects of this invention are presented in a range format. It should be understood that the description in range format is merely for convenience and brevity and should not be construed as an inflexible limitation on the scope of the invention.

Accordingly, the description of a range should be considered to have specifically disclosed all the possible subranges as well as individual numerical values within that range. For example, the description of a range such as 4 to 50 should be considered to have specifically disclosed all integers within the sub-ranges such as 4 to 10, 4 to 20, 4 to 30, 4 to 40, 4 to 50, 5 to 10, 5 to 20 etc., as well as individual numbers within that range, for example, 6, 8, 15, 20, 32, 39, 43, 48 etc. This applies regardless of the breadth of the range. Likewise, a description of a range such as 1 or more, 10 or more, $10^3$ or more, $10^6$ or more, or $10^{12}$ or more should be considered to have specifically disclosed individual numbers within that range as well as higher numbers, for example, 20, $2 \times 10^4$, $3 \times 10^8$, $4 \times 10^{15}$, $5 \times 10^{18}$, etc.

Various patents, patent applications and publications are referenced throughout the specification, unless otherwise indicated, each is incorporated by reference in its entirety for all purposes.

II. General

The presently claimed invention provides 2050 unique sequences which have been specifically chosen according to strict criteria to produce sequences suitable for a wide variety of "tagging" applications. These sequences are provided as SEQ ID NOs 1–2050.

In one embodiment, some or all of SEQ ID Nos 1–2050 comprise tag sequences. In a further embodiment, some or all of SEQ ID Nos 1–2050 comprise tag-probe sequences. In a further embodiment, the tag-probe sequences are immobilized to a solid support.

An initial set of 2200 20mer sequences was selected with closely matched melting temperatures. A further filter based on rules such as those described in U.S. Provisional Patent Application 60/176,520 was applied to optimized and standardize the hybridization characteristics of the set. Finally, sequences were removed if they were identical or nearly identical to each other or to sequences in the public databases. This reduced the pool of candidate sequences to 2200. The hybridization performance of the entire set of 2200 candidate sequences was evaluated. Labeled oligonucleotides complementary to the candidate sequences were synthesized and hybridized to an array containing probes designed to analyze the performance of all 2200 candidate sequences. The array contained four different sequences to interrogate each candidate sequence. A probe designed to be the perfect match complement to the candidate sequence (PM), a probe designed to have a central mismatch at position 10 (MM), and probes designed to be the complements to the PM and MM probes (cPM and cMM respectively).

FIG. 1 shows a plot of the discrimination score and the signal intensity for all 2200 sequences. A line was fitted to select the 2050 sequences with the highest discrimination and signal intensity. These 2050 sequences are SEQ ID Nos. 1–2050.

In one embodiment of the invention, the sequences of the presently claimed invention are tag-probes attached to a solid support. Methods of immobilizing presynthesized sequences and synthesizing sequences de novo on solid supports are known. See for example, U.S. Pat. Nos. 5,143,854, 5,242,979, 5,252,743, 5,324,663, 5,384,261, 5,405,783, 5,412,087, 5,424,186, 5,445,934, 5,451,683, 5,482,867, 5,489,678, 5,491,074, 5,510,270, 5,527,681, 5,550,215, 5,571,639, 5,593,839, 5,599,695, 5,624,711, 5,631,734, 5,677,195, 5,744,101, 5,744,305, 5,753,788, 5,770,456, 5,831,070,5,856,011, 5,744,992,6,040,138, 6,040,193, U.S. Ser. No. 09/079,324, U.S. Pat. No. 6,269,846, and PCT Application WO US99/00730.

In this and other embodiments it is often useful to provide control probes. As one example, SEQ ID Nos. 1–2000 may comprise the tag-probes and SEQ ID Nos. 2001–2050 may comprise the control probes. In a preferred embodiment, the control probes are representative of the population with respect to observed signal intensities and discrimination. In a further preferred embodiment, tag sequences with relatively low signals may be over-represented in the control sequences so as to increase information about the sensitivity of experiments at the lower limit of detection.

METHODS OF USE

The use of short nucleic acid sequences as "tags" to identify specific biological substances in a sample is known. For example, tags may be used as a method of or as labels for a wide variety of biological and nonbiological materials, see, for example, Dollinger, The Polymerase Chain Reaction pp. 265–274 Mullis et al., editors (Birkhauser, Boston, 1994) or as a method of screening complex chemical libraries. See, for example, Brenner and Lerner, PNAS 89, 5281–5383 (1992); Alper, Science, 264: 1399–1401 (1994); and Needels et al. PNAS 90, 10700–10704 (1993). See also U.S. Pat. Nos. 4,359,353, 4,441,943, 5,451,505, 5,149,625, 5,654,413 and 5,800,992.

In addition to those applications above, the presently claimed sequences are suitable to be employed for any of the methods described in U.S. Pat. No. 6,458,530 (filed Apr. 4, 1996), including as a method of analysis of genomic DNA. For example, as described in the 530 pagent, tag arrays may be used to identify the function of identified open reading frames (ORFs) by creating deletion mutants for each ORF and analyzing the resulting deletion mutants under a wide variety of selective conditions.

U.S. Provisional Patent Application No. 60/140,359 (filed Jun. 23, 1999) described methods of using tag arrays and the single base extension reaction for genotyping and other types of biological analysis. A set of tags and a tag array derived from Seq. ID Nos. 1–2000 and their complements are suitable to be used for the methods described in this application. Briefly, the '359 application describes methods of determining the genotype of an individual at a polymorphic locus or the frequency of alleles in a population. One embodiment of the method involves three step: (1) amplification of the polymorphic locus, (2) primer extension of a sequence-tagged primer with distinct labels for different polynucleotides at the polymorphic locus, and (3) hybridization to a tag array. The amount of each distinct label can be determined at known positions of the tag array. Each tag represents a distinct polymorphic locus and each distinct label represents a distinct allelic form at the polymorphic locus. The method permits the simultaneous determination of a genotype at multiple loci, as well as the determination of allele frequencies in a population. Another embodiment employs just steps (2) and (3).

Table 1, below, lists the sequences of the presently claimed invention. Column 1 lists the sequence ID number corresponding to each sequence. Column 2 lists the sequences in the 3' to 5' direction.

TABLE I

| Seq. Id | 3' to 5' sequence |
|---|---|
| 1 | TAAACTAGCATTGAGCCCAC |
| 2 | AAATCAGCAAACGGGCTCCG |
| 3 | GAATTGATAATCGCAGCCAC |
| 4 | GATATAGGAATGGCGCATAC |
| 5 | CTCATCGGAAGGGCTCGTAA |
| 6 | ACAGATGGAAAGGCAGTTCT |
| 7 | TTTGGTAGCTGAGTGCCCTA |
| 8 | TAACTGGTTTGACGCCACGC |
| 9 | TAATTGAGCTGACGGCGCAC |
| 10 | TTGTTGCTACTCTGGCCCGA |
| 11 | TTCCGTGCATAGTATAGGGA |
| 12 | TTATGCGACTTATCTCGGGA |
| 13 | TGTATAGGATTATGTCCGCG |
| 14 | CTGCTAGGAATATGAGCTAC |
| 15 | CTTCTGTCAATATGGGTACG |
| 16 | TATTTCGAGATATGAGGCGC |
| 17 | TTGATCGTAGATTCGTGAGC |
| 18 | CGAGATTACAATTCACGAGC |
| 19 | TGGTGTCTAGCTTCCAGCCT |
| 20 | TGAGGTCACGGTTCATGCTA |
| 21 | TGGTTACTGGTATATGCCGC |
| 22 | CCGAGTGCAGAATAAACCCG |
| 23 | GCGGTCTCAATACAAACTCA |
| 24 | GAAGCTACCATACGCGAGCA |
| 25 | ACGGGATAACAACGCAGCCT |
| 26 | AGAAGATCAACAGCTCGTCC |
| 27 | ATAAGATCAAGACCTGTGCC |
| 28 | ATTAGATTAAGACCAGCGCC |
| 29 | ATATAATCAAGACTGGCGCG |
| 30 | AGCATATAACCACTGATCCG |
| 31 | ACACTATTAAAGCTGCTCCG |
| 32 | CAATGTATAAGACTCTCGCC |
| 33 | CACTAATTCAGACGAAGCCG |
| 34 | GACCCTATCAGACAGATGCA |
| 35 | CACGCATCAAGACAGTATCG |
| 36 | CAGCTCCTAAGACTTGGACA |
| 37 | GGTATCATAGGACATTCGCA |
| 38 | GGTTACATGGATATAGCACC |
| 39 | TGTGTTTCAGCTATGCAGGC |
| 40 | TAATTCGCTGCAACCAGATC |
| 41 | ATAATTCCAACATGGGAGCC |
| 42 | CATTGCTTAATATGGGAGCC |
| 43 | CAATGCTTAATACCGACACG |
| 44 | GATTGCTTAGACCCTGCACG |
| 45 | GATTCATTAGACCAGGCGCT |
| 46 | GATTCTACATGCCACTAGCA |
| 47 | CCTGCGAACTGGCCTGAATA |
| 48 | CGCAGCGGAAGGCTCAATAA |
| 49 | CCTACCGCAAGGCAGGATAA |
| 50 | CCTATGATAAGGCACGCACA |
| 51 | CGCTGTGCAAGGCTCGTATA |
| 52 | CGATTGTCAAGGCAGTGATA |
| 53 | CATTGCGAACTGCATCTAAC |
| 54 | GATAGTCCAATGCTACTGAC |
| 55 | GATTCGGTAATGCGCTGTAA |
| 56 | GACGTTTCAATGCAGCGTAA |
| 57 | GAGAGTGCAATGCCGACTAA |
| 58 | GAGATCCGAATGCGCGTACT |
| 59 | CGAGATCCAAGGCCCATGAT |
| 60 | AGCTTGCACAGTAACCATGA |
| 61 | AGAGTTGAACAGCATACCCT |
| 62 | TATCTGATCGGACGGCCAGT |
| 63 | TATTGACTACTGCGCCTCAG |
| 64 | TTGGACTATTGGGTATCGCC |
| 65 | TTGTCAGATTGGATGCGCTC |
| 66 | TATGCAGAATGGCGTGTATC |
| 67 | CATTGGATAAGCACTGATCG |
| 68 | CCCGGAATAAGGCCACGATA |
| 69 | CTCATAGAATGGACCAGATC |
| 70 | CATAGATTAAGCACTCAGCC |
| 71 | CATGATGTAAGCACGCTACC |
| 72 | CAGGAGCGAAGCAGATACTC |
| 73 | CAGAGCAGAAGCACTCACGT |
| 74 | TACATAGGCTTCAGCATCAC |
| 75 | TATTATACCTTGATCCGCGC |
| 76 | TAAACTGCTTGCATACGGCG |
| 77 | TATAAGCCTTGCAGCGGACC |

TABLE I-continued

| Seq. Id | 3' to 5' sequence |
|---|---|
| 78 | TTTAAGCGGTGGATCTAGCT |
| 79 | TTAATAGCCTTGAGCAGCGA |
| 80 | ATAAATGCTTGGAACCCTCG |
| 81 | GAAAGTTCATGGAATCGAGC |
| 82 | GCAAGGATTTCGACTCAGAC |
| 83 | CAAAGAATAATCGCTCCTCG |
| 84 | TAAAGCACTTATGACTCGGC |
| 85 | TTATAGCATTCTGTAGGCGC |
| 86 | TCGCTGACATTTGATTAGCC |
| 87 | CCTTGAATAATATCTCGGCC |
| 88 | AGGTCCAGAAATTGCTGCAC |
| 89 | AGCTCAGGAAATTCTAGCGA |
| 90 | AGCTATGCAAATTAGAGGCC |
| 91 | GGTAGGCTAATTTATGGCAC |
| 92 | CTAATGCAATTCAATGCCGC |
| 93 | CAACTGGCAATCAATACGCT |
| 94 | CCAAGCGAATGCAACGTATC |
| 95 | GCATAGCGAATTGGAGATAC |
| 96 | GCATGTCGAATGGATGATAC |
| 97 | GCACGTTCAATGGCTCGACT |
| 98 | GCAGCGCAATCTGTCGAGTA |
| 99 | AGCAGTGCAAATCCTGATAC |
| 100 | AGCTTCGCAAATCTGGTACA |
| 101 | AGCCTGCGAAATCTACTGAA |
| 102 | GCAGATCGAATTATGGAGAC |
| 103 | GCAGAGTCAATTATCATGCC |
| 104 | CGTTAGGCAATACATTTCCC |
| 105 | ACTGGTGCAAAGTCTTCGAC |
| 106 | GGTATATGAATGTGTCGTCC |
| 107 | GATAGTGCAATCTAGGTGAC |
| 108 | GCAGTGCAATGGATGTACTA |
| 109 | GCTAGGCTAATGTCCGGCTA |
| 110 | GGTAGCCTAATGTGTGCTCA |
| 111 | GGACGTGCAATCTTGTGACC |
| 112 | GAGCGCCGAATCTAGTCGAA |
| 113 | GGGAGCGACCTCTAGCTTAT |
| 114 | GCGGGTCGAATCTCGCTTAA |
| 115 | CGCCGCGCAAGCTGTATTAA |
| 116 | CGGCTGCGAAGCTGTCTTAA |

TABLE I-continued

| Seq. Id | 3' to 5' sequence |
|---|---|
| 117 | CATCCGCTAAGATCGGTTAA |
| 118 | CGTGCAGCATAATCCATCAG |
| 119 | TGAGAGCTGGATCGCATTCC |
| 120 | TAGGTGCTAGGATCTCAGCC |
| 121 | TAGGTATCAGGATTCAGGCC |
| 122 | TGCGCCAGTGAGTCGTATAT |
| 123 | CAGCAACGTGGATCAACTAT |
| 124 | CAGCGGCTAAGATCAATACC |
| 125 | GCAGCCTAATCTGGCCTAGT |
| 126 | GGGCCTGTACCTGCAATTCA |
| 127 | TAGGCCGGACCTGCTGTTAT |
| 128 | TAAGCCGCCACGGAGTGTTA |
| 129 | TAAGGCTCTTGAGACGTAGT |
| 130 | TAAGCCCGATCAGCATGGAC |
| 131 | TTGCCCGTAGTCAGCTTAGA |
| 132 | GAAGCACCGATCAGACACTG |
| 133 | CAGGCACCAAGTAGCACAGT |
| 134 | GGTGCGCCATGTACTCAGTT |
| 135 | TCAGGCTTATCGAGCGCGTT |
| 136 | GCAGGCAGATCGACCTAGTT |
| 137 | GGATAGGGACTCAGATATAC |
| 138 | GCATGGTTACCTACGCCAGA |
| 139 | GGAGGCTGACTCATACGCAA |
| 140 | GGAGCCTGACCTAGTCGATA |
| 141 | GCGGCCAATTCGGCGATAAT |
| 142 | GGTGCTCGACATTAGGCCAT |
| 143 | GATCCCACATAGCGGACAAT |
| 144 | GATCCAATCTGTCAGCACAT |
| 145 | GAGCCAATCTGACTACCAGT |
| 146 | TGCTGGATATGACTGTCGTA |
| 147 | TGCTCTGCACTGCTGACGTA |
| 148 | TCACCAGCCAGACTGTGTAG |
| 149 | AGGAGCAACCATCATGCACG |
| 150 | GGGCATACCTATCCCGAGAT |
| 151 | CGGGCGATACCACTCAGATT |
| 152 | AGCGGCAACCAGACATACGT |
| 153 | CACGCCATACCAAGGAGAGT |
| 154 | CAGTGCATACCAAGCGACGA |

TABLE I-continued

| Seq. Id | 3' to 5' sequence |
|---|---|
| 155 | CAGGCAGTACACAATCTACG |
| 156 | TACGTCGCATCCATAGCTGA |
| 157 | GAGTGACACCTCAGCAGATA |
| 158 | CTACAGCACCTCAGGAGAGT |
| 159 | CTCACGACATCCAGGAGTAT |
| 160 | CCAGCACGACAGAGAGATGT |
| 161 | CGCACACACCTGAGAGAGAT |
| 162 | GCGCACGCACTCAGATGTAA |
| 163 | AGACGCTCAACCACGAGAGT |
| 164 | GACGCCACAGTCACTAGAGA |
| 165 | GGCGCACACTGTACTCAGAT |
| 166 | CGAAGCGCCAGTACCAGATA |
| 167 | GGGTCGCTACCTACTCTGAT |
| 168 | GAGACATGATCTACCAGTAC |
| 169 | GGACGCTTACTCAGCAGTCA |
| 170 | CGGGTGTTACAGAGCTATCA |
| 171 | CGCGGCTTACACAGACATTA |
| 172 | CGGAGCTTACACATTAGGAG |
| 173 | CTGAGCATACACTTCACGAT |
| 174 | CCGATCATAACTGTAGATGC |
| 175 | CCGCCGATAACTGCTTGAGA |
| 176 | GGCCATATACGAGATGTAGA |
| 177 | CGTCCCTTAACGGCTGGTAT |
| 178 | ATACCCAGAACGACTATGCG |
| 179 | ATCCCACGAACGATGAATCT |
| 180 | ATCCGCAGAACCGGCGATAA |
| 181 | CCTCGCCGAAGCGTGTTTAA |
| 182 | GCGCCGCACAGAGTCTTATA |
| 183 | CGCGCTGCACAGAGCATATA |
| 184 | CCGCTGACACAGGCAGATAT |
| 185 | GCGTATGACCAGGTGTATAT |
| 186 | CTGTATGAAGGTGCTGTACT |
| 187 | GTTTCGCACGAGGATGTATC |
| 188 | GTGCTCGCAGAGGATTTATC |
| 189 | TAGGCCAGAGTAGCGACTTA |
| 190 | CAGATCCTAAGAGCAGTTAC |
| 191 | TAGATGCTAGGAGCGATTCA |
| 192 | TAAGTCGGTGGAGCATATCA |
| 193 | TAAGCGCGTGGACTCCTAAA |

TABLE I-continued

| Seq. Id | 3' to 5' sequence |
|---|---|
| 194 | TAAGTGGACTGAGCGCATAT |
| 195 | TATACGGCAGTGGATCAGAT |
| 196 | CTATACGCAATGCACTCAGA |
| 197 | CTATCGTCAAGTGATGGACC |
| 198 | TATAGACTAGGTGATCGAGC |
| 199 | TAGTACGAGTGGGCATCAAA |
| 200 | TAGACGTAGTGAGCATGACT |
| 201 | TGACGAGTTAGGATCTATGC |
| 202 | TTACGAGTGTAGCGTCCATG |
| 203 | TCGTCGTAGCATCTCGCAGT |
| 204 | TCGACGTAGGATCGCAGTAC |
| 205 | TCAGTATCATGGAGTACGAG |
| 206 | TGCACTAGATGGGATCGACT |
| 207 | TGCGATTACTGCCGTCACGT |
| 208 | TGGACTCTATGGCAGCCGTA |
| 209 | TGACAGCAGTTGCAGTCCGT |
| 210 | TACACAGGCTTGCAGCTCGA |
| 211 | TGCAGCGGAGTGCCTCATTA |
| 212 | GCGCAGGGAGATCCATATCA |
| 213 | CGGCAGCCAAGTCCAGTATA |
| 214 | CAGCGCCCAAGACGTGTATA |
| 215 | GTGCCTGCATAGCGATAGTC |
| 216 | TGCCTGCGAGAGCCTGTATT |
| 217 | TGGCATCGAGAGCCGTTCTA |
| 218 | GCAGGAGCAGAGCTTATATC |
| 219 | GCGGGATCACGACGTTTACA |
| 220 | GTGGCGATAGAGCATTCTCC |
| 221 | AACGCGAGAAACCATTTGCC |
| 222 | AGGCAGACAACTCAATCCGG |
| 223 | AGGAGAGCAACCTACACTCG |
| 224 | AGCCAACGAACCTACATGGG |
| 225 | CCGCAAGCACGTCGAATGAA |
| 226 | GCGCATGGACGACAAACGTA |
| 227 | GCCAGGAGACGTAGATATTA |
| 228 | GCGCATAGAGAGAGATCATC |
| 229 | TGGTATATCGGTAGATTCGC |
| 230 | GAGCTATAAGGTGGATTCAC |
| 231 | CGCGGATAACTTGATTCACC |

TABLE I-continued

| Seq. Id | 3' to 5' sequence |
|---|---|
| 232 | GTCGGCTTACCTGATAGCGA |
| 233 | GGAGCTATACATGCCTATCC |
| 234 | GGTGCCGTACATGCTCGTAT |
| 235 | TCGGCTTGACGTGCTCGTAT |
| 236 | GGGCTGTGACTAGACTCTCA |
| 237 | GCGAATTTAGTAGACGCACA |
| 238 | GAATCTCGAATAGCGGTACA |
| 239 | GACAGTTGACATGACAGTAG |
| 240 | GACATTGACATCGCATACAC |
| 241 | GAGTTTAGAATCGTGAGCAC |
| 242 | CTATTCGCAAGTGTCGAGCC |
| 243 | GTTATGGACACTGCTCGACG |
| 244 | AGCGTTCTAAATGCGTCACA |
| 245 | CCGATATGAACTGTCACTAC |
| 246 | CGCGAATGAAGTCTACATAC |
| 247 | CCACTATGAAGCGATATACC |
| 248 | CACCAGTGAAGAGATACCGC |
| 249 | GCACTGTTACATGATACCTC |
| 250 | GCCAGTTACAGTCATGCCTA |
| 251 | GCGCAGCTAGATCCACTGAT |
| 252 | GCGTGCGGAGACCTCATTTA |
| 253 | GCTCACGAGGCACGCTTTAT |
| 254 | GCGCCAGTAGCACGCTTATT |
| 255 | GGCTCAGTAGCACTCATCAT |
| 256 | ACTTGCACAGCACAATACGT |
| 257 | CGCCATACAGCACGATATTA |
| 258 | CCGCAGACAGCACGAGTATT |
| 259 | CCAAGGAGACTACACGATCT |
| 260 | GCACAGGTAGCTCGACGTAT |
| 261 | GTCAAGATGCTACCGTTCAG |
| 262 | CGATATGAAGCTCAGTGAAC |
| 263 | CCTATGAAGCTATCGCAACA |
| 264 | CTTATCACAGCATCCGAGAG |
| 265 | CCCGTGCAACGATTTGACAA |
| 266 | CGGCGGTTAAGTTCTAATCA |
| 267 | GGTCGAGCATGATAGCTTAT |
| 268 | GTGGTAGCAGCATAGCTTAT |
| 269 | TAGCGTGGAGCATCCTCAGT |
| 270 | CAACGGTGAGCAACTATCAG |

TABLE I-continued

| Seq. Id | 3' to 5' sequence |
|---|---|
| 271 | CTGGTTCGAGCAATCTATCA |
| 272 | TCGGGTCTAGGATGCTCTAC |
| 273 | TCGATGCACTGATGTCACTA |
| 274 | TCGTATATCCCATGCGATCT |
| 275 | TACGGTCCAGCATCAGCTTA |
| 276 | ATCAGTCCAACCTACAGATG |
| 277 | ATCAACTGAACCTCATACGG |
| 278 | TACTTCTGAGCAGGGAGCTA |
| 279 | TAGTTATGAGCAGGCGTCCA |
| 280 | CTTGTGACATCAGCCACGAT |
| 281 | CACGGAGCAAGAGCACATCT |
| 282 | CACGGGTGAAGAGCCATACA |
| 283 | CAGGAGTTAATAGCTCATCC |
| 284 | TAAGATTAGTTAGCAGCGCC |
| 285 | GAGTGATTAGCAGACGCCAC |
| 286 | CGATGATTACCAATGCCACG |
| 287 | GACTGATTAGCACATCCACA |
| 288 | GATTATGTAGCACTATGCCC |
| 289 | GCTATATTACGAGCTATGCC |
| 290 | GTTTATATCGAGGCAGGCCA |
| 291 | GTTACTATCCGATCAGAGCG |
| 292 | CGTCATGTACCATCAAGTCG |
| 293 | GTTATCTACGGATCATGCGA |
| 294 | CTGCCGTAAGTCTCATGCGA |
| 295 | CTAGCCGAATACTGCATACA |
| 296 | CTGCGTCGAGAATCGCGTTA |
| 297 | CATACACGACAATAGCTTCG |
| 298 | GATACCGACTCATACATTGC |
| 299 | GATACCGGAGGATCAGGAGA |
| 300 | GTATATGCAGACTACTGGAG |
| 301 | TATAGTCGATTATCCCAGCC |
| 302 | CATAGTACAATATCCCGACG |
| 303 | CTTGACAGCTACTACCAGTG |
| 304 | CTGAGACAGCTATCGACACA |
| 305 | CTGAGTAAGTCTTCCACACG |
| 306 | TCGGATATACTATGCGTCAG |
| 307 | CGTAGGATAGAATGCACAGT |
| 308 | CATGATACACACTCACGAGG |

TABLE I-continued

| Seq. Id | 3' to 5' sequence |
|---|---|
| 309 | CGGAATCACGACTACATACG |
| 310 | GGGTATCACGAGTCACCTCA |
| 311 | GAGAGAATCGTATCACAGCC |
| 312 | GAGTATGTAATCTACCTGCC |
| 313 | GAGTAATCATAGTAGCAGCC |
| 314 | GACTATATCCAGCACCGAGG |
| 315 | GACATATAGCTCCACTCAGA |
| 316 | TAGACCTAGTTGCAGCGCGA |
| 317 | TACTACACGTTTCACGGCAG |
| 318 | GTACATATCTGTCACGCGCA |
| 319 | TAGTATATCCTACGCCGCTA |
| 320 | GAGTATATCGCAATGCCAGC |
| 321 | GAGTTGTCACATAGGCCACC |
| 322 | GACGCATGACATATTCCTAC |
| 323 | GAGACACTTGACAGTAGCCA |
| 324 | GGCTAGTTACTCAGATCACA |
| 325 | CGCAATAAGTCTAGCTCACT |
| 326 | CATGTACTAAGCAGTCACAC |
| 327 | CTAGTTAATGTCAATCCGGC |
| 328 | GACTGTGTAATCATTGCAGC |
| 329 | CGTTCGTGAATCAGCACAGC |
| 330 | ATTCGGTCACACAGCACAGA |
| 331 | ATCTGCTGACACACACTAAG |
| 332 | AGCTCGCTAAATATGTAGGC |
| 333 | ACTGTCGCAAATATCACACG |
| 334 | ACTGTCTGACCAACCAATAG |
| 335 | GTTACTAGCTGGACCTCAGA |
| 336 | TTATAGACTGGTGCGGAACA |
| 337 | TTAGCATACTGTGCGCGAAC |
| 338 | TGTGCTGACTTAGGTCGAAT |
| 339 | TCTCGGGACGTTGCGCTATA |
| 340 | TGTCCGCGACGTTGGCTATA |
| 341 | TGTTCGTGACTGTGCGCTAC |
| 342 | TGTCAGGTACTGGTCGCTAC |
| 343 | TTCATGTACTGTGGCTACCG |
| 344 | TTTACTAGAGTGGCGCATGA |
| 345 | TTAGATAGATGTTCGGCCAG |
| 346 | CTCAATAGATTATAGGCGCG |
| 347 | TCGAATCGCTGTTACGGAAA |

TABLE I-continued

| Seq. Id | 3' to 5' sequence |
|---|---|
| 348 | TCAGACTAGGGTAGCGCATA |
| 349 | TCAGCAGTATGTAGGCAGTA |
| 350 | TAAGCCGGGTCACGCTATTT |
| 351 | TATGACCGATGTGCAGGTAT |
| 352 | TTAGCACGCTCGGCGATGTT |
| 353 | TTCACACGGTCTGCGAGCTT |
| 354 | CTTCAGACAGGAGGAGATAT |
| 355 | TCCAGCCGACGTGCGATTTA |
| 356 | TCCAGCGTACCTGCTTGTAG |
| 357 | CTCCAGTCAAGTGCTTCGAG |
| 358 | CTCCAGCGAAGTGATGAGAA |
| 359 | TGTCAGCGGATCGCCATATA |
| 360 | TCCATGCGAGGATCAGGTAT |
| 361 | TGCAAGCAGTTCTCAGCGTA |
| 362 | TGTAGGACCTGTGCTCACTG |
| 363 | TTTATCGCAGTGCTCAGGCT |
| 364 | TATGTCAGCAGGCCCAGCTT |
| 365 | TTCTCGTAGCTGCGCCTAGT |
| 366 | TATTCGAGCTAGGGACGCAT |
| 367 | TATTTATACTGCGAGCGAGG |
| 368 | GACCTTACACTGGCACGAGA |
| 369 | TACTGATAGCATGGGACGTT |
| 370 | TCGGATAGCAGTGCGCTCTA |
| 371 | GCTGATGCACGAGGCCATTA |
| 372 | GCTGGATCACGAGGCTCATA |
| 373 | CGCTTTGTACCAGGCCATAG |
| 374 | CGTGATTGACCAGACCCAGT |
| 375 | TACGCTGGATCAGACGGTCA |
| 376 | ATCCTGAACGCAGAGACACG |
| 377 | ATCGTTGCACCAGAACTACA |
| 378 | CTCTCAGGACCAGCATGATA |
| 379 | TCTGAGCGATCTGCCAGTCA |
| 380 | GGTGAGACCTATGTATATCG |
| 381 | TTAGAGTCTTAGGCATGTCG |
| 382 | TTATAGCCGTAGGCAGGTAC |
| 383 | CTCTAAGTATTGGACACGCA |
| 384 | GCTAGGATATAGGACACTGA |
| 385 | GCTATCGAATGTGCAGTACG |

TABLE I-continued

| Seq. Id | 3' to 5' sequence |
|---|---|
| 386 | TCTATCCACTGCGGACGAGT |
| 387 | TCATACTCATGTGGAGCTCT |
| 388 | TCATCGAGATCGGCCACTGT |
| 389 | CTTATGATACCAGTCAGCAC |
| 390 | TATTGGTACGGAGTTAGCCC |
| 391 | GTAGATGACCCAGTTCCAGC |
| 392 | GGCTGTTACCGAGTCTCAGA |
| 393 | TGCTAGTTAGGAGTATCGCA |
| 394 | GGCTTACTAGCAGTCACGCA |
| 395 | CAGCATATAAGAGTCGTACC |
| 396 | GGCATCATAGACGCTACGCT |
| 397 | GAGTCAGCAATCGCAGCTAA |
| 398 | GATCAGTAATGCGGAGCAAC |
| 399 | TATCATAGATGCGGACGGAT |
| 400 | CAGTCCACAAGCGCGAGTAA |
| 401 | CGTAGCCCAAGTGCCGATAT |
| 402 | GACGCACCACAGGCTAGTAT |
| 403 | CTAGCATACCAGGCGAGAGT |
| 404 | AGTGCATCACAAGAGACTCG |
| 405 | GCCATAGACGAGGCAGTATC |
| 406 | GGAATACGCTGAGATATACG |
| 407 | GTTAATCGCTCAGCAGCATT |
| 408 | CACAAGCGACCAGAAGCGTT |
| 409 | TCTTATCGACCAGGGCGGTT |
| 410 | GACACTATCCCAGACGGAGT |
| 411 | TTACTAGGTTCAGCGCGATC |
| 412 | TTCAGATCCTCAGCGTAGTC |
| 413 | TCTCAGATATTCGTAGCAGC |
| 414 | TGTCTATTAGTAGCTGCGAG |
| 415 | TAGATACTCTGAGCTAGGAG |
| 416 | TGTCTCCAGATCGTGCGAGT |
| 417 | TTCGGTCTAGCTGGTAGCAT |
| 418 | ATCTGGCGAACAGGTGCATA |
| 419 | AATGCGCGAAACGGCGATAC |
| 420 | TTTGTCGCAGTAGTCGCATC |
| 421 | TGTTGTGCAGTCTCCAGGCA |
| 422 | CATTGTGAACTCTACGTCAG |
| 423 | CGGATGTCAAGCTCTCACAG |
| 424 | CTGCGGCAATACTCTCAGGT |
| 425 | ATGCGGAGAACCTCTGACAA |
| 426 | GCGCGTGAATCCTGTGACTA |
| 427 | GCGCTCTGAATCTGTGAGAA |
| 428 | GCGCTATGAATGTCAGCTAA |
| 429 | GCCGAGGTAATGTGATATAC |
| 430 | GCCGCGTGAATATGAAGATA |
| 431 | GCGGCGAGAATCTTCCGATA |
| 432 | GATGGTAGAATCTCTCTCAC |
| 433 | GCTGCGGGAGACTATCATCT |
| 434 | GCTGGATTACGATGCCATAG |
| 435 | GTTGATTCACGATGGCAGAT |
| 436 | CTTCACGCAAGTTGTCCAGA |
| 437 | CTTACGCCAAGTTGTCAGAA |
| 438 | CTTGCGTCAATAGTCTGAGA |
| 439 | CCTGTGCGAACTGTCTTACA |
| 440 | CTCAGTCCAAGTGGCTCAGA |
| 441 | CCATAGCGAAGCGCACAGTA |
| 442 | CCAGCACTAAGCGCAGATAG |
| 443 | CTCCGCCTAAGTGGCAGTAA |
| 444 | TGCGCCTGACGTTCGGATTA |
| 445 | TGTCCAGTAGCTTGAGAGTC |
| 446 | GCTCACAGAGTTTGATAGAC |
| 447 | GCTACAGGAGTGGATATTAC |
| 448 | GTGACAGTGGCAGATATAAC |
| 449 | TCGCACTGAGCTGTAATCGA |
| 450 | TCTTATGAGATGTAGCTCGC |
| 451 | TCCATCTAGCTGTAGCCGAA |
| 452 | GTCATAGCAGCTTAGACCTA |
| 453 | TTATGCTGACTGTGCTCGAC |
| 454 | TTAGTGCAGTATTAGTCGCG |
| 455 | TGTCTGACCTTGTAGCCGAC |
| 456 | TGTTGACACTTGCGTACCGG |
| 457 | TCTTAGCATGTGCGACGACG |
| 458 | GCTAAGCTCTTGCACTGACG |
| 459 | CATAAGACTTTCCAATCGCG |
| 460 | CTGAAGCACTTTCCACGAAG |
| 461 | CTGAACCCGTTGCAGAGAGA |
| 462 | CGGAACCGATGGCACAATAT |

TABLE I-continued

| Seq. Id | 3' to 5' sequence |
|---------|-------------------|
| 463 | GGTGACCGATGGCTACTCAT |
| 464 | ATGGCGCGAACCCTGTACTA |
| 465 | CATCGCGGAAGCCACGTATA |
| 466 | GACGGCAGAATGCAGTATAT |
| 467 | CGCGGAAGAAAGCATATTTG |
| 468 | CTCAAGGGCACGCAATCTAG |
| 469 | TCACAGGAGGCTCGACTCTA |
| 470 | CGACAAGGCATTCACACTAG |
| 471 | ATAAAGGTCATGCCAACCGC |
| 472 | TATAATGCGTTTCACGTCCC |
| 473 | TCTAATGCCTGACACGAAAC |
| 474 | TGAATGCCGTGACTCGTAAA |
| 475 | GTGGAGGCACTGCATCATAA |
| 476 | GTGGTGTGACCTCGCCATTA |
| 477 | GGAGATGCACTACGGACTAT |
| 478 | GAGGATCGAATACTGTCGTA |
| 479 | CGGAGAGCAAGTCATACGAC |
| 480 | GCAGGAGACGGACTATACTA |
| 481 | GAGCGTGTAATCCGATCTAA |
| 482 | CGATACGGAAGGCGCACTAA |
| 483 | CGATAGGTAAGGCGACTCAA |
| 484 | GATGTGGCACGACGATCATA |
| 485 | TGAGTAGGCAGTCCGATCTA |
| 486 | TGATAGGCAGTGAGTTCATC |
| 487 | TTATGGCGAGAGTTGTCATC |
| 488 | GTTTAGGCACGATGCTGTAT |
| 489 | GCGTTAGGACCATAGTCTAC |
| 490 | CCGATGCGACAATACGTTAG |
| 491 | TCTAGCGTCCCATAGCGTAG |
| 492 | CTGTCTGGACCATAGCAGCA |
| 493 | CTGCTTGCACGATGAGCGAA |
| 494 | TAGCCCGGACGATGTAGTCA |
| 495 | CCGCTACAAGCATTGGGAAT |
| 496 | CGGCTAGAAGAATGAATGCT |
| 497 | CCGATGATAAGCTAGTATGC |
| 498 | GCGGATAGACCATTATTGAC |
| 499 | GCCACTAGACCATCGGTGAT |
| 500 | GCACGCGGACCATCGTTTAT |
| 501 | GCCGCTCGACCATAGTGATA |
| 502 | GCCGAGTCACCATGCTGTAT |
| 503 | CACGGGTCACCAAGCGTATT |
| 504 | GACGGCGACCCAGGTTATAT |
| 505 | TGTGCGTCAGCAGTTAGTAT |
| 506 | GCTCGGCTACCAGTCGTTAT |
| 507 | CGCTGGACACCACTGTGATA |
| 508 | CGGTGGAGACCAGATTATAT |
| 509 | CGCGGGACACCAGCATATTA |
| 510 | GCTCGCGCATTAGCATATAA |
| 511 | GCTGACATCCACGCATTGAG |
| 512 | CGCTGATCCACCGAGATTAG |
| 513 | ACGCAACCAACAGCGAGTGT |
| 514 | CACAGACCACAAGCTATGGG |
| 515 | CCTAGCCCAAGGCATTAGAA |
| 516 | CCGTAGCTCCAAGGCATGTA |
| 517 | CAGTGCGCCAGAGCAAGTAA |
| 518 | GAGCCACCACGAGTCATGTA |
| 519 | GGTCACCACTCAGCGATGTA |
| 520 | GTGTGCCACTAGGCCGATTT |
| 521 | GGAGACCCGTAGGCATAATT |
| 522 | CGCTGTAAGGATGCTGAATA |
| 523 | GTCGTGCAGGATGCCATATT |
| 524 | GTTCCGCACGATGCCAGATT |
| 525 | GCTGCGACCATCGTCAGATA |
| 526 | GTCTAGCGATCATGCTCAAT |
| 527 | CTCTACGAATCATGCGGAAG |
| 528 | CTTAGATACTACGAGCACGA |
| 529 | GTGACGCTACGTGAGCCTAA |
| 530 | TACCGTGTACGTGAGCGCAT |
| 531 | TACTGCGACGTAGCGAGTCA |
| 532 | TACTAGGTACTCGCGGCACT |
| 533 | TACTGCGTACTCGGAGCATA |
| 534 | GCTCACGTACTCGACAGAAA |
| 535 | GTGTACTATGTAGCGAGATC |
| 536 | TAGTAGTACGCTGTCAGAGC |
| 537 | TGTCGTCGAGTCGTAGATAC |
| 538 | GTAGTACACGGAGTGATCCT |
| 539 | GTAGTACGAGCTGAGACTCT |

TABLE I-continued

| Seq. Id | 3' to 5' sequence |
|---|---|
| 540 | GTGACTAGCTCGTAATTCTG |
| 541 | GAGACACGGTACTAGAGACT |
| 542 | CAACAGCGTCACAGACATGG |
| 543 | CTATGAGACCACCTCGATAT |
| 544 | ATTCGGCGACAACGCATTTA |
| 545 | GTTGCCGTACTAGGGATACT |
| 546 | GGCGCAGTACGATTGACTAT |
| 547 | GTGCGACGAGCTTGTCACTA |
| 548 | CGCGTGTGACTATTGATACG |
| 549 | CGTCTGCGAACTTTGCTACG |
| 550 | CTGTAGCGAAGTTCTCATAC |
| 551 | TCGGCGTTACGTGCTGACTA |
| 552 | TGAGCTATACTCGTCGTCAG |
| 553 | CCGATACTAAGCGTTACGAA |
| 554 | CGTCATACATAGGACTAGCA |
| 555 | CGCAGGCTACAGACTATTAT |
| 556 | GCGAGCGTACTATACATAAC |
| 557 | GCGAGTCTACGACCTCTATA |
| 558 | CGGTACGCACGACAGTCATA |
| 559 | CGGTACATACGACTATACAG |
| 560 | CGCTAGATACACCACTGATA |
| 561 | CTCTAGGTACACTACTGCAT |
| 562 | CGTCAGAGACACTGGAATAG |
| 563 | CTGCGCGTACACTCGGATAT |
| 564 | CTGTCGCTACACTCGTGAGA |
| 565 | GTAGACGCCTAGTCAGATAG |
| 566 | GAGCGACTACGAGCCACTAT |
| 567 | GTGCGACTACGTGCATCACT |
| 568 | CGTAGGACACGAGCGTATAT |
| 569 | GGCGACGACGTGACTATACT |
| 570 | CGGTCACGACGACGAGATAT |
| 571 | GCGTCACACGAGCCGATATT |
| 572 | GTCGCTCACGATGCGGATTT |
| 573 | GACCGACAGATCGTGACATC |
| 574 | GACCACGTACATGAGCTGAC |
| 575 | GGCGACGTAGATGATATTCT |
| 576 | GAGACTGTAATCGCATATCC |
| 577 | GACTATGTAATCGAGCCTAC |
| 578 | GATAGTCGAATCGCGGATAA |
| 579 | TATACGGACTGCGCCCTAGA |
| 580 | TAGTCTAGCTGAGCCATCGA |
| 581 | GTATATGACCTAGTGCCACG |
| 582 | GTGTTGTACGATGTGCTCCA |
| 583 | GAGTCTGACATAGGGCACCT |
| 584 | GAGTTGCACGTAGACGATAC |
| 585 | GACTCGCGCATAGACACATG |
| 586 | GACAGGCTACGAGACTAGAT |
| 587 | GTGACGGCACTAGCAATATA |
| 588 | CTGCTCTGACACGCGAGTAT |
| 589 | CGGCTGTGACACGAGCTATT |
| 590 | CTGGTGCGACACGCCTATAT |
| 591 | GTCAGTGGACTAGCCCTACA |
| 592 | ATCGAGTCAACCGGCCTAGA |
| 593 | TCGATAGCCTACGTGCCGTT |
| 594 | GGAGACCTCTACGCACTGTT |
| 595 | GCGTGACAGCTCGCACTATA |
| 596 | GCGTAGCTCAGCGACATTAA |
| 597 | GCTATACGCACCGTCATGTA |
| 598 | CGGATACACTCAGCAGAGAT |
| 599 | CTACTTACAGCAGCGACGAG |
| 600 | ATCTCGACACAAGCTAATCG |
| 601 | CATCGGATACACGCATACAG |
| 602 | ACATACAACACCGCTTAGGG |
| 603 | TACTGAGTCCACGCTCGGTA |
| 604 | GATACAGGCTAGGACCGGAT |
| 605 | GATACATTACTCGACACGCG |
| 606 | CGCTACAGAGATGCACAGAG |
| 607 | CCGACTGTAACTGCGATGAA |
| 608 | GGTGTTATACGTGCATAGCC |
| 609 | CTCGTATTAAGTGCGCTACC |
| 610 | TATAGTATCGAGGAGCGACC |
| 611 | GTATAGTACGTGATAGGCTC |
| 612 | GTACGATACGTGACTAGAGC |
| 613 | GTAGGTCGAGCTGCATACTC |
| 614 | TTACAGTAGTCTGCATCCCT |
| 615 | CTAGTCAAGTCTGCATACAG |
| 616 | CTGTCTAATACGGCCACATA |

TABLE I-continued

| Seq. Id | 3' to 5' sequence |
|---|---|
| 617 | CTCGCAATACGTGTACCGTG |
| 618 | TCCGATCTACGTGACGGTGA |
| 619 | TCTCGCCGACGTGGTCTTAA |
| 620 | TCTGTCCACGTCGCGGTTAT |
| 621 | TCGTCCTGACTCGCTGGTAA |
| 622 | GTCCCTAGACTCGCAGTGAT |
| 623 | GCGACAGTAGCTGCAATGAT |
| 624 | GACGTAATATCGCCACATCA |
| 625 | GACGAGGTACAGCGCATACA |
| 626 | GCAGGTCTACGACGCATGAT |
| 627 | GCAGAGTACGGACGCATATC |
| 628 | GAGTAGATACAGGTCACGAT |
| 629 | GAGCGATCACACGTCCGATT |
| 630 | GGTCGCATAGACGTATCAGT |
| 631 | GGTGTCTCACGAGTATCGAC |
| 632 | GTAGGCTAGACGGTCCACTA |
| 633 | GACGGACACTGAGCACATAG |
| 634 | GACACCTATGTAGCAATGAC |
| 635 | CACAGTACAATAGCACCTGG |
| 636 | CACCAGAACGTAGGCACAGT |
| 637 | CACTACTCAAGAGCCAGTTA |
| 638 | CGCCGACGAATAGCCAGATA |
| 639 | GCCGCACTACTAGCGATGAA |
| 640 | GACCAGTTACGAGCAGCGAA |
| 641 | GATCACGTAGGAGCACCGTA |
| 642 | GTACGCAGAGGAGTCATCCA |
| 643 | GTCGCTGACTAGGATCACGT |
| 644 | TACGCAGACTCGGACTCGAT |
| 645 | GTCGCTATATCGGACCTAAC |
| 646 | ACTCGCATAAACGACAGTCT |
| 647 | TGGAGTCGAGTAGTACATAC |
| 648 | TACGACATGGTAGGACGCTA |
| 649 | TGACTTCTACGTGGCGATAT |
| 650 | TACGCTCCGAGAGGCGATTT |
| 651 | CACCTTCGACGAGCAAGAGT |
| 652 | TACGCTCGCTCAGCTTAGGT |
| 653 | TACGGCATCGACGCTATTGC |
| 654 | TACGGCGACTGAGATGCCAT |
| 655 | TACGTGCTAGGAGATGTAAC |
| 656 | TATCGTCTATCAGATTGCCC |
| 657 | TATCGTATCCACGTTCCGAG |
| 658 | GATCGTACATCAGTGTCCAC |
| 659 | GAGTCTATATCAGTAGCGAC |
| 660 | GTTAGTCGATCAGTAGAGCA |
| 661 | GTCCTACGATGAGTGACGCA |
| 662 | CGTCTTCTAAGCGTGCTGAA |
| 663 | GTCTCCTACCGTGAGCAGTA |
| 664 | ATCTCACTACAAGAGCCTAG |
| 665 | CTGTGACGACCAGACGCTTA |
| 666 | CTGAGCGTAAGTGATTGTAC |
| 667 | CTCGTAGCAATAGATTTCCC |
| 668 | CTACGTGCAATAGCAGCTCA |
| 669 | CCGGCAGTACAGATAAGTCA |
| 670 | CGCCGGATACAGAGTAATCG |
| 671 | CTCAGCATACATAGTACAGC |
| 672 | CCGAGCTTACAACGTGTGCA |
| 673 | GACGCATTACCACTGGCGAT |
| 674 | CAGGGTGTACCACGAAGCAT |
| 675 | CGGTGTTTACAGCAATCCAT |
| 676 | CTGGCTGCAATAGCGCGATA |
| 677 | TGGGCTACAGTTGCGCTCAT |
| 678 | TCTGGCATAGCAGGTGTCAC |
| 679 | GGGATTCTACCAGTTCGCAC |
| 680 | GAGGATGCAATCGTAGTCAA |
| 681 | AGGGATAACCATGCACACCG |
| 682 | CATGAAGACTTTGCACTACC |
| 683 | CGCCGACCAATGGGCATATA |
| 684 | CCCGAGCCAACTGGAGATAA |
| 685 | CCCGCAGCAACTGGGATTAA |
| 686 | GCCATAGGAGCAGCGATTTA |
| 687 | CCGCTTGCAGCAGACGATAT |
| 688 | CCGTTTGCAGACAGCCAGTA |
| 689 | CCGTTTACAATGAGCACACA |
| 690 | CGTTCTTTAATGAGCGACAG |
| 691 | CGAGCCTTAATGACGCACAA |
| 692 | GGCAGCATACTCACGATCAT |
| 693 | CTGCGAGCAATCAGCCGATA |

TABLE I-continued

| Seq. Id | 3' to 5' sequence |
|---|---|
| 694 | CCGCAGCAAGCTATCGAGAA |
| 695 | CGGCGTTCAAGCAAACCGAA |
| 696 | CAGTTTACAAGCATATCCCG |
| 697 | CATTGACGAAGCATAGTTCC |
| 698 | CATAGTGCAAGCAGCGACAC |
| 699 | ATCTGTGCAACCATAGTACC |
| 700 | ACTTGAAATGAGAAGCCCGT |
| 701 | CAGGAGAAGCGAATAGCCTC |
| 702 | CCAGAGAGAGCAATATCCGC |
| 703 | CAAGGAATATACAGGCCCGC |
| 704 | CAGAACTGAATTACAGCGCC |
| 705 | CATCAGACAATTACAGCTCG |
| 706 | CACCCGATAAGAGCATACGG |
| 707 | CACTCCAGAAGCACGATAGG |
| 708 | CAGCACCGAAGCAGAAGTCT |
| 709 | CAGATCAGAAGCAGGACGCT |
| 710 | CAGACCATAAGCACAGGCGT |
| 711 | ACAACACAAATGGCGCGGCT |
| 712 | ACGCAGATAAATCACCTCGG |
| 713 | CAAGACAGAATACTCTCCGG |
| 714 | CACAATACAATAGGCTCGCG |
| 715 | CAATAAGACATAGGCCGCCG |
| 716 | CACAACGGATTAGAAGCGCG |
| 717 | GACATGATATGAGAATGCGC |
| 718 | AGCAAACTAAGAGCCGGGTC |
| 719 | AACAATACAACCGTCGGCGG |
| 720 | AAATAACTAACCGCCTGCGT |
| 721 | CAAACACGAAGAGCCTGTCG |
| 722 | CACTAATCAAGCGACAGGCG |
| 723 | CATATACCAAGCTATCAGCG |
| 724 | CACATTCAAGACGATCACGT |
| 725 | CACCTATGAAGAGACTCACG |
| 726 | AACTATATCAAAGCCCTGGC |
| 727 | ACAATACCAAATGCGCCGGG |
| 728 | AGAAACGCAAATGCCTCTCG |
| 729 | CGAAAGCATAATAGCGGTGC |
| 730 | GGCAGAATCTCGTGTACTAG |
| 731 | GGTACATTATGCTAGAGAGC |
| 732 | GATACATGATGATAGCAGCG |

TABLE I-continued

| Seq. Id | 3' to 5' sequence |
|---|---|
| 733 | AGAACAGGAACATCGCTGCC |
| 734 | AGATAAGCAACATCCTGTCC |
| 735 | CATAAGCTAAGATCCTGGAC |
| 736 | ATTTAGCGAAGAAGCATGGC |
| 737 | ATAGCTCAATCAACGATGCG |
| 738 | TATATCGCATCCACTCTGGG |
| 739 | CATCTCCGAAGCACATTGAG |
| 740 | CATTCGTCAAGCACTTCAGA |
| 741 | CATTATCGAAGCACGGTACA |
| 742 | GATTCGGACAGCACGGCATA |
| 743 | GCTCCGGCAGTCACGATTAA |
| 744 | GACTGTCGAGCACCCATTGA |
| 745 | GATCGTCGAGCACGCCTAAT |
| 746 | GAGGTCAGACGACGCCTATA |
| 747 | GCGCGTATAGCTCTCCATAG |
| 748 | TAGCGAGTAGCACTTCGATA |
| 749 | CTAAGTGTAGCACCACATCA |
| 750 | GTAGATCGAGCAGCCAGTCT |
| 751 | GACATAGACCATACCACGTT |
| 752 | CGTCTTCGAGCAAGTGCAGT |
| 753 | CTCTCCGGCAGCGATATGTA |
| 754 | CCCTCAGCACGAGATATAAG |
| 755 | CCCTTGCGAAGCATTGCGAA |
| 756 | CTCCAGGCAATGAGAGCACA |
| 757 | CCCAGATCAAGCGATGCAGA |
| 758 | CTGAATCCAATGTACGTGAC |
| 759 | CGGCATTCAAGGTAGCGACA |
| 760 | GCCCGATTAAGGTGTGTCAA |
| 761 | GCCCGATCAATGGCTGCATA |
| 762 | CGCCATCCAAGGGCTGTATA |
| 763 | CGGATGCCAAGGGCTTCATA |
| 764 | GGTTGCGCCAGGTCATCTTA |
| 765 | GGTCCGGCATGGATCACTAA |
| 766 | GGCTGGCACATGATCGTATA |
| 767 | TGGTTGCACTTGGATCGAAA |
| 768 | TGATTGCCACTGCTCATACG |
| 769 | TGTTGATCCATGTCCATAGC |
| 770 | TTAAGGCACTTGATCTCAGC |

TABLE I-continued

| Seq. Id | 3' to 5' sequence |
|---|---|
| 771 | GTAATGCCCTGGACCGCAAT |
| 772 | GTTAAGCCTTCCACGGCAAT |
| 773 | GTTGCGCCATTGAGCCAGAT |
| 774 | GTTGCCCACCTGAGACGTTA |
| 775 | AATGCGCCACAAAGCGAGTG |
| 776 | CACCGGCCAAGAAGTACAGT |
| 777 | CATCCGCCAAGCAGAGTGAA |
| 778 | CGTTGCCAATGCACGAGCTA |
| 779 | GATGGCTGAATGACGTTTAC |
| 780 | GATTGCCTAATGAGTCTGAC |
| 781 | AATCAGCCAAAGATGTGGGC |
| 782 | AATCATGCACAAAGTTCGCC |
| 783 | ATTTAGGCAAGAAGCGCACC |
| 784 | AATTGGCTAAAGAGCGCACC |
| 785 | ACATTGGCAAAGCGAACTCC |
| 786 | AATGGGAGAAAGCCGACTCT |
| 787 | TGTGCTGGAGCTTCAGTCAC |
| 788 | GTTGTGCAGGATTATCGACA |
| 789 | GCTTGCAGACGAGTCATCAC |
| 790 | GGATGGATACTAGCGACTCC |
| 791 | GCTATGGCACAGGCATCTAC |
| 792 | GGACTGGCACATCCCGTATA |
| 793 | GGATCGGACCATTCTCACTA |
| 794 | GGATGGCGACATGCTCACTA |
| 795 | GAGCTGGCAATCGTCGTACT |
| 796 | GGATGGCTACATGATCTGAT |
| 797 | GGCAGCAATTCGGGCTAATA |
| 798 | GCCTAGCAATGTTCCCAGAG |
| 799 | GAGCGGCAATGATGATCCAT |
| 800 | TGGTGCATAGCTGCGATCCA |
| 801 | GGCTGCACAGGTGTATCCAA |
| 802 | GAGATGCCAATCGGCCATAA |
| 803 | TATATGGCACATCGTTGCGA |
| 804 | TGATGCCCACGTCGTCGTAT |
| 805 | ATTGATCCACACACAGTACG |
| 806 | AGCTGATCCAAGCAACGTAC |
| 807 | GTTGATGCAGATCGCGTATC |
| 808 | TCGTGGGCAGATCGCTTCAT |
| 809 | TGTGGCCGAGATGCCTTCTA |
| 810 | TTTGCGGACTTCGCTATCAA |
| 811 | TCCCATGCACCTGAGTGGAT |
| 812 | TTTCATGGAGCTGTCGCGTA |
| 813 | TTTACCTGTGGTGATAGCGA |
| 814 | TTGTCATGCTGCCCAGTCGA |
| 815 | CTTTCATGCAGGCAGAGCCA |
| 816 | CCTTTAAGCTGGCACACGAT |
| 817 | CCTATCAAGGATGCACACGA |
| 818 | CCGTTCAGAATATGACACAC |
| 819 | TAGGTCAGATCATGCGCGAC |
| 820 | ATGTGCATACAAGCTACGAC |
| 821 | CTGAGAATATGAGAGACGCC |
| 822 | ACTCACGCAAATGAACGGCG |
| 823 | CTTAGCGAATATGCGATACG |
| 824 | ACTCTGATAAATCCGACACG |
| 825 | ACTGTGCGAAATCCCAGACA |
| 826 | ACTGATGTAAATCCACACCG |
| 827 | ACGTGAACAATTCCACACTG |
| 828 | ACTGCACGAAATCGACATCG |
| 829 | ACTTCTGTAAATCGCAGCAC |
| 830 | CTGTCTTGAATAGCGATCAC |
| 831 | ATGCGGTTAAGCGGTAATAC |
| 832 | TACGCTGAGTCATCCGAATA |
| 833 | CTTGTGAGACACTCCGACAT |
| 834 | CTGGTGACATACTATCAGAC |
| 835 | CGTGCGTTAAGCTGTCGATA |
| 836 | CGGTATCGAAGCTGTGCTAA |
| 837 | CGCGTGTGAAGCTGCCTATA |
| 838 | CCTAGTAGAAGCTCCACAGA |
| 839 | TGTGTCGGAGTCGCCCATAT |
| 840 | TCTGTCGAGGTAGGCCATAT |
| 841 | GCTGTCGAGAGCGATCATCA |
| 842 | GCAGTCGGACGAGATTCTAC |
| 843 | GCGATGGTACTAGATCAGCA |
| 844 | GTGTAGGGACTCGTATCACT |
| 845 | GTACGAGCAGTTGAGCATAA |
| 846 | GTCAGTCGAGATTCAGCAGT |
| 847 | GTCGAGTCAGATGCACGTCA |

TABLE I-continued

| Seq. Id | 3' to 5' sequence |
|---|---|
| 848 | GTGTATCTAGCTGCACGCAC |
| 849 | GTTGTCTTACGTGCAGTCAG |
| 850 | TATGTACTCGTATCGACGCA |
| 851 | TCGTGTCGAGTATCCGCAAA |
| 852 | GTACGTTGACAGTCTGCACA |
| 853 | TTCGTAGAGGTCTGCCAATT |
| 854 | ATTCTGAGAGACAAGCCTCC |
| 855 | ATTCTGACACAATCATCGCG |
| 856 | ATTCAGAACTAATGCACCGC |
| 857 | AGGTATGAACCATCGCACAC |
| 858 | ATTTGATGAACTCCGCAGAC |
| 859 | GTTTGCTGACCTCGCAGTCT |
| 860 | ATTGCCGGAACGCATTATAC |
| 861 | TGTGTGGGATCGCCCTATCT |
| 862 | TTGAGTGAGCTGCGCTTATA |
| 863 | TGCGTGCAGGTGCCACTAAA |
| 864 | GTGCTGCATGAGCCAGTTCA |
| 865 | GGCTCTACATGGCGATAGCA |
| 866 | GCTCTCTAATTGCGGACACA |
| 867 | GGATATAAGTTGCGGCACTA |
| 868 | GGATGTAATGGTAGCTCCTA |
| 869 | GGATGACGAGGTCTCACCAT |
| 870 | GGATGCGACGATCTCGACAT |
| 871 | CGTGATCGAAGGCTGCACAA |
| 872 | CTAGATGTAAGTAGCTGGAC |
| 873 | CGAATGAAGGATCGAGACCT |
| 874 | CGGCCTGGAAGTCACTCATA |
| 875 | GGCCTTGGACTACCGCTTAA |
| 876 | TGCTTCGAGGGTCCCACTTA |
| 877 | TGCCTGGTACTGTCCGACTA |
| 878 | TGCTTGTGAGAGTCGCTACT |
| 879 | ATGCTTGCAGAACCGTCAGC |
| 880 | TGACTGTAGGGAGCCTCAAC |
| 881 | TGCTTGGCAGGATGTCTTAA |
| 882 | GGCTCCGGCATGAGTATATC |
| 883 | TGCTTTGCAGTGAGGCTCTC |
| 884 | CAATTTGGAACTAGCCTTCG |
| 885 | TTTGCTGCATCCGGCCTGTA |
| 886 | TTGGGCCACTGCGCTCTTTA |

TABLE I-continued

| Seq. Id | 3' to 5' sequence |
|---|---|
| 887 | TGTGAGCCCTTGGCACGTTA |
| 888 | GGTGGCCCGATCACATTCAA |
| 889 | GGCAGGGCACCTCAGTTTAT |
| 890 | GGGTGGCCCATGCTATCTAA |
| 891 | GTCTGGCCCTACCTATGGTT |
| 892 | GCGGGCACACCTCTGATTTA |
| 893 | GCGGGCGCACCATTCATTAT |
| 894 | GGAGCCCACCATGAGCTATA |
| 895 | GAATCTCCACCAGGCGGATA |
| 896 | GGATACGTCGCTACAGTGAT |
| 897 | TCGTATAGCTGTATCGACGG |
| 898 | CTAACTAGCTGTAAGCGACC |
| 899 | ACTAGATAACAGATGCGCCG |
| 900 | CAACTATCATCAAGACGGCG |
| 901 | CAACAGAGATGAAGCGCGTC |
| 902 | CAACATATCATAAGCGCGTC |
| 903 | GCAGATAGCATCATATACGC |
| 904 | GGAGACTGAATTAGCTCTAC |
| 905 | GTTAATTCATCTAGCGCGAC |
| 906 | AGGAATCTAACCACGCGCAG |
| 907 | AGACCAATAAGCACCCTGGG |
| 908 | AGACAAACATTCACGCCGGG |
| 909 | AGAATAAATTACTGCCCGGC |
| 910 | GAGCACATATTATTACGCCC |
| 911 | CAGAAGATAATATGCTCGCC |
| 912 | GAATAGCCGATAATCTCAGC |
| 913 | GAATAGCTTTACACTGCCCT |
| 914 | GAATCACTCTGAATGAGCAC |
| 915 | GGATCACACTGCCGGACTAT |
| 916 | GGACCCATAGCACTCTGATT |
| 917 | GAGGCATTAGCACCAGCTCT |
| 918 | GGATTATCAGCACTCAGTAC |
| 919 | GGGATCTCAGACGATGCTCT |
| 920 | GGGTATATCAGCGGATTCCA |
| 921 | GCAATTCGATCTAATGCTCC |
| 922 | ACCAATGCAAATAGGCGGCC |
| 923 | AGCAAATTAACACTTGGGCC |
| 924 | GAAACAAGCAGATTTGCGGC |

TABLE I-continued

| Seq. Id | 3' to 5' sequence |
|---------|-------------------|
| 925 | TTAATTCCGTGATATGCGCG |
| 926 | GGATCTAATGGTTATGACCG |
| 927 | GCATGAAGTGGTGTCAACTC |
| 928 | GCTTTAATGGTCGTGACGCC |
| 929 | GCTTAGAATTTAGTGCAGGC |
| 930 | GCGTCAGAATTTATGCCACA |
| 931 | GCTAGATAATTTAGGCCACG |
| 932 | GCTGATAATGCTGAGGACTA |
| 933 | GCAGAATTGCATAGACGCAC |
| 934 | GCATGATTAGCATAGACGGA |
| 935 | CCAGCAATAGCAATCACGGG |
| 936 | ATTGCACATTCAACTGACGC |
| 937 | TGGCATTTACTTAGTGCGAC |
| 938 | GAAGCCATATCAATGCTCAC |
| 939 | GCGAGCAATTTCATGCCACT |
| 940 | GGCCCAAGTTTGTGAGATGA |
| 941 | GGGCATAATGGTTGATACTC |
| 942 | TTGGTGCATGGATCTCTCCC |
| 943 | TTTAGGGCAGGTTAGCTTCC |
| 944 | TTATCCGGCTAGAGTGCGTC |
| 945 | TGATGACCTGTTAGCAGTAC |
| 946 | GGACCATGTGCTACGCAAAT |
| 947 | GTGAGCAGATTCAGCCAGAC |
| 948 | GAGAGACCATGCAGCCGATA |
| 949 | GCGTCGTCAATGTTGCCACT |
| 950 | GGGTTAATCCCTGCCACGTA |
| 951 | GTGCTGACATTCGCGCCATT |
| 952 | GCCTGTAATCGTGGGCACAT |
| 953 | AGCGCGTGAAATGCACATAC |
| 954 | AGCGTCTGAAATGCTATCAC |
| 955 | AGTGCGCGAAATGTTCTACA |
| 956 | CGTCGCCAATATGATCGAAT |
| 957 | CGCCACAAGTTCGAGCGATA |
| 958 | GCCCTACAGCGTGAGCTATA |
| 959 | TGTCAGTGATCCGGGACTAT |
| 960 | GTTATCGCACCTGAGGCGTA |
| 961 | GTTGTGACCTCTGAGCACGT |
| 962 | GTTTCACGCTATGCGAGCCA |
| 963 | GTTTACCGCTCTCCAGGGAT |
| 964 | TGCGTACCTCCTGCATGGTT |
| 965 | TGACTACCGTGTCGCATACG |
| 966 | TGGACTACGTGTCTCGATAG |
| 967 | TAGTGATACTGACTCATGGC |
| 968 | CGTCTGATACAGCCCAGTGT |
| 969 | GCCGTATCACGACGCTAGAT |
| 970 | AGCTCGATACAACGCTAGAG |
| 971 | ATCTACTTAACGCGCTACAG |
| 972 | GACATCGTACCACTGCGTAG |
| 973 | GACTCGTGACCACTCTGTAG |
| 974 | GACTCGGACCATATCTACGG |
| 975 | CACTACGCAAGACTATGTAC |
| 976 | CGAGTCTCACAGCAATCTAG |
| 977 | CGATCTAGCACGCAATATAC |
| 978 | GACCAGCGACGACAGTAGAT |
| 979 | CGTAGACAGCCACGCAGTTA |
| 980 | CGTATGCTACCACCGATTAT |
| 981 | CGTGCGATACCAGCGTAGAT |
| 982 | CTCCGTACAGCAGGCAGTAT |
| 983 | CTCGTCGTACAGCGATCAGT |
| 984 | CTACAGATACGTCGAGAGAG |
| 985 | CTACGCGACACGCATGAGAT |
| 986 | TAGACGCTCGCACGGTAGTA |
| 987 | GCCGCTAGACGACGGTATAT |
| 988 | GTATCACTAGGACGAGGTAT |
| 989 | GTACTCACAGTGCGAGAGCT |
| 990 | CGACTACACAGCTCAGGATA |
| 991 | CACCGACAACTCGTAGAGAG |
| 992 | CGACCCACACTAGGAGAGAT |
| 993 | ACGCGCACAACAGGAGACTT |
| 994 | AGTACCACAACTCAGACGTG |
| 995 | AGTACAGCAACGCAGAGCCT |
| 996 | GTCAGCGACCGTCAGCTATT |
| 997 | GTCAGGCACTAGGAGCTATC |
| 998 | TGTCGGTCACTCCTGGACTA |
| 999 | TCGGTTCACGTCCGCATGTA |
| 1000 | TCGTTTACCTGTCGCGCTGA |
| 1001 | TGTGTCTCACTTCCGCGAGT |

TABLE I-continued

| Seq. Id | 3' to 5' sequence |
|---|---|
| 1002 | TCTGAGCACTCTCTCGTAGG |
| 1003 | GTTGATGACTCGCCACACGT |
| 1004 | CTGAGATCACAGCAGACTAG |
| 1005 | TTAGACTCCTCGCCGGTAGA |
| 1006 | TATAGCTCCTAGCAGGCGTA |
| 1007 | TATGCTCCACGTCTAGTGAG |
| 1008 | CTCTATCACCAGCGATGAGA |
| 1009 | CGCTCCAGACAGCATATAGA |
| 1010 | ACATACCGAAAGCTCTAGCG |
| 1011 | ACATCGCTAAAGCACATCGG |
| 1012 | ATATCGCGCAATCAACGCTA |
| 1013 | CGATGCGCCACTCAAGGTAT |
| 1014 | TATGCCGACGGTCAGGCTAA |
| 1015 | TATCGCCACGTCCGGTGATT |
| 1016 | TCTCGCTCACTGCGTATGAT |
| 1017 | TATCCGTCACTCCGTAGAGG |
| 1018 | TATCGACTATCCCTGAGACG |
| 1019 | GTATAGACCTCTCAGACGCG |
| 1020 | CTATCGTAATATCAGTCCGC |
| 1021 | CGATGACAATTAGGTACACG |
| 1022 | GAGCATAATGACGTAGACCG |
| 1023 | CGACAATACTTGACAGCACG |
| 1024 | CGATGATAATAGAGTAGCCG |
| 1025 | CTATGATTAAGTCGTAGCCC |
| 1026 | AGGTGAATAACGCATACGCC |
| 1027 | GAGTGAGTAATGCTACGTCA |
| 1028 | GATCGACGAATGTTAGAGAC |
| 1029 | GACTCACGAATGCGGAGACT |
| 1030 | GACCGTCAATCGCGTCAGAT |
| 1031 | TACCCGCATCGACGGAGTTT |
| 1032 | GTCAGCGCACTCCTGGTTTA |
| 1033 | TCAGGCCCACGTAGCGTTAT |
| 1034 | TTCGCGCTATCCATGCGTGA |
| 1035 | TGCTGATACTCGGCTGCATC |
| 1036 | TGAGTAGCATCGGTGACTTC |
| 1037 | TTGTATCACTGTGCTGCCCA |
| 1038 | TTTAGTGAGTATGCTCGCGG |
| 1039 | TTACGTTTATATGGCCGAGG |
| 1040 | TGAGATCACGTTCGCCGAGT |
| 1041 | GTATCATTAGCTCCGCAGAG |
| 1042 | TATCATGTAGACTCGGAGGC |
| 1043 | GTATGCTTAGATATGCAGCG |
| 1044 | TTGTAGTTAGCTCTGCACGG |
| 1045 | ATATCGTTAAGCCATACGCC |
| 1046 | ATTGTGATAACGCTCTCGAC |
| 1047 | ATTCGTCCAACGCGGTCGAT |
| 1048 | ATATGCACAACGCGCAATCG |
| 1049 | TTAGCTCTATCGCAGTCCGA |
| 1050 | ATTAGCTGAACGCCTCGCAA |
| 1051 | ATTATCTCAACGGAGGAGCA |
| 1052 | ATGTTGCTAACGGACGGACA |
| 1053 | ATGTGTTCAACGGAGACAGA |
| 1054 | CTCTTTCTAAGTGAGTCGAG |
| 1055 | CTGCTTGAAGTCGTCTCACG |
| 1056 | CTGCGTTGAAGTGGCTTACT |
| 1057 | GTGCGTTCACATGGCCGTAT |
| 1058 | GTAGCCGCACCTGACTGTAT |
| 1059 | GTAGCGCCACCTGACGTTAT |
| 1060 | GGCGCGTCACATGATACATT |
| 1061 | GGTTGCTACGATGACTCAGT |
| 1062 | GAAGGCCCGTACACTCTATA |
| 1063 | GACAGGGCACACGACTCTAT |
| 1064 | TGCGCGGCACTCGTTCTATA |
| 1065 | GCGGTTGCACTCGTAGCATA |
| 1066 | GAGGCGTGACCAGTCCATAT |
| 1067 | GGACGCTCACCAGTGCTTAT |
| 1068 | AGTGTCCAACCAGACCAGAG |
| 1069 | AGTGCCATACAAGCGCATAG |
| 1070 | GTAGCCTTACATTGGCAGAG |
| 1071 | GTCGCCGCACATTCGGTTAT |
| 1072 | GTTGAGTCAGATTAGCAGTC |
| 1073 | TCGTAGGGACTGCGCTCATA |
| 1074 | CTCAGATGACAGCGACGCAT |
| 1075 | CTCTGAGGACAGCCGAATCT |
| 1076 | CTAGGATGACAGCCAGACAC |
| 1077 | CGTGAATTACATCAGACAGC |
| 1078 | CTGATTATAGCTCATACGCC |

TABLE I-continued

| Seq. Id | 3' to 5' sequence |
|---|---|
| 1079 | CTAATATGATGACAGTCCGC |
| 1080 | TACTTATGATGACTGCGGAC |
| 1081 | GAACTATGCTGACAGTACCG |
| 1082 | CGATTCTGACCACATACGAG |
| 1083 | CTAATCTGACCACGAGACGA |
| 1084 | CTGTATTGACATCAGACGAG |
| 1085 | CTTCTCAGACATCGGACGAG |
| 1086 | GCACTGTGAATTAGCGAGCA |
| 1087 | GCCTACGGAATTGGCAGACT |
| 1088 | GACCTGGAATTAGCACACGC |
| 1089 | GCCTGCGAATTAGCGGACAT |
| 1090 | GCGATGCTAATGATGTGTAC |
| 1091 | GCCCGTCTAATGAGTGGACA |
| 1092 | GCCTAGCTCATCAGACGGAA |
| 1093 | GCATGGACATCCTACGAGAA |
| 1094 | CGCCTGCCAAGCTGTGATAT |
| 1095 | GCCTGCGCCATCAGTAGATA |
| 1096 | GCACGGCCAATTACTCGATA |
| 1097 | GCAGCGAGACCATGTGATAC |
| 1098 | GCAGCAGCACACTGATCGTT |
| 1099 | GACCCAGCACATTAGCGAGA |
| 1100 | GCTCCTGCAATGTGCGGATA |
| 1101 | GCGCCTGAATTGTAGCACGT |
| 1102 | GCCACAGCATTGGAGAGAAT |
| 1103 | GCCAGGCTAATGGATAGTAA |
| 1104 | GCCCTGCGAATGAAAGACAT |
| 1105 | GCAGCGGGAATTAGATATAC |
| 1106 | GCAGGTGCAATGATTCTACC |
| 1107 | GACCGGGCAATCACTTCAGA |
| 1108 | GCCGGGCAATGCGTTCATAT |
| 1109 | CCCAGGGCAAGCGATCATAA |
| 1110 | GCCACAGGCAGGGCATATTA |
| 1111 | GCCTAATCCTGGGACACTGA |
| 1112 | TCGTCTCGATCTAGGCCATG |
| 1113 | GTGTCTCGACTCAGCCTATA |
| 1114 | GACGTAGTAATCATGTCTCC |
| 1115 | GACTTATACGTCATGCGACC |
| 1116 | ACGATGTAACACAGCGACCG |
| 1117 | AGTCGTGTAACCATGTGACA |
| 1118 | GTCGTGACAGTGATGTACTC |
| 1119 | GTGGAGTGACGTATCTCTAA |
| 1120 | TAGAGGTGACGTAGTCCACT |
| 1121 | GTCGTGCGAGATAGCTCTTA |
| 1122 | GTGTAGAGATATAGCATCGC |
| 1123 | TAGTCGTGAGATAGCGATTC |
| 1124 | CAGTGTGTACGAATACGAAG |
| 1125 | CGAGTGTCACATACCACATA |
| 1126 | CGTATAGCAGACAGCGCAAT |
| 1127 | GACATCGACGACAGGCCATA |
| 1128 | CGAAGCTCACGTAAGTCAAG |
| 1129 | TAGTGCTCACGTAGCCCAGT |
| 1130 | TGCCCACGGTGAGCTAGTTT |
| 1131 | TAGCTGCCAGGAGCGTTCTA |
| 1132 | TCGGCCTACGCTGTGCATTA |
| 1133 | TAGGGTACTGATGAGCACTC |
| 1134 | CTACGGGAAGGTTAGCACCA |
| 1135 | TGGTGATACCTGTGCGCCTA |
| 1136 | GATTAGATACCACTGCCACA |
| 1137 | GGAGTGATACCTCGATCCAC |
| 1138 | AGCTGACGAAATCTTCACAC |
| 1139 | GAGGAGATAATGGTCACTAC |
| 1140 | CACGGAATAATACATCCTCG |
| 1141 | ACAGCAACAAGTCGAGCCGT |
| 1142 | ACGGAGAGAAATCAGCCCTC |
| 1143 | CAAGAGATAATACGGCTGCC |
| 1144 | CAAGTCCTAAGACAGCTACG |
| 1145 | ATAAGCGCAAGACAGGCGTC |
| 1146 | ATCTGAGCACAACTAGGACG |
| 1147 | CACAGGCTAAGACAGGAGCT |
| 1148 | CATAGCGTAAGCCAAGCAGC |
| 1149 | CATAGTCTAAGCCACATCAG |
| 1150 | GACAGTACATGCCAATCAGC |
| 1151 | GCGGTAATCGGTGCATCAAA |
| 1152 | GGGAGTATAGCTGACCATCA |
| 1153 | GTAGGCAGACCTGATCCCTT |
| 1154 | GAGCCAGACCACGCTTGATT |
| 1155 | GGCGCATCACTAGCCAGATT |

TABLE I-continued

| Seq. Id | 3' to 5' sequence |
|---|---|
| 1156 | GGAGCTACATCCGCCAGTTT |
| 1157 | GGAGTCTACCCAGGGCATTT |
| 1158 | CGCGCTCTACACGATGGATA |
| 1159 | CGTGCCACACCTTGGAGTAT |
| 1160 | CGCGGCACACAGTTCAGTAT |
| 1161 | GCTCGTCCACAGTGCGTTAT |
| 1162 | GCTGACGCAGAGTCCAGTTA |
| 1163 | CCGTAGCGACAATCAGCTTA |
| 1164 | ACGCACCGAAAGTGAGCGAT |
| 1165 | ACGTCCTCAAAGTGCAGACA |
| 1166 | ACGCAGTCAAAGTCATATCC |
| 1167 | CAGAGTCTAAGATCACCACG |
| 1168 | CACTGTCTAAGATACACACG |
| 1169 | CAGCGTACAAGCTATACAGC |
| 1170 | CCGACGACAATGTACGACAG |
| 1171 | GACTAGCGAATCTAATGAGC |
| 1172 | CGTCGAGCAATATGAATGAC |
| 1173 | CTGTCGCGCACTTCATAGGA |
| 1174 | CCGCGACCACGATAGAGAAT |
| 1175 | GGCACACACGTCTCGGATAA |
| 1176 | GGCAGACGACGTTGCATACA |
| 1177 | CGTGGGACACAGTCGATCAT |
| 1178 | AGTGCGAGAACATCGTGTAA |
| 1179 | GGCAGCACAGCTTGTACGAT |
| 1180 | GACCATTGAATATGTCGAGC |
| 1181 | GTACGCATATTTAGCCAGCA |
| 1182 | GGCAATCTGTTCACGACCAA |
| 1183 | GCTGACTAATTGCTAGACAG |
| 1184 | GGTGTCTAATTGTATGCACG |
| 1185 | GTTGACACATTGTTAGCAGC |
| 1186 | TTAAGAGATTAGTCTGCCGC |
| 1187 | TCACGTAATTTGTTAGCCGC |
| 1188 | TGAGTGATAGCTCGGATCTC |
| 1189 | ATGATGATAACTACGTGCCC |
| 1190 | ATGCGAATAACTATGACGCC |
| 1191 | ATGGAGATAACTATGCACCC |
| 1192 | TCGTTGCGACCTATGCGTAG |
| 1193 | TAGTTCGCACCTACTGCTAG |
| 1194 | ATACGTGCAACCACTGCTAA |
| 1195 | ATGTCGATAACCTCTGCTAC |
| 1196 | ATCTAGTCAACCTGAGCTAC |
| 1197 | AGTATAGCAACCTCAACTCG |
| 1198 | AAGACACTAAACTCTGCTCG |
| 1199 | ACGATAATAACAGCTCCTCG |
| 1200 | ATAGATATAACTGACGCGCC |
| 1201 | ACTGTAATAACCAAGCCTCG |
| 1202 | ACTGATAGAACCACAGCGCG |
| 1203 | ATGGCGACACACATACAGCG |
| 1204 | ACGGCGAGAAATACGATGCC |
| 1205 | GACGCGAGATCAATGTAGTA |
| 1206 | CGAGAGTAATCAATCATCCG |
| 1207 | CGAGCAATACATACATCTGC |
| 1208 | CAACATAGTTACACACGCTG |
| 1209 | CAGCTTATAGAGACACACTC |
| 1210 | CCATAGAAGTAGACACCTCG |
| 1211 | CTCAGAGACATGACACTCGA |
| 1212 | ATCAGGTCAACTAATCACCG |
| 1213 | AGCGCAGTAAATAGCTTAGC |
| 1214 | ACTCCACGAAACATGATTGC |
| 1215 | CTCAATATAGACACGATGCC |
| 1216 | CGCATTAGAGACAGATCGAG |
| 1217 | CGCACATGACATAGAGCACG |
| 1218 | CGCACATTAGACAGAGAGGC |
| 1219 | CTAGACTAATGCAGAGAGCG |
| 1220 | GCGTATAGATGCAGAGATCC |
| 1221 | TCACTAGCGTGGAATAGAGC |
| 1222 | CAGACTGAACTCAATGTACC |
| 1223 | CACGATGAACTAGATGTACC |
| 1224 | CGAATGATAAGTATGACGGC |
| 1225 | CGAGATGCAAGTATAGTACC |
| 1226 | GGATAGCGAGATATAGACCC |
| 1227 | GCATAGCACGATGGACGATC |
| 1228 | CTCACAGGACATGCAATCGG |
| 1229 | TATACATGCTTCGATCACCG |
| 1230 | ATATCAATAACTGCGACGCC |
| 1231 | AATACGAAAGATGCGGCCCG |
| 1232 | ACAGATACAAATGTCGCCCG |

TABLE I-continued

| Seq. Id | 3' to 5' sequence |
|---|---|
| 1233 | ACGAATAGAAATGTGGCCGC |
| 1234 | ACATTACTAAAGGTGCGACC |
| 1235 | AGATTAGTAAATGCTGCGCC |
| 1236 | ACTATGATAACAGCAGCCCG |
| 1237 | ATATGAATAACTCCAGCGCC |
| 1238 | AGACTGAAATCTACAGCCCG |
| 1239 | GTACTGATAATTGGATCGCC |
| 1240 | CCAGAACGGTTGCAGACACT |
| 1241 | GCAATAGTTGGACCCAGGCT |
| 1242 | GGAATAGGTGGACTCACTCA |
| 1243 | GCACAAGTTTCGCGCATCGA |
| 1244 | GCGGAATCTGTGCAGCATCT |
| 1245 | GCGAGAATATGGTGACATCT |
| 1246 | GCGGTCAATTAGTGGACTCC |
| 1247 | CTCCTACAATGGTGACACTG |
| 1248 | CTATTACAATGGTATGCCCG |
| 1249 | AATCATACAAAGTGTGCCGC |
| 1250 | CATGATCTAAGAGTGTAGCC |
| 1251 | CAAGAAGTAAGATGCGTGCC |
| 1252 | CATGTGATAAGATGTGGACC |
| 1253 | AACTTAGCAAACTTAGCGCC |
| 1254 | TCTTCGATATGATAGCGTCG |
| 1255 | GACGTTAATTGATGAGACGC |
| 1256 | GCGTGAAGTTGTTAGCACAT |
| 1257 | GCCGATACATGCTGCACGAT |
| 1258 | CGCCGATTAAGCTGCGACAT |
| 1259 | CGTCATTTAAGTTAGCGCAC |
| 1260 | CTCCATCTAAGGTGCGATAC |
| 1261 | CGCTTATCAAGGTGCAGACC |
| 1262 | GATGACTCAATGTGACTCAG |
| 1263 | CGCTAGTGACAATTATGTGC |
| 1264 | GCTAGGTGACAGTATGCTAT |
| 1265 | GCTGTGCTACGACGTTGACA |
| 1266 | GCTAGAGTAGACCGATGCCA |
| 1267 | GTATATCGAGATCATAGGCG |
| 1268 | GTCTTGGACTATACGAGCGC |
| 1269 | TACTTGTAGATAGCGAGCGA |
| 1270 | GTACTCTGACATGATTCGCA |
| 1271 | TATACTGACCTTATCGGCAC |

TABLE I-continued

| Seq. Id | 3' to 5' sequence |
|---|---|
| 1272 | TCGTCTTGAGATATGTGGAC |
| 1273 | TCATGTTACGGTATGCGAGA |
| 1274 | TCATCTGCACGTATCGTCAA |
| 1275 | GCGACTGGACAGATTGCATA |
| 1276 | CGGGCGCGAAGTATTCACAT |
| 1277 | GTGTGGGCACGTATTCCATA |
| 1278 | TCCGGGCACGGTGTCATATA |
| 1279 | TGGGCGCTACTGGCTCTTAA |
| 1280 | TGCGCCGCCAGTCTGTTATA |
| 1281 | TGGCCGTTAGAGTCTGCACT |
| 1282 | ATGGGCGCAACCCTGTCATA |
| 1283 | CAGCCCTGAAGACTGCGATA |
| 1284 | CGCCGCTCAAGGCTATGATA |
| 1285 | CGCTCCTGAAGGGTAGTTAA |
| 1286 | GGCCCGACAGGTGCTATTAT |
| 1287 | GGATAGGCAGATGCACTTAT |
| 1288 | GGACAGACGTTGACCAGCTA |
| 1289 | GTAGCGACATTGAGTTAGCA |
| 1290 | GACTACGAATTGAGCATACG |
| 1291 | CTACACTAATTGCAGCAGCA |
| 1292 | CGTACCCGAATGCAGCAGAA |
| 1293 | GACGCCTAATGACGCTGAAA |
| 1294 | TAGCTTGTACTGCGACTGAC |
| 1295 | GATACTCTAATGCCATCGAC |
| 1296 | CGGCGTACAATGCCATAGAA |
| 1297 | CGGATACGAAGGCTATGCAA |
| 1298 | ACGGATCGAAAGGTATAGCC |
| 1299 | ACGGCGCGAAAAGCGTCATAA |
| 1300 | CGTGAGGGAATACGTCATCA |
| 1301 | CACAGTGGAAGACGCATCAC |
| 1302 | GAGGTGACATGACGTACATC |
| 1303 | GAGTAGCGAATGCTCAGCCA |
| 1304 | TATAGCACAGTGTCCAGCAA |
| 1305 | CGTATGTCAAGGGCCTGATA |
| 1306 | CGAGACGCAAGGGATTTACA |
| 1307 | GAGACGCAATGTGAATTACG |
| 1308 | GATCGCACAGGAGCGTATCA |
| 1309 | TGCCCAGAGCGTATGAGCAA |

TABLE I-continued

| Seq. Id | 3' to 5' sequence |
|---|---|
| 1310 | TGAGGGCGAGCTATCTATCA |
| 1311 | TTGTGGCTAGGTATCGCTAC |
| 1312 | TGGTTAGCAGGTATGATCCT |
| 1313 | CTCACTGCAAGGATGGGACT |
| 1314 | TCCTGTAGATCCCTATGCGG |
| 1315 | TCGTTGTCAGCATATTGAGC |
| 1316 | ATCATGTGAACCTATTGGCC |
| 1317 | TACACTGGGACCTATGGGCA |
| 1318 | TACCTGGGAGCATAGCTGAC |
| 1319 | TAGCCCGCAGCATAGGGTAT |
| 1320 | GAGCCTCAATGCTACGGAAG |
| 1321 | GATGTTCAATGCTGGCCGAA |
| 1322 | GACTTGTGAATATCTGTGCC |
| 1323 | GCCGCCGAATTATTGAGCAA |
| 1324 | TGGACTGATTGATAGGCAAC |
| 1325 | TGGCAGATCGGTGTATTCAA |
| 1326 | TATGCGTAATGGGTGTTCCA |
| 1327 | TTAGGTCGATTGATAGTCGC |
| 1328 | TCTGCTTTACTGCGTAGCCA |
| 1329 | TTGACGAGTTTGCAGTGCTC |
| 1330 | CTTGATTAAGTGCTGTACGC |
| 1331 | CTCGGATCAAGGCTTACCGT |
| 1332 | CCGGGCTCAACGCTTTGTAA |
| 1333 | TGTCGCCCAGCTCATGTGTT |
| 1334 | CTGGACCCACAGCTATGGAT |
| 1335 | CACGGGCCAAGAGATATACC |
| 1336 | CGCCCGCCAAGTGATGTATA |
| 1337 | CGCCAGCCACATGGATAGAT |
| 1338 | GCCCGGATACATGCGATTAG |
| 1339 | GCTGGCCTACATCCGTATGA |
| 1340 | AGATGGCGAAATCCGTATAG |
| 1341 | GCAGGGACATTACGATCAGT |
| 1342 | AGCAGGTGAAATCGTACTAC |
| 1343 | GCAGGTCAATCTCTGTACGA |
| 1344 | GCATTGTAAGTTCGGTCAAG |
| 1345 | GCACTGGTAATTCAGCTACG |
| 1346 | AGCATCATAACCCAAGCTGG |
| 1347 | ACCAGTCCAAAGCATAGTCG |
| 1348 | ATCATTTCAACGCAGTGACC |
| 1349 | TCAGCCCTATCGCAGGATGT |
| 1350 | GTCAGCACCAGCCGTGATTA |
| 1351 | GAATTACGCACCCAGCTTGA |
| 1352 | GAATGCGCCTACCAGCTATA |
| 1353 | GAATGGCGACAGCGTACATA |
| 1354 | GGATTGCCACGACTCACAAA |
| 1355 | GCTCATTGACACTGCGCTAT |
| 1356 | GAGCATGGACCACGGCTATA |
| 1357 | CAAATGGACAGACAGCCTGC |
| 1358 | CACTTTGAAGCACAATCACG |
| 1359 | GCTGTTGCAGGACGCATCTA |
| 1360 | TACCTGGCATGACGCGATAT |
| 1361 | TTCGTGGACTTGCGGATCTA |
| 1362 | TTCCTGCGATAGCGGCGTTT |
| 1363 | TTGATCTGATAGCGGGTCTC |
| 1364 | TTGATCGCATAGCGTCTGAC |
| 1365 | TTCGAGGCATGTGGATCTCC |
| 1366 | TTCAGCGGCTAGGCGATTTC |
| 1367 | TCCAGCAGATCGGCGAGTTT |
| 1368 | TTCAGCCGATCTGCCGATAT |
| 1369 | TTCTATCGCATGTCAGCCGT |
| 1370 | TGTAATGCCTGCCAGCCGTA |
| 1371 | TAATTGCCTGCACAACTGGA |
| 1372 | TAATTCCATTGACGGCAGCG |
| 1373 | TTATTGCCATAGCGCGACGC |
| 1374 | ACAATTTCAAAGCCTGACCG |
| 1375 | ACAGGCCCAAAGCACTAGGT |
| 1376 | CGAATGCCAAGGCCAGCTAA |
| 1377 | GATGGTTCAATGCCTGGACA |
| 1378 | CTGGGCCAAGTTCTGAGACA |
| 1379 | CGTGGGCAATACAGTTGAAT |
| 1380 | GAGCTGCGAATCGGTATTAA |
| 1381 | GACCGGCGAATCGAGCATAA |
| 1382 | GACTTCGCAATCGGCACGTA |
| 1383 | GACGCGCCAATCGTGCTATA |
| 1384 | GATCGCTGAATCGTGCGTAA |
| 1385 | GATCACTGAATGCGACGTAA |
| 1386 | GATCGTGCAATGAGGTTACA |

TABLE I-continued

| Seq. Id | 3' to 5' sequence |
|---|---|
| 1387 | GAGGACTAATTGAGATGCAC |
| 1388 | GACCGATAATTCGATATGCC |
| 1389 | TAGCATTGATCCCATGTCAC |
| 1390 | TTGAGCTTATGCCAGTCGCG |
| 1391 | TGACGGCCTTGCATATCCGA |
| 1392 | GAACGCGCCTTACATCAAGA |
| 1393 | GAATACCAGTTACACTCCAG |
| 1394 | CAAGAACTGTTACACATCGC |
| 1395 | GACGAGAATGGACTACACGT |
| 1396 | TACAGACGCTTGCATAGATC |
| 1397 | TAACGACCTTAGCGACGGGT |
| 1398 | TAACGACGCTTTCCCAAGGA |
| 1399 | TTACCGCTGTTGAGCCCGTA |
| 1400 | TTCCATGTATCGAGCGTCAG |
| 1401 | TATACGCCCTTCAGATCGGG |
| 1402 | CTAAGCCTATGCAATATCGC |
| 1403 | CCAGCTATAAGCATATTGCC |
| 1404 | TACAGCATTGTCATGGACTC |
| 1405 | TAAGCTATTGGACATTGGGC |
| 1406 | TTAGCATCCTGTCATAGGGC |
| 1407 | TCTAGGAGCTTTCATAGCCA |
| 1408 | TCATCACGCTTTCCGAGGAT |
| 1409 | GCATACATTGGACGAGAGCT |
| 1410 | TCTAGCATTTAGCATGGTGC |
| 1411 | TTATGACTTGATCTGAGGCG |
| 1412 | TGTTCGCACTGGCTTAGCTC |
| 1413 | GAGTTGAATGCAGATAGCTC |
| 1414 | TGCAGGCTCGCAGATGCTAT |
| 1415 | TGCGAGGACTGTAGCTTAAT |
| 1416 | TGGGCACTCTCGCCTAGTTT |
| 1417 | TGAAGCGCCTCGACTAGGTT |
| 1418 | TCATCGGCACTGATAGCTCA |
| 1419 | TCATCAGGCATGGAGCCAGT |
| 1420 | TAATCAGCGTTACGTCCGCA |
| 1421 | GAATGTGACGCAAGTCTGAC |
| 1422 | AGATTTGCACAGATAACGCG |
| 1423 | GATTACTGACCAGCATCGAG |
| 1424 | AACTATCGAAACCGCCAGGG |
| 1425 | ATAATACAAGAGTCGCGCCG |
| 1426 | ATAATCATAACCTCGACGCG |
| 1427 | ATTATCATACAAGGCAGGCG |
| 1428 | AATATCGGATCAGCAGGTCA |
| 1429 | TAATTTCGCTACGCAGGGAG |
| 1430 | TAATCCTGTTACGCGGAGGC |
| 1431 | CTTTAGCTCCACGCAGTGTG |
| 1432 | TTCTAGCCGTCCGCAGTTTG |
| 1433 | GTCATGCGAGCAGCAGTCTT |
| 1434 | GGCGTTCGAGCAGTCATCTT |
| 1435 | TACCGCCAGTCAGCGAGTTA |
| 1436 | TACCGCCTAGCAGCATTGGT |
| 1437 | TACCGCACTGCATGTCAGGT |
| 1438 | TGTCTCGATGCAGGTCTAGT |
| 1439 | GCCGCATGACGAGGATATAC |
| 1440 | TACCGCGAGGCAGGATTCTT |
| 1441 | TACAGCAGTGCAGGGCCTTA |
| 1442 | GCAGCTAGAGCAGAGTATCA |
| 1443 | GACAGCAGATCAGAGACTCC |
| 1444 | TAAGCACGTTTAGAGCTGAC |
| 1445 | TAACCGTGTGCAGATCGGAT |
| 1446 | TACTGCGGACCTGGATCTAC |
| 1447 | TCAGGGCTACTCGATTGGAA |
| 1448 | TCCGCAGACTTAGCGTTACG |
| 1449 | TGAGCAGCCTACGTTACTAG |
| 1450 | TGCGTCAGATGCGTATATGC |
| 1451 | TCGTCCAGATGCGGAGTTCA |
| 1452 | TCGGCTATATGCCAGATCCT |
| 1453 | AAGGACAAAGAGCGCGTCTC |
| 1454 | TAGCACCGATGGCGAGCTTA |
| 1455 | TGTCCACGGTGCCGCAATAT |
| 1456 | TGGTCCGACTGCTGCTACTA |
| 1457 | TGTGCCGACTGCCGTCTTAT |
| 1458 | TTCGCAGTATGGATCGGTAT |
| 1459 | TTACGCAGTTGCATGGAGCT |
| 1460 | TTCTGATTAGCTGCGGACGC |
| 1461 | TGGTTATACTTTGCGAGAGC |
| 1462 | TTTGTTAGCTTCGGGCAGCC |
| 1463 | TTGGTCTGATCCGGGCATAC |

TABLE I-continued

| Seq. Id | 3' to 5' sequence |
|---------|-------------------|
| 1464 | TGCTTGGACTCCGGCGATTA |
| 1465 | CTGCTTGGACCAGCCAGTTA |
| 1466 | AAGCTGGGAAACGCACACCT |
| 1467 | AAGCGGGCAAACGATATGCT |
| 1468 | AAATGCCGAAACCATCTCGT |
| 1469 | CCATTCGGAAGCGACTCGAT |
| 1470 | TACATGGGCTGAGAACGCAA |
| 1471 | TATTGGGCACGAGCGCCTAT |
| 1472 | CATCCGGGAAGAGTAGCACA |
| 1473 | ATTTCATGCACATAGCACGC |
| 1474 | ATTGCAGCACAAGCCAGACT |
| 1475 | TTGCTAGGCTCAGTCCCGAT |
| 1476 | TTGGCGAGCTGCGTTCTCAT |
| 1477 | TCCCAGAGATGCGACTGCTA |
| 1478 | TTCGCTGGATCGGCATGTCT |
| 1479 | TTGCTCCTAGCTCGCGTGAT |
| 1480 | TTGCTGCTAGTCCAGTAGGC |
| 1481 | CATTAAGCAGTCGAGAGACC |
| 1482 | CGTTAATGCAGCGAGAATCA |
| 1483 | CGCAAGCTCAGCAGAATTAC |
| 1484 | CCATGTCGAAGCATTCATAC |
| 1485 | CTGAATGTAATCATCGTGCC |
| 1486 | CTTAGATGAATCACTGCCAC |
| 1487 | CTTCACGGAATCTAGGCACA |
| 1488 | CACTCTTGAAGCTAAGCACA |
| 1489 | CCTCTAAGCATGTTGACACA |
| 1490 | CATGCCGGAAGATGCGTACA |
| 1491 | CAGGCAGCAAGATGTACGAC |
| 1492 | CAGTGGGCAAGATAAGATTC |
| 1493 | CCGTGCCCAAGCTAGTGATA |
| 1494 | GATCGGGCAATCTGCGTACT |
| 1495 | TTCAGTGCATTATAGTGCGG |
| 1496 | TTATCTGCATGAGTAGGTCG |
| 1497 | TCGATAATCTTTGTAGCGCG |
| 1498 | TCTTACAGCTTTGCAGGGAG |
| 1499 | TCCTACATTTGCCACGGGAG |
| 1500 | TCTTCATCAGTGAGGCGCGA |
| 1501 | TTTCTAGGATGTATGCGAGC |
| 1502 | TATCCAGCATTACTGCGAGA |
| 1503 | TTATTCTCAGCACGCACGGA |
| 1504 | TGATTCGCACTCGCGGCTAA |
| 1505 | TTTGTATGAGTCGCTCCGAA |
| 1506 | TTCCGATCAGTCGATGCAAA |
| 1507 | GATCGTCAATCTGATGCACC |
| 1508 | AGATCGCTAAATGAGGACCC |
| 1509 | GATGCTATAATCGTATGGCC |
| 1510 | AGGAGCGTAAATTATCAGCC |
| 1511 | GGGCGATGACTATATCTGAA |
| 1512 | CTGGATTGACACTAGCATAC |
| 1513 | CTGCGGATACCATAGACAAC |
| 1514 | ACTGCAATAACATATCCGCG |
| 1515 | AATGACATAAAGTGCTGCCC |
| 1516 | ACATGCAGAAAGTAGTCCGC |
| 1517 | ACAGGCGAACAATGTACCCG |
| 1518 | ACCAGCACAAAGTCTACTGT |
| 1519 | AGAGAGCCAAATGACTGTCC |
| 1520 | TAGTGCATAATTGCTTGCCC |
| 1521 | TGAGCATATAGTATTCGGGC |
| 1522 | TGAGCGTTAGAGCTTGATCC |
| 1523 | TAGGCGCTAGGACTCGTTAT |
| 1524 | TATGGCCGACGATGTGTCAC |
| 1525 | TATGGCTGACGTAGCGCACT |
| 1526 | TCTCGGTTACTGAGTGGACT |
| 1527 | ATAACGGGACAGAAGCTGCT |
| 1528 | ATAGAACTCAATAGCCGCTC |
| 1529 | CATAATACACATACGCTGCG |
| 1530 | CAGTACGCAAGCAGATAGCC |
| 1531 | CAGACGCGAAGATAAGTTCC |
| 1532 | CAGCCAAGATAGCATACTCG |
| 1533 | TCCCATAGATAGCTCGCTGG |
| 1534 | TTCGCATGAGTGCTGAGTAC |
| 1535 | TTCCATATACTGGTCGGCAG |
| 1536 | TTTATGATATGCGTCGCGGA |
| 1537 | TTTCTTATATGCGCGAGCGG |
| 1538 | TGTTGCATATTAGCGGCTCG |
| 1539 | TATATGACATCTCTTGCCCG |
| 1540 | TTGTCACATTTGCGCTCCGA |

TABLE I-continued

| Seq. Id | 3' to 5' sequence |
|---------|-------------------|
| 1541 | GCATCCGAATTGCGACGACT |
| 1542 | GGATCTGAATTGCGCGACCA |
| 1543 | GGCTATGAATTTCGCATCAC |
| 1544 | GGATATGCAATTTGTAGCCC |
| 1545 | CAGCGTATAGCAAGATGGAT |
| 1546 | CGAGCGATAATCAAGTCGAG |
| 1547 | CGCGGATGACACATACTCAG |
| 1548 | CGACGAGCACCAATTCGAGA |
| 1549 | CCGTAGTGACCAATGCAGAC |
| 1550 | GCGATATACATCATTCGGAC |
| 1551 | GACAGTCTAATCACTCGTAC |
| 1552 | GCAGTTATACTAAGGTGTGC |
| 1553 | GCAGTAGTAATGAGTGTCAC |
| 1554 | GCAATGTAGTCGAAGTGTCT |
| 1555 | GCATATAGATACCATTCGCG |
| 1556 | CGAATACTAGACACATTGCG |
| 1557 | CAACTACAGTACACAGCGTG |
| 1558 | AGACACAGAACTACCGCGTG |
| 1559 | ATAGCACAACGTAGACGCCG |
| 1560 | ATACAGTCAACTACATCGCG |
| 1561 | AGTACAACCTAGAATCCGGC |
| 1562 | GAAGACTACTAGATACGCGC |
| 1563 | CGATAATACTACAGACTCCG |
| 1564 | CCGTGCGTACACATAGATCA |
| 1565 | CGTGAGCGACACATGATCCT |
| 1566 | CTGTAGTGACATATAGAGCG |
| 1567 | ATGTCGTCACACAGAATACG |
| 1568 | ATGCTACGAACTACCAATCG |
| 1569 | ATGATAACGTACACACCTGC |
| 1570 | TCGGTCTACGTCTGCTCAGT |
| 1571 | GGCTCACGATCCACTGGTTA |
| 1572 | TGCCTGATACCTTGGATGAC |
| 1573 | GGCCGTGAATTATCATAGAC |
| 1574 | GGCTTGGACGCATTGATAAC |
| 1575 | CCCATCGAAGCATGTGTAAA |
| 1576 | CGGCATCGAAGGCGTTCATA |
| 1577 | GCCAGTTGACCACTTCTGAG |
| 1578 | TCGCATTAGCCATGTGGAGC |
| 1579 | GCAATCTAGTCTAATGGCGC |
| 1580 | CTAAGATGTTCTAATCGCCC |
| 1581 | CCAATAGTAAGTAATGGGCC |
| 1582 | TCATTATACTCTGATGGCCC |
| 1583 | ATGCTAATAACTGATCGCCC |
| 1584 | AGTGTCAACCATGATGAACC |
| 1585 | AGAGCATAACATCATGGCCC |
| 1586 | AGAATCTAACAGCGATGCCG |
| 1587 | ATTTAGACAAGTCGATGGCC |
| 1588 | ATATTAAGAAGTAGGCGGCC |
| 1589 | CATATCAGAATACGATGGCC |
| 1590 | GATATACAGGATTATGGCGC |
| 1591 | CATAAATTGGTTCACACCGC |
| 1592 | GAAACTCCAATTCAGCGGAC |
| 1593 | GAACAATGAATTTAGCGGCC |
| 1594 | TTCCATTAGATGTGATGCCC |
| 1595 | TATCATATCATCTGAGGCCC |
| 1596 | ATCAGAAGAACTGCACGTCC |
| 1597 | AGCACAAGAACTACGCGCTG |
| 1598 | AGCAAAGAACCATGCCGCGT |
| 1599 | TAAAGAGCAATGTGGCGTAC |
| 1600 | TTCAGGGCATTGAGCGTAAA |
| 1601 | TTAATGGGCTTGAGCGTATC |
| 1602 | TTAATGCGGTTGAGATCGAC |
| 1603 | GCAGGGATAGCAGATACATC |
| 1604 | TCAGGAGAGGCATCGCATCA |
| 1605 | TTATCTTAGGGATGCGGATC |
| 1606 | TGTGCTCTAGGTCATCCGAG |
| 1607 | TTGTATCTAGTGCGAGGCAA |
| 1608 | TATTATCTAGTATGCGCGGC |
| 1609 | TAGTTATCAGAGTGACTGCG |
| 1610 | GTTAGATCATAGTCACCGCG |
| 1611 | GTTAGTATAGATTGGCCGAC |
| 1612 | GTGTTTATACGTTGAGCACG |
| 1613 | TTATCTGTAGTCATCGAGGC |
| 1614 | TGATACTGAGTTAGCGAGCT |
| 1615 | GTGATCTCAGAGCGCAGCTT |
| 1616 | CAGATGTCAAGACGCGGACT |
| 1617 | CTGGTCAGACAGCGGAATCT |

TABLE I-continued

| Seq. Id | 3' to 5' sequence |
|---|---|
| 1618 | CGTGGCAGACAGCTAGATAT |
| 1619 | GTGCCGAGACTCCACTGTTA |
| 1620 | GCGGACAGCTCTCCTAGTAT |
| 1621 | ATGCACAACTATCAAGCCTG |
| 1622 | GTGCTTTACTAGCGGAGCCA |
| 1623 | TAAATATCGTATAGGCGGCG |
| 1624 | TAATTCTACTATACGCGGGC |
| 1625 | TAAATCGTATGTAGCAGCGC |
| 1626 | TCCTTCACTGTAGGCTAGGC |
| 1627 | TCAGTTATATGAGCCGACTC |
| 1628 | TCACGTATATTGACTCCGAC |
| 1629 | TCACCGTATTCGAGGCGACA |
| 1630 | TCGTACTGATTGACGGTGAT |
| 1631 | TCACAGCGGTCGAGGTTACT |
| 1632 | TTCACGCGGTCGCAGTATCT |
| 1633 | TACTTGACGTGACTGCATCG |
| 1634 | CGTCACAGAGGACAGCATAC |
| 1635 | TCACTAGAGCGTCGAGCTGT |
| 1636 | TCTACAGTGTGTCAGAGTGA |
| 1637 | CTACCTAATCGACAGCAGAG |
| 1638 | CACCGATAACTACAGCAGGG |
| 1639 | CAACGTCTAGGACAAGGCAG |
| 1640 | CACTAGCTCAGACAGACGAG |
| 1641 | GACTTTACAGTACGATCAGC |
| 1642 | GACACTGACTGACATCGAGA |
| 1643 | GAGACAGTCGAGCGATCAAT |
| 1644 | GCACTTGTACGTCCAGTCAG |
| 1645 | GTACACGGACTGCCAGCATA |
| 1646 | GTAATACGCTATCAGCAGAC |
| 1647 | CTAGATAGACATCACTCACG |
| 1648 | TAGACTCTCGATCAGCCGTA |
| 1649 | GACTTGCACGTACAGCCGAA |
| 1650 | CTTATGCGACACTAGCTCGA |
| 1651 | CTGATGCTACACTAGGCACA |
| 1652 | GCAGACGCACTATCATATAC |
| 1653 | GCAGTAGACACTTCTCACGA |
| 1654 | GCAGGTACACTGACCGACTA |
| 1655 | GCACATCACTGCACGATAGA |
| 1656 | GCAATGACTTCGACTCCAGA |
| 1657 | GACAAGTCATTTACAGGCGA |
| 1658 | GTAACTTGTTTGACAGTGCG |
| 1659 | GACACTGCATGGACAGCGTA |
| 1660 | GCAAGGACTGAGACATGCTT |
| 1661 | TGCGAGGTAGGTTATATCTC |
| 1662 | TGCGGAGAGTGATATACTTC |
| 1663 | GGCGTGAGAGCATTATATCT |
| 1664 | GTGCTGCGAGAGTATTATCT |
| 1665 | CCGCGTGTACCATATAATAC |
| 1666 | GAGCGTGGACGATATACACT |
| 1667 | GGCCGTGTACGATTATGACT |
| 1668 | GTAGCTTGACGATGCTGACT |
| 1669 | GTGCTGGTACTAGCTGCTCT |
| 1670 | TAATGTGACGTAGCCGACTC |
| 1671 | TACCGAGTGCGAGATGCTCA |
| 1672 | TACCGATGTCGATAGATCCA |
| 1673 | TCTCGTATAGGATGAGCAAC |
| 1674 | TCGTGAGTAGGATGCTTTCA |
| 1675 | TACGTGAGATGATGATCGCT |
| 1676 | TAGTCGGTAGCATGAGTCTA |
| 1677 | TAGTTCGAGGAGTAGTCATC |
| 1678 | TAGGTACAGTGCTGGATACT |
| 1679 | CTGCGTCAAGTGTGTAGAAT |
| 1680 | TGTGCGCTAGAGTCTGTCCT |
| 1681 | GGTGCGTCACGATCTCCTAT |
| 1682 | GTGTGGGTACTATGCCATCA |
| 1683 | GCTGATGTACTATCCATACC |
| 1684 | GCTAGATGACGATCAGGTAC |
| 1685 | GCATCTGTACGATCTCAGCA |
| 1686 | GCATCACGACGATTATCAGA |
| 1687 | GCTACGTTACCATGTGCAGA |
| 1688 | GCGTAGTTACCATGCTCACA |
| 1689 | GCGTGAGCACACTCTATCAG |
| 1690 | GCGTGCGAATTATGTATCAG |
| 1691 | TGTGGACACTTCTTATAGGC |
| 1692 | GCGTGAGTAATTTGACTACG |
| 1693 | AGGTGCGTACAAATGCTATG |
| 1694 | CGCAGCCGAAGTACGCTATA |

TABLE I-continued

| Seq. Id | 3' to 5' sequence |
|---|---|
| 1695 | CGACTGCTAAGGAGCGTACA |
| 1696 | CGATGTTGACAGACCGCACT |
| 1697 | CATGTAGAACTGACTCACAC |
| 1698 | CGAGCGGTAAGGATCTCACA |
| 1699 | ACACGCTGAAAGAGTACGCC |
| 1700 | GATCTGACAGGTAGCGATAC |
| 1701 | TCTCGTGCAGGTAGCTGTCA |
| 1702 | GCTCGGACAGATCGGTATCA |
| 1703 | GCCGGTATAGCTCGATATGC |
| 1704 | GCTGATACAGTTCGATAGAC |
| 1705 | CCTGACTAAGCTCGATAGAG |
| 1706 | GCTGATTACGATCTAGTAGC |
| 1707 | GAATGCTCACGACGAGTAGC |
| 1708 | GAACTGTCCTGACGAATGAG |
| 1709 | TTACTGTCTATGCGATCCGA |
| 1710 | GTTATGTCATCGCAGATTCC |
| 1711 | AGCTATATCAAGCAAGCGTC |
| 1712 | GCTTATACAGTGCAGTAGAG |
| 1713 | TTAAGTAGGTAGCTGGCCTC |
| 1714 | CAAGAGTAACTGCAAGGCCC |
| 1715 | CACTAAGACATGCACAGCGG |
| 1716 | CCTAGTGCAGACCACATGAT |
| 1717 | TCATGCACGTCGCCATAGGT |
| 1718 | TCTATACGCTCGTGCAAGGA |
| 1719 | TCAAGCCCGAGCCGAGTTTA |
| 1720 | TCAGCGCCAGCATTCATGGT |
| 1721 | CCATGCGGACCAAGTCGATA |
| 1722 | GAATGCCGAGCAATGATCCT |
| 1723 | GAATCGGCAGCAATACTGTC |
| 1724 | GAAGCCCAGCTAAGTGGTAT |
| 1725 | AACAGCCCAAACCGGATGGT |
| 1726 | TAAGCACCTTGCAGGATAGA |
| 1727 | TCAGCCCGATCCAGGGTATT |
| 1728 | TATGCGCCCAGGAGGCTTTA |
| 1729 | TGCCCAGCAGGTCGGATTAT |
| 1730 | TAGCTCGCATCACTGACGGA |
| 1731 | GGTCCCATACGAGTGGCATA |
| 1732 | ACTAACCCAACAGCGGAGGT |
| 1733 | GAGCTCTAAGCAGCACAGGA |
| 1734 | CAGGTCAAGCACATACCAGT |
| 1735 | CTGTGCAATCACGCCAGAGA |
| 1736 | CGGCGCAATAATGTCACAGA |
| 1737 | CGGGACATAATTGACACAGT |
| 1738 | AGGGCCAGACAATACACCGT |
| 1739 | GAGGTCACAATTTGCTACAC |
| 1740 | CAGGCACAAGATTGAGCACG |
| 1741 | ACAAGCGCAAATACTGCCGG |
| 1742 | ACAATCTGAAATAGCGCGGC |
| 1743 | ATCGACCCAAGAATAGCTCG |
| 1744 | ATAAGCACAAGCAGCGCGGT |
| 1745 | AACACTCCAAACCGAGGGTG |
| 1746 | AATCTATCAAAGCGACGGCC |
| 1747 | ATTCCCATAACGCGGAGGAC |
| 1748 | ATGCCAGCAACGCGCTAGAA |
| 1749 | ATGCTCACAAGCCACGAGAG |
| 1750 | ATGCTCCAACGATACATACG |
| 1751 | CAGCTTCAAGAGTACATACG |
| 1752 | CATGTCACAAGGGCATAGAC |
| 1753 | CATGGTCTAAGCGCTACAGA |
| 1754 | ACATGGCGAAAGCACCACGT |
| 1755 | CTTAGTTCAATGCACGCACG |
| 1756 | CGCCAGTTAATGCACGACAG |
| 1757 | CAGCAGCAACTCGACTAGAG |
| 1758 | CCGAAGTCAACTGCGCTAGA |
| 1759 | CCAGTGTCAATAAGAGACGT |
| 1760 | CCAGGCGAACTGATCGTAAA |
| 1761 | CCTGGTACAATCAGTAGCAA |
| 1762 | CTAGTGGCAATCATCAGACA |
| 1763 | CAATGCGAACTCACTAGACG |
| 1764 | CATGGCGTACCAATACCTAG |
| 1765 | AAGTGGCCCAAATAACTGCC |
| 1766 | CAAGGCCCAATACACAGGGT |
| 1767 | GATCTGCCAATGCCGCGATA |
| 1768 | GATTCGCCAATGTGCGCTAA |
| 1769 | GAGCCGCCAATGTCACTAGA |
| 1770 | GCGCCCGGAATGTCGTATAT |
| 1771 | GCCGCGCCAATGTTACGTTA |

TABLE I-continued

| Seq. Id | 3' to 5' sequence |
|---|---|
| 1772 | CTTCGCCCAATGCGTAGGAA |
| 1773 | TTCCCATGATCGCTGACGAG |
| 1774 | TTGCGGGAGCTGCCTCTTAA |
| 1775 | TTTCCCGGATAGCCGCTGTA |
| 1776 | TTTGCTGGAGTATGCGCTCA |
| 1777 | TTGTTCTCAGCTTGCGGCAG |
| 1778 | TGTGTGGCAGCTTAGTTCAC |
| 1779 | TCTTGGGTAGCATCTGTCAC |
| 1780 | TGGGTGTCAGCATCTACGCA |
| 1781 | TTGTGGCAGGTATGCTCCAA |
| 1782 | GTTGGGCACGGATCTCTATA |
| 1783 | GCCGAGGCACCATGCTTATA |
| 1784 | CGCTTGGGACAATCGCGTAT |
| 1785 | CCGCAGGGAACTTCAGCATA |
| 1786 | TGGAGGGCAGTCTCTCATAA |
| 1787 | CTGGGTGCAAGTTGTATCAA |
| 1788 | TGGCGCACATGGTGTCATAA |
| 1789 | TGGCATCACTGCTGCGGAAT |
| 1790 | TGCCAGTCATCCTAGCGTGT |
| 1791 | TCAGGCCAGGACTGCTTATC |
| 1792 | TTGGCATAGGAGTGCTTCTA |
| 1793 | TTTGCAGACGGTGTGCTATA |
| 1794 | TTGAGTCAGGGTGCCCAACT |
| 1795 | TTTAATATCGTTGCCCGAGC |
| 1796 | TCAGGATGATGAGCATGTAC |
| 1797 | CTCAAGCTGGGAGAACAGTA |
| 1798 | TCAGAAGTGGCTGGATCATA |
| 1799 | TCTCACATGGCTGGAGCATT |
| 1800 | CTACTGACACTGACCAGGGA |
| 1801 | TCGTAGCGACTCTCCAGGTT |
| 1802 | TACGTGTCACTATCGTCGAG |
| 1803 | TATAGTTACGTCTCGCACGC |
| 1804 | TACCGTTACGTCGCTCAGAG |
| 1805 | CACTACAACGTGCTACAGAG |
| 1806 | ATAGGTATAACGCAGTACGC |
| 1807 | ATAGCAGTAACGCATAGTCC |
| 1808 | ATAATCGTAACGCACCGACG |
| 1809 | ATGAGTGTAACGCCTCGACA |
| 1810 | ATGTAGCGAACGTACTCACA |

TABLE I-continued

| Seq. Id | 3' to 5' sequence |
|---|---|
| 1811 | ATCTAGCGAACGGAACTATC |
| 1812 | GTAGAGTCACGATGCAGTAC |
| 1813 | GTAGTATGACGTAGCAGTAC |
| 1814 | GTACGTCGAGCTAGATCGCT |
| 1815 | GAGTCTGTACGAGGTATCAT |
| 1816 | CGTGTCTTACAGCACTACAT |
| 1817 | CGTGCGCTACAGCAGTCATT |
| 1818 | GTAGCCTAGACGCAGTCGTA |
| 1819 | CGTCTCGCAAGTCGCGTATA |
| 1820 | AGTCGCGCACAGCAACGTAT |
| 1821 | ATCGAGGTAACGCCATATAC |
| 1822 | CTCGTGACATAGCCATAGAT |
| 1823 | ATGCGACGAACGCGGATATA |
| 1824 | CTAGACAGACTGCGACATAC |
| 1825 | TAGTCGTAGAGGCGCTATCA |
| 1826 | CTATCGAAGTCGCGTGAAAC |
| 1827 | CTGCGTATAGAGATCAATCC |
| 1828 | CCGCGTATAGACAGATATGA |
| 1829 | CTCGCTTACGACAGACTGGA |
| 1830 | CGCGCACGAGACATAGCTTA |
| 1831 | AGCGTCACACACAAGACTGG |
| 1832 | CCTACGAGACACATGACAGG |
| 1833 | CGCCGAGTACACATGCAGAT |
| 1834 | CCGTCGATACAGACTCAGAT |
| 1835 | CTCGTCAGACAGAGCGGATT |
| 1836 | GTCTCGCCACGTATCGGATT |
| 1837 | TCTCGCGTACTTAGGCATCA |
| 1838 | GTCTCGGTACGATGTAGCAA |
| 1839 | CGTGTGAGACAGTAGCATAT |
| 1840 | CGTGTAGCACAGCGACGATT |
| 1841 | GTGTAGCTCAGTCAGCATCA |
| 1842 | AGGTAGATAACGCTAGATCC |
| 1843 | CTGTAGAGACATCTGAATCC |
| 1844 | CTGATACGAAGTCTTATGCC |
| 1845 | CACGCTCGAAGACTAATGAC |
| 1846 | CACGCGATAAGACGTATAGC |
| 1847 | CTAGCAGTAAGTCTATGCAC |
| 1848 | CGTAGTTGAAGTCATCGACA |

TABLE I-continued

| Seq. Id | 3' to 5' sequence |
|---|---|
| 1849 | CGCGATAGAAGTCAGGACAT |
| 1850 | GACGGACGACATCTGAGCAT |
| 1851 | CATAGACGAATACAGCGGGC |
| 1852 | GATCACGACCTACTAGCAGG |
| 1853 | AGATATAACGAACTCTCGCG |
| 1854 | GATTATAGACTACTGAGGCC |
| 1855 | GAGTTTATACTACAGTGCCG |
| 1856 | GTCACTTACGCTCAGGCAGA |
| 1857 | TCGCTAGACGCTCTGGCATA |
| 1858 | GTACGCTCAGCACTGGCATT |
| 1859 | GACGCGCTAATACTGTCACA |
| 1860 | GCGTGCATACGACTGCCATA |
| 1861 | TGTAGTCTAGTGCATGGTCA |
| 1862 | GTATAGTCAGAGCTGGCACC |
| 1863 | CGTCAGTCAAGTATGGCACA |
| 1864 | ACGAGAGTAAATATGCTGCC |
| 1865 | ATAGAGCGAACGATAGTTGC |
| 1866 | ATCTGACTAACGATGATGCC |
| 1867 | GTTGTAGGACGTATGATCTC |
| 1868 | TTAGTCGAGTCTATGAGCCC |
| 1869 | CGACGATACAGTAATCTAGC |
| 1870 | CTGATACAGGCATAGACATC |
| 1871 | GGTATCAGAGCTAGGACTAT |
| 1872 | TCTATCTCAGCTACGGTCGA |
| 1873 | TCAGTTCGATCTACGGCTAG |
| 1874 | TCAGTGCGACTCAGGTACGA |
| 1875 | GTCACTGCACTCACGGTAGA |
| 1876 | TAACGAGTCTTCAGCACGTA |
| 1877 | GAAGTCGCCTACATAGCCTA |
| 1878 | GAAGTCCGTTACATGACCAT |
| 1879 | GTCAGAGGATCGAGCCACTT |
| 1880 | GCGAGACAGGTCAGTACAAT |
| 1881 | CGTCAGAAGGCTCGCACATA |
| 1882 | GCATACAGGTTACGACGCCT |
| 1883 | GCGATACAGGTTCAGAGATA |
| 1884 | GGACGCATAGCTCGCAGTAT |
| 1885 | GGACGCAGATCGCAGCATAT |
| 1886 | CGGCGTTAATCGCAGAGAAC |
| 1887 | CGCGTTCTAAGGCACGGATA |
| 1888 | CGCGTCGCAAGGCTGTTATA |
| 1889 | CGATACGCAAGGCTACGACA |
| 1890 | CATCTAAGGACACTACACTG |
| 1891 | TATCATCGAGGACTCAGTGC |
| 1892 | CACCGAGCAAGACTGACATG |
| 1893 | CGCACCCGAAGTCAGAGATA |
| 1894 | CGGCTAGGAAGTCAGCATAA |
| 1895 | ATGCTGCGAACGCGCCATAA |
| 1896 | CCGCGTGCAACGTGTTCATA |
| 1897 | GTCGCTGCATAGCATCTCAG |
| 1898 | GTCTGTGCATAGAGCGTCAT |
| 1899 | GTGGTGTCACTGATACGTCA |
| 1900 | GGTTAGCACTAGATCGCACT |
| 1901 | CGGGATCTACAGCATCATAG |
| 1902 | CTGGATATACAGCACTCACA |
| 1903 | ATGCGGCTAACGCCTCATAA |
| 1904 | TCGCGGCGCACTCTGTTATA |
| 1905 | TCGTGCTACTGCCACTGTAT |
| 1906 | TAGGACACTTCGCCACTATG |
| 1907 | TATGACAGTTCGCGCTACCG |
| 1908 | TCGCGCAGTTAGCCCTATGT |
| 1909 | TAGCCACCGTAGCTGATCGT |
| 1910 | GTAACCCGCTATCAGATCGA |
| 1911 | AGAGCGCAACACCACATTGT |
| 1912 | AGGCTAAGAACGCACACTCG |
| 1913 | GAGCCTAGACAGCTTCATAC |
| 1914 | GGCAGTTCACGACTCGACAT |
| 1915 | GGCCTTAGACGACTCGCATA |
| 1916 | GGTCGATCAGCACTGCATAC |
| 1917 | GGAGAGTCAGCACAGTCCTA |
| 1918 | GTATAGGCAGCACGGCTCAT |
| 1919 | GCACGGCGAGCACTATCTTA |
| 1920 | TAACGTCCTGCACGATCTGT |
| 1921 | GGACGCCTAGCACATCTGAT |
| 1922 | CGCTGCACATCACATGGATT |
| 1923 | GCACATCGAGCACATGCAGT |
| 1924 | GCACGACCAGCTCTTAGGAT |
| 1925 | GCCACCAGACAGATAGAGGT |

TABLE I-continued

| Seq. Id | 3' to 5' sequence |
|---|---|
| 1926 | CCCGACGCACGAATAGATAG |
| 1927 | CCCACGACAGATACATGAGT |
| 1928 | CTTCGCGCAGCTACATAGAT |
| 1929 | CGCTCCGAAGCTGCGATAAT |
| 1930 | CGCCGCGTAAGCAACAAATT |
| 1931 | CGACGCTCAAGGACTCATAA |
| 1932 | CGCACACTAAGGATCATTAC |
| 1933 | GACACGCAAGAAGCTGGCT |
| 1934 | GCAGGCATAGCAGAGGATCT |
| 1935 | GCTACGTCACTGAGCAGGAT |
| 1936 | GTACATCTCGTGAGCAGAGC |
| 1937 | CTACACGACTTGAGACGAAG |
| 1938 | CTAAGTACGTGCAAGCAAGG |
| 1939 | GACACGTAGGACAGCTATGC |
| 1940 | GACATAGTAGACATCTCACG |
| 1941 | GACAGCGTAGACATCGTCAG |
| 1942 | GACTATCACGACATTCAGCG |
| 1943 | GATCTACACGCTACCAGTGG |
| 1944 | GCTTACTACGGATAGATCAG |
| 1945 | GCGTATCTAATGGAGTAGCA |
| 1946 | GCGTATTTACAGTGAGCGAC |
| 1947 | GCGTATATCGAATTGAGTGC |
| 1948 | GCGTTCACAGAGTCCACGAT |
| 1949 | CGCGTATCAAGGTCACGACA |
| 1950 | GCTATTACAGTGTCAGAGAC |
| 1951 | CGTCAGATAAGGTGAGTTAC |
| 1952 | CGTCTGTGAAGGTCAGCTAA |
| 1953 | TATTAGCACTCGTCAGCAGC |
| 1954 | ATGTTATCAACGTCAGCGAC |
| 1955 | GGCATACTAGAGTCAGCGAT |
| 1956 | AGTGCGATACAATACGAGCG |
| 1957 | CAGCACACAGAGTACAGCGT |
| 1958 | CGTAGCATAAGGTCAGCACC |
| 1959 | GTCCATAGACGTTGATACCA |
| 1960 | GCTACGATAGATGAGCCACG |
| 1961 | CGGAGTACACCAGATCCAGA |
| 1962 | GAGCGTATAGGAGATGCAAC |
| 1963 | GACTGTAGAGAGACGATCCA |
| 1964 | CTAGTAGGAAGTGCGATCAA |
| 1965 | CGTAGAGGAAGTGATACTCA |
| 1966 | CGTATCGGAAGTGAGTATCA |
| 1967 | CTATGACGAAGTGAGAGTAC |
| 1968 | GTTCGTAGAGATGATCGTCA |
| 1969 | GTTCTCAGATAGTATGCAGC |
| 1970 | AGTCTGTTAAGATATGCGCC |
| 1971 | AGCACGGAACAGTAAGCCCT |
| 1972 | ATCCAGAGAACGTGAGATCC |
| 1973 | GACAGTGTAATATGAGGACC |
| 1974 | CATAGTAGAAGATTCGAGCC |
| 1975 | TGAGATATAGTATGCGGCCA |
| 1976 | ATGAACATACTATACCGCGC |
| 1977 | TTCTCTATATCGTGCGCGGA |
| 1978 | TGAGTTTACGTGTATGGCAC |
| 1979 | ACGGCATCAAAGTTGCATAC |
| 1980 | ACGGGCTCAAAGTATGATAG |
| 1981 | AGGCGCTTAAATGTGGATAC |
| 1982 | CTGCCGTTAATGGCGGACAT |
| 1983 | CTGAGCCAATAGGCGCACTT |
| 1984 | TAGGCATGATGAGAGCTATC |
| 1985 | TGCCTATGAGGAGTATGAAC |
| 1986 | GGGCTATAATGAGCTTGACT |
| 1987 | TAGGCTTCATCAGCTATCAG |
| 1988 | ATTGCTTCAACGGGCATTAC |
| 1989 | TATGATCCATGCGACTCGGA |
| 1990 | TTGTATCCATCGGCCCAGTG |
| 1991 | ATCAAGGCAACCGCCAGTAG |
| 1992 | TCTCAGCCATCCGTGATAGG |
| 1993 | TATCAGGCATCCGAGGATAG |
| 1994 | TTAAGCTCCTCAGTCCATGT |
| 1995 | TAAGGGCGATGAGCCTATCT |
| 1996 | TAAGGCCGAGGAGCTTTCAT |
| 1997 | TAAGGCAGTGGAGCCCTCTA |
| 1998 | TGGACAGGCTGCGCTCTATA |
| 1999 | CTGGAAGCCTGCGACCAAAT |
| 2000 | TCAATGCACTGAGCCCGAGA |
| 2001 | GATTCACACTGACCCATGTA |
| 2002 | TAAATAGATTGGAGACGCGC |

TABLE I-continued

| Seq. Id | 3' to 5' sequence |
|---------|-------------------|
| 2003 | GCATTAGAAGGTCTGGACTA |
| 2004 | ATTGGCATAACGTATTGCGC |
| 2005 | CAGGACTGAAGATCGAGTAC |
| 2006 | TAGAGTCAGTCATAGCTCGA |
| 2007 | TTTATCGTAGCTGGCTGCCC |
| 2008 | AGGATTAGAACCTACGCACC |
| 2009 | GCCGTGAGACCACTGTACTA |
| 2010 | GACGCTGAATCCTATTGACA |
| 2011 | CGCCTAAGGATCGTGAAGTA |
| 2012 | CGACGACGAAGCTGCATGAA |
| 2013 | ACTCGAATAACAGCATCTCG |
| 2014 | CCCGTAAGCATGGCACAGAT |
| 2015 | CAATACAAGATTACGGCCTC |
| 2016 | GATCAGAATCTATGGTACGC |
| 2017 | TCTGTGTACTGCTCGCCAAT |
| 2018 | ATATTTGGAACGCAGCTCAC |
| 2019 | TGCAGTATCGCAGCGGTTCTA |
| 2020 | GGGCAATGTTTATCCACAGA |
| 2021 | CTGACCGAATCCAGCAGAGA |
| 2022 | GATCGTGAATCCGCGCACTA |
| 2023 | GAGCCGTAATCCGAGCGATA |
| 2024 | TACTCCTGACGACTTAGGCA |
| 2025 | TGCTGTCACTCGGCGTCTAT |
| 2026 | GTACTAGCATATCATCGACG |
| 2027 | TATCGCATAGATCAGTGAGC |
| 2028 | TACGGGCAGCCAGGTACTTT |
| 2029 | GTTCATCACGAGTGCGTAGA |
| 2030 | CATGTATCAAGATGGCTGAC |
| 2031 | GGGTCGCGCATTCCAGCATA |
| 2032 | GCACATATCTAGCGACATCT |
| 2033 | ACGCGGCTAAAGGTAGATAC |
| 2034 | CACTGCCCACAAGATGTAGA |
| 2035 | GGATTTACATGGCCTAGCAA |
| 2036 | CATGACACAGAATCGACCGT |
| 2037 | AGAGGCATAAATGAGTCTCC |
| 2038 | TGAGTAGTACGTTACGCCTG |
| 2039 | CGATAGCGAAGGAGTCCACA |
| 2040 | ACACTCTGAAAGACGCGACG |
| 2041 | GTCTTAATGTTGGGCAACG |

TABLE I-continued

| Seq. Id | 3' to 5' sequence |
|---------|-------------------|
| 2042 | GTTATCGACTACGCTGTACT |
| 2043 | TCGTGAGACCGTCGTCAGTA |
| 2044 | GACAGCGCAGTACAGGTAAT |
| 2045 | CGTACAGTAAGTATGATGCC |
| 2046 | TAGAGCATCTGACGCTATGA |
| 2047 | GTCACGATTAGTAGGCACG |
| 2048 | TCGTACCTGTATTCAGCGCG |
| 2049 | TTAATCCGCTGTAGCCCAAA |
| 2050 | TTAATTGACTTCGCTCCAGC |

Experiments

Arrays containing probes corresponding to SEQ ID NOS 1–2050 were designed and manufactured using known photolithography techniques. Four probes were designed to interrogate each sequence from SEQ ID NOS 1–2050: a probe designed to be the perfect match complement to the sequence (PM), a probe designed to have a central mismatch at position 10 (MM), and probes designed to be the complements to the PM and MM probes (cPM and cMM respectively).

Figure 2:
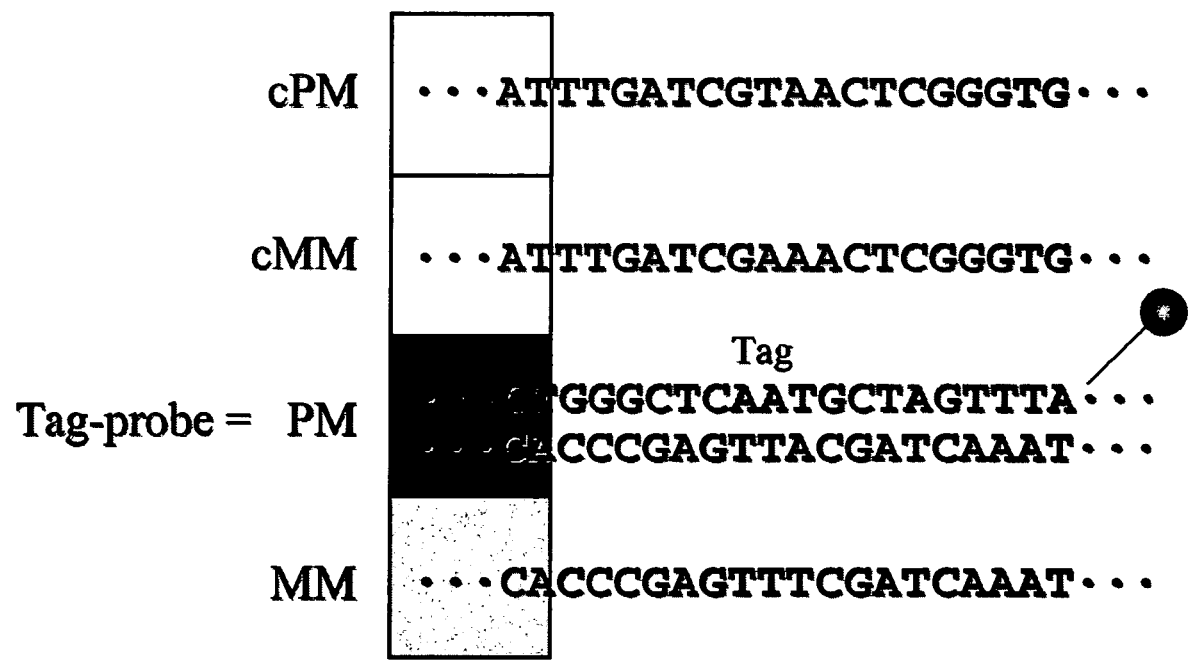
FIG. 2 shows an example of the sequences attached to each of the four array features representing a given tag sequence. Four features, organized vertically on the probe array, represent each tag-probe.

FIG. 2 shows an example of the sequences attached to each of the four array features representing a given tag sequence. The first block contains the cPM probe. The second block contains the cMM probe. The third block contains the PM probe—the probe to which the tag is expected to hybridize with the highest affinity. The fourth block contains the MM probe.

Figure 3:
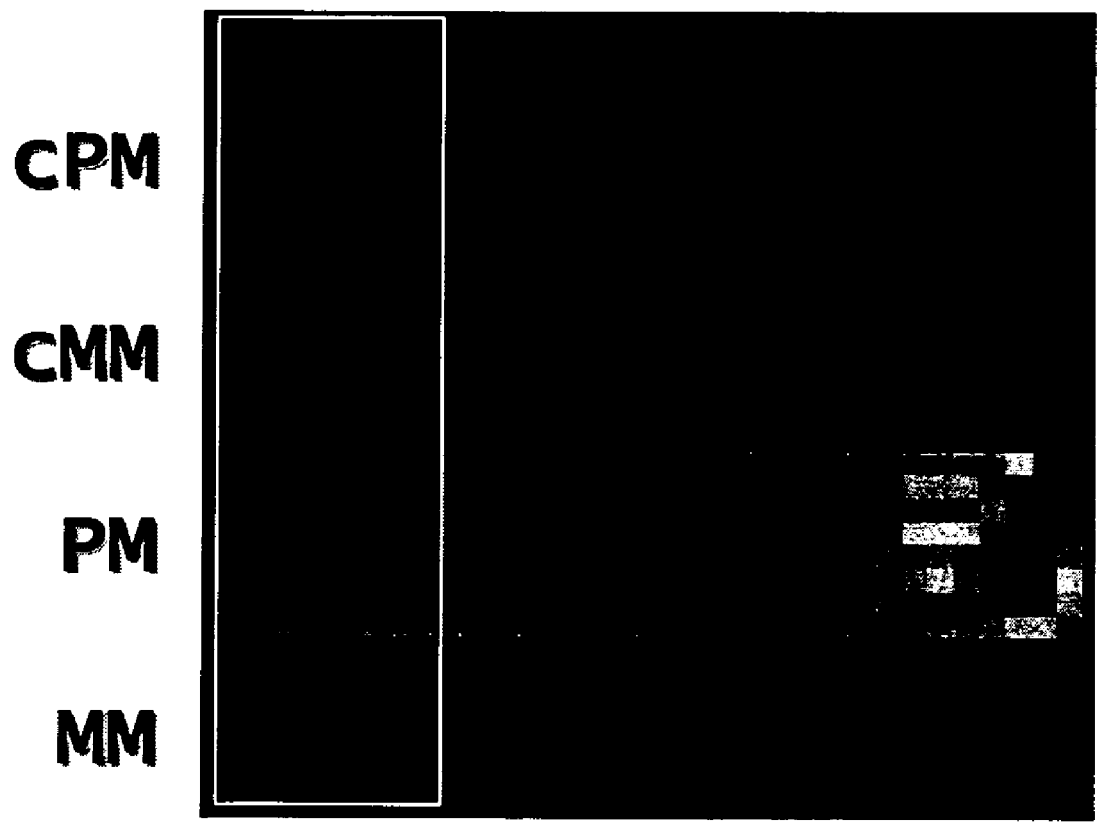
FIG. 3 shows the array features from an array designed to probe for the tag sequences of the presently claimed invention. For each of the four tag-probes shown, arranged horizontally across the array, the brightest hybridization signal is seen with the "PM" feature.

FIG. 3 shows the array features from the above-described array. The array was hybridized with biotin-labeled oligonucleotide tags, stained with streptavidin-phycoerythrin, and the data was collected with a laser scanner. Four features, organized vertically on the probe array, represent each tag-probe. For each of the four tag-probes shown, arranged horizontally across the array, the brightest hybridization signal is seen with the "PM" feature.

Figure 4:
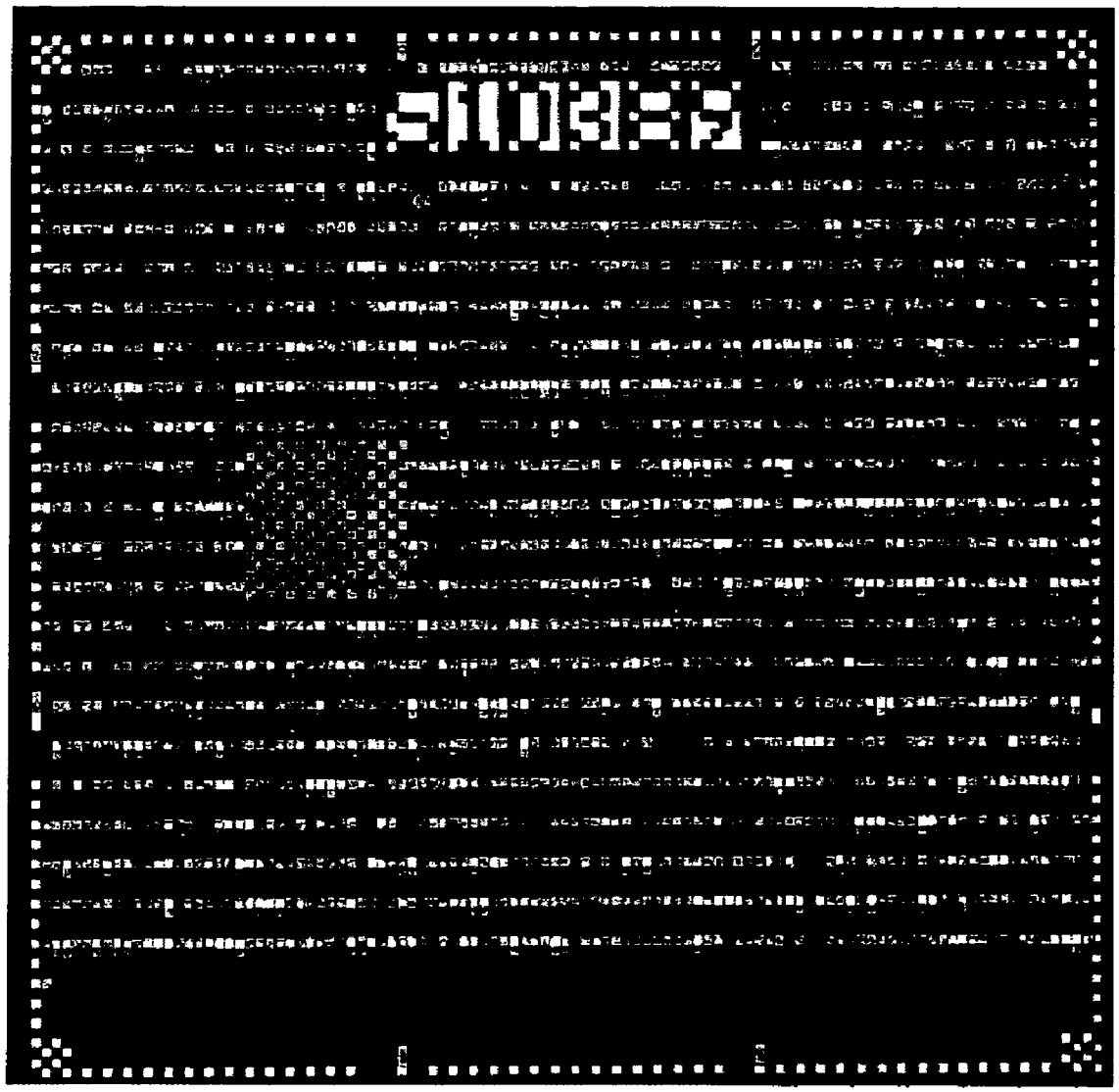
FIG. 4 is a scanned image of the hybridization patterns resulting from the hybridization of 2050 different probes containing regions complementary to the SEQ ID Nos 1–2050 to an array comprised of tag-probes corresponding to SEQ ID Nos 1–2050.

FIG. 4 is a scanned image of the hybridization pattern resulting from the hybridization of 2050 different oligonucleotide tags labeled with phycoerythrin to an array designed as described above.

Figure 5:
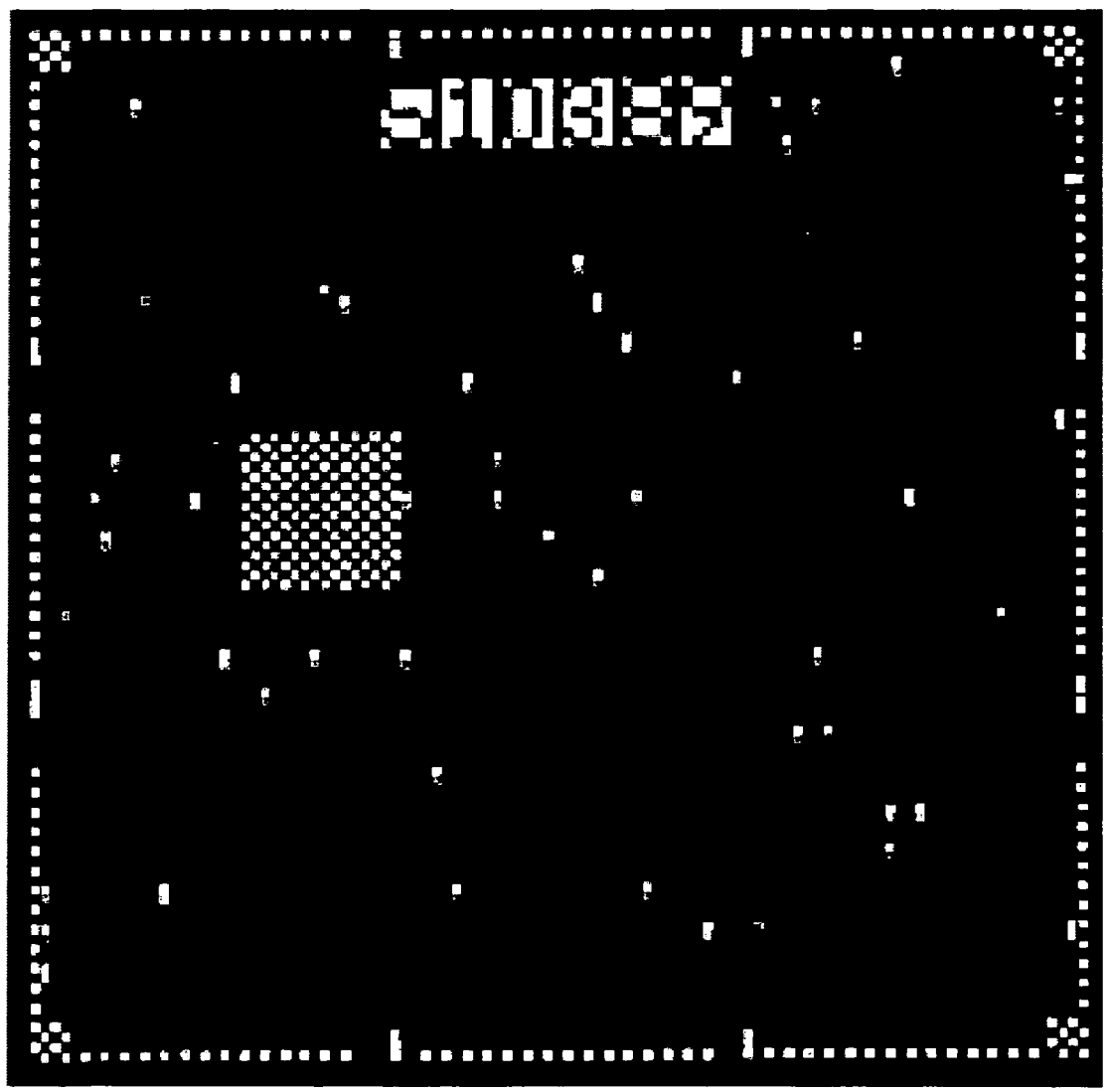
FIG. 5 is a scanned image of the hybridization patterns resulting from the hybridization of 50 different probes containing regions complementary to SEQ ID Nos 2001–2050 to an array identical to the array depicted in FIG. 4.

FIG. 5 is a scanned image of the hybridization pattern resulting from the hybridization of 50 sequences complementary to SEQ ID Nos. 2001–2050 to an array designed as described above.

Figure 6:
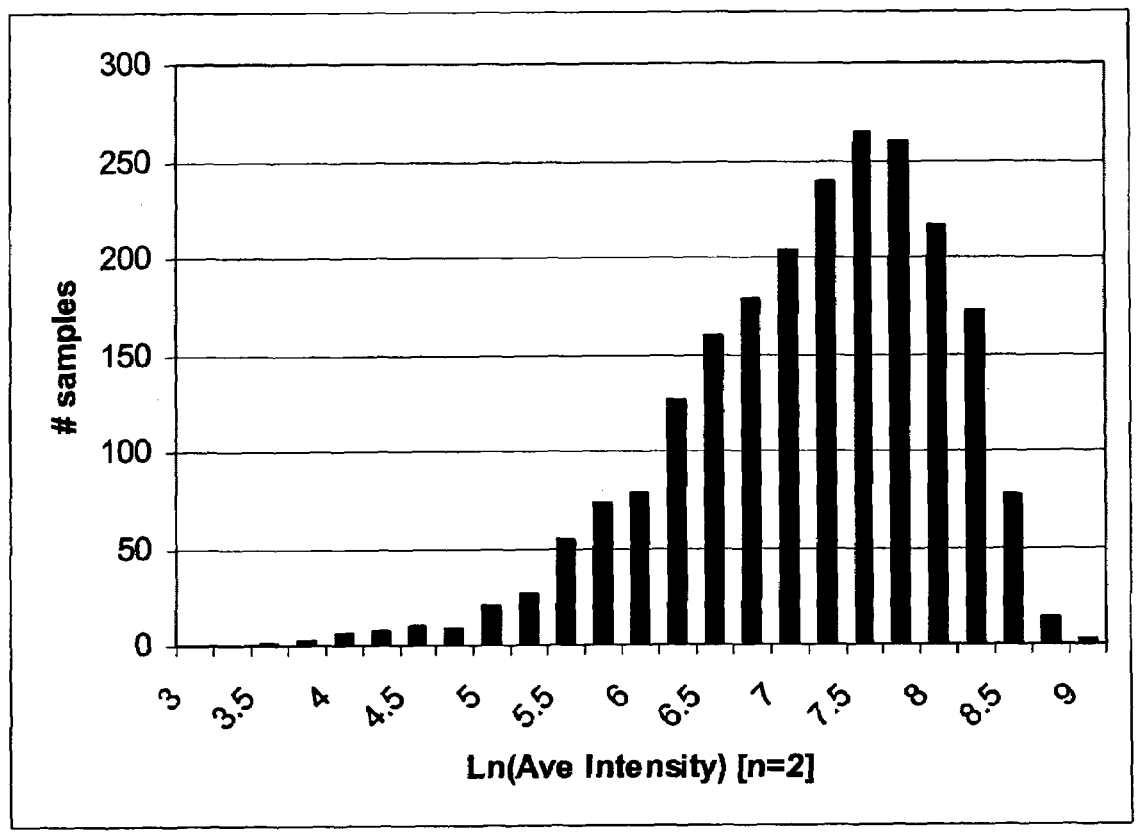
FIG. 6 shows signal intensities from two different independent experiments in which 2000 biotinylated oligonucleotide tags or 50 fluorescein labeled control oligonucleotides were hybridized to arrays designed as described above.

FIG. 6 shows signal intensities from two different independent experiments in which 2000 biotinylated oligonucleotide tags or 50 fluorescein labeled control oligonucleotides were hybridized to arrays designed as described above. The frequency of results are shown as normalized (to scale of 0–1, in bins of 0.05) natural logarithms of the net signal intensities. The normalized natural logarithm of the signal intensities obtained are distributed about a geometric mean of 0.8 with a standard deviation of less than 0.1.

Figure 7:
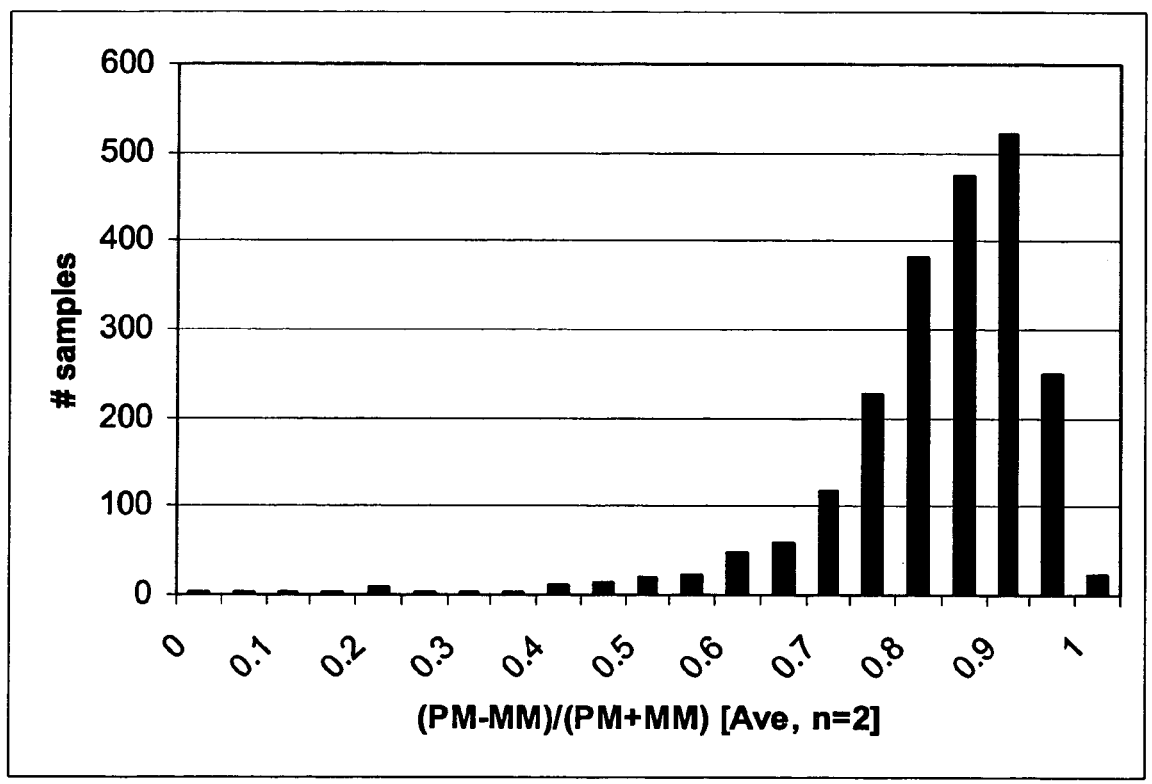
FIG. 7 shows the PM/MM ratios from the data described in FIG. 4 above.

FIG. 7 shows the PM/MM ratios from the data described in FIG. 4 above. More than 98% of the hybridization's yielded a PM/MM ratio greater than 3/1.

CONCLUSION

The above descriptions are illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

We claim:

1. A set of nucleic acid tags probes comprising at least 1000 nucleic acid sequences chosen from the group consisting of:
   SEQ ID NOS: 1–2000.

2. A set of nucleic acid tags comprising at least 1000 nucleic acid sequences chosen from the group consisting of:
   the complements of SEQ ID NOS: 1–2000.

3. The set of nucleic acid tag-probes of claim 1 attached to a solid support.

4. The set of nucleic acid tags of claim 2 attached to a solid support.

5. A set of nucleic acids comprising:
   a first set of nucleic acids comprising each of the sequences listed in SEQ ID NO. 1–2000,
   a second set of nucleic acids comprising the complement of each of the first set of nucleic acids,
   a third set of nucleic acids comprising the first set of nucleic acids wherein position 10 in each of SEQ ID NO: 1–2000 is changed to a mismatch, and
   a fourth set of nucleic acids comprising the complement of each of the third set of nucleic acids.

6. The set of nucleic acids of claim 5 attached to a solid support.

7. The set of nucleic acids of claim 5 further comprising a first set of nucleic acids comprising each of the sequences listed in SEQ ID Nos. 2001–2050.

8. The set of nucleic acids of claim 7 attached to a solid support.

* * * * *

```
                          SEQUENCE LISTING

<160> NUMBER OF SEQ ID NOS: 2050

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
cacccgagtt acgatcaaat                                                  20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
gcctcgggca aacgactaaa                                                  20

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
caccgacgct aatagttaag                                                  20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
catacgcggt aaggatatag                                                  20

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
aatgctcggg aaggctactc                                                  20

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 6
tcttgacgga aaggtagaca                                              20

<210> SEQ ID NO 7
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 7
atcccgtgag tcgatggttt                                              20

<210> SEQ ID NO 8
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 8
cgcaccgcag tttggtcaat                                              20

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 9
cacgcggcag tcgagttaat                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
agcccggtct catcgttgtt                                              20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
agggatatga tacgtgcctt                                              20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
agggctctat tcagcgtatt                                              20

<210> SEQ ID NO 13
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 13
gcgcctgtat taggatatgt                                              20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
catcgagtat aaggatcgtc                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
gcatgggtat aactgtcttc                                              20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
cgcggagtat agagctttat                                              20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
cgagtgctta gatgctagtt                                              20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
cgagcactta acattagagc                                              20

<210> SEQ ID NO 19
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
```
tccgaccttc gatctgtggt                    20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
atcgtacttg gcactggagt                    20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
cgccgtatat ggtcattggt                    20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
gcccaaataa gacgtgagcc                    20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
actcaaacat aactctggcg                    20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
acgagcgcat accatcgaag                    20

<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
tccgacgcaa caatagggca                    20

<210> SEQ ID NO 26
<211> LENGTH: 20
<212> TYPE: DNA
<213> ORGANISM: Artificial Sequence -continued

```
<220> FEATURE:
<223> OTHER INFORMATION: synthetic oligonucleotide

<400> SEQUENCE: 26
cctgctcgac aactagaaga                                               20

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
ccgtgtccag aactagaata                                               20

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
ccgcgaccag aattagatta                                               20

<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 29
gcgcggtcag aactaatata                                               20

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
gcctagtcac caatatacga                                               20

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
gcctcgtcga aattatcaca                                               20

<210> SEQ ID NO 32
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 32
ccgctctcag aatatgtaac                                               20
```

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 33
gccgaagcag acttaatcac                                               20

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
acgtagacag actatcccag                                               20

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
gctatgacag aactacgcac                                               20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
acaggttcag aatcctcgac                                               20

<210> SEQ ID NO 37
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 37
acgcttacag gatactatgg                                               20

<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
ccacgatata ggtacattgg                                               20

<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
cggacgtatc gactttgtgt                          20

<210> SEQ ID NO 40
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 40
ctagaccaac gtcgcttaat                          20

<210> SEQ ID NO 41
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 41
ccgagggtac aaccttaata                          20

<210> SEQ ID NO 42
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 42
ccgagggtat aattcgttac                          20

<210> SEQ ID NO 43
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 43
gcacagccat aattcgtaac                          20

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 44
gcacgtccca gattcgttag                          20

<210> SEQ ID NO 45
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 45
tcgcggacca gattacttag                          20

<210> SEQ ID NO 46

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 46
acgatcaccg tacatcttag                                               20

<210> SEQ ID NO 47
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 47
ataagtccgg tcaagcgtcc                                               20

<210> SEQ ID NO 48
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 48
aataactcgg aaggcgacgc                                               20

<210> SEQ ID NO 49
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 49
aataggacgg aacgccatcc                                               20

<210> SEQ ID NO 50
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 50
acacgcacgg aatagtatcc                                               20

<210> SEQ ID NO 51
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 51
atatgctcgg aacgtgtcgc                                               20

<210> SEQ ID NO 52
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 52
```
atagtgacgg aactgttagc                                               20

<210> SEQ ID NO 53
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 53
caatctacgt caagcgttac                                               20

<210> SEQ ID NO 54
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 54
cagtcatcgt aacctgatag                                               20

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
aatgtcgcgt aatggcttag                                               20

<210> SEQ ID NO 56
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 56
aatgcgacgt aactttgcag                                               20

<210> SEQ ID NO 57
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 57
aatcagccgt aacgtgagag                                               20

<210> SEQ ID NO 58
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 58
tcatgcgcgt aagcctagag                                               20

<210> SEQ ID NO 59
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 59
tagtacccgg aacctagagc                                              20

<210> SEQ ID NO 60
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 60
agtaccaatg acacgttcga                                              20

<210> SEQ ID NO 61
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 61
tcccatacga caagttgaga                                              20

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62
tgaccggcag gctagtctat                                              20

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
gactccgcgt catcagttat                                              20

<210> SEQ ID NO 64
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 64
ccgctatggg ttatcaggtt                                              20

<210> SEQ ID NO 65
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 65
ctcgcgtagg ttagactgtt                                              20
```

```
<210> SEQ ID NO 66
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 66
ctatgtgcgg taagacgtat                                            20

<210> SEQ ID NO 67
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 67
gctagtcacg aataggttac                                            20

<210> SEQ ID NO 68
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 68
atagcaccgg aataaggccc                                            20

<210> SEQ ID NO 69
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 69
ctagaccagg taagatactc                                            20

<210> SEQ ID NO 70
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 70
ccgactcacg aattagatac                                            20

<210> SEQ ID NO 71
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 71
ccatcgcacg aatgtagtac                                            20

<210> SEQ ID NO 72
<211> LENGTH: 20
<212> TYPE: DNA
<213> ORGANISM: Artificial Sequence
<220> FEATURE:
```

```
<223> OTHER INFORMATION: synthetic oligonucleotide

<400> SEQUENCE: 72
ctcatagacg aagcgaggac                                          20

<210> SEQ ID NO 73
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 73
tgcactcacg aagacgagac                                          20

<210> SEQ ID NO 74
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 74
cactacgact tcggatacat                                          20

<210> SEQ ID NO 75
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 75
cgcgcctagt tccatattat                                          20

<210> SEQ ID NO 76
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 76
gcggcatacg ttcgtcaaat                                          20

<210> SEQ ID NO 77
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 77
ccaggcgacg ttccgaatat                                          20

<210> SEQ ID NO 78
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 78
tcgatctagg tggcgaattt                                          20
```

```
<210> SEQ ID NO 79
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 79
agcgacgagt tccgataatt                                              20

<210> SEQ ID NO 80
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 80
gctcccaagg ttcgtaaata                                              20

<210> SEQ ID NO 81
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 81
cgagctaagg tacttgaaag                                              20

<210> SEQ ID NO 82
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 82
cagactcagc tttaggaacg                                              20

<210> SEQ ID NO 83
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 83
gctcctcgct aataagaaac                                              20

<210> SEQ ID NO 84
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 84
cggctcagta ttcacgaaat                                              20

<210> SEQ ID NO 85
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 85
cgcggatgtc ttacgatatt                                              20

<210> SEQ ID NO 86
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 86
ccgattagtt tacagtcgct                                              20

<210> SEQ ID NO 87
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 87
ccggctctat aataagttcc                                              20

<210> SEQ ID NO 88
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 88
cacgtcgtta aagacctgga                                              20

<210> SEQ ID NO 89
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 89
agcgatctta aaggactcga                                              20

<210> SEQ ID NO 90
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 90
ccggagatta aacgtatcga                                              20

<210> SEQ ID NO 91
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 91
cacggtattt aatcggatgg                                              20

<210> SEQ ID NO 92
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 92
cgccgtaact taacgtaatc                                                    20

<210> SEQ ID NO 93
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 93
tcgcataact aacggtcaac                                                    20

<210> SEQ ID NO 94
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 94
ctatgcaacg taagcgaacc                                                    20

<210> SEQ ID NO 95
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 95
catagaggtt aagcgatacg                                                    20

<210> SEQ ID NO 96
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 96
catagtaggt aagctgtacg                                                    20

<210> SEQ ID NO 97
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 97
tcagctcggt aacttgcacg                                                    20

<210> SEQ ID NO 98
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 98
```
atgagctgtc taacgcgacg                                              20

<210> SEQ ID NO 99
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 99
catagtccta aacgtgacga                                              20

<210> SEQ ID NO 100
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 100
acatggtcta aacgcttcga                                              20

<210> SEQ ID NO 101
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 101
aagtcatcta aagcgtccga                                              20

<210> SEQ ID NO 102
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 102
cagaggtatt aagctagacg                                              20

<210> SEQ ID NO 103
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 103
ccgtactatt aactgagacg                                              20

<210> SEQ ID NO 104
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 104
ccctttacat aacggattgc                                              20

<210> SEQ ID NO 105
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 105
cagcttctga aacgtggtca                                               20

<210> SEQ ID NO 106
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 106
cctgctgtgt aagtatatgg                                               20

<210> SEQ ID NO 107
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 107
cagtggatct aacgtgatag                                               20

<210> SEQ ID NO 108
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 108
atcatgtagg taacgtgacg                                               20

<210> SEQ ID NO 109
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 109
atcggcctgt aatcggatcg                                               20

<210> SEQ ID NO 110
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 110
actcgtgtgt aatccgatgg                                               20

<210> SEQ ID NO 111
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 111
ccagtgttct aacgtgcagg                                               20
```

-continued

<210> SEQ ID NO 112
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 112
aagctgatct aagccgcgag                                               20

<210> SEQ ID NO 113
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 113
tattcgatct ccagcgaggg                                               20

<210> SEQ ID NO 114
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 114
aattcgctct aagctgggcg                                               20

<210> SEQ ID NO 115
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 115
aattatgtcg aacgcgccgc                                               20

<210> SEQ ID NO 116
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 116
aattctgtcg aagcgtcggc                                               20

<210> SEQ ID NO 117
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 117
aattggctag aatcgcctac                                               20

<210> SEQ ID NO 118
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 118
gactacctaa tacgacgtgc                                              20

<210> SEQ ID NO 119
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 119
ccttacgcta ggtcgagagt                                              20

<210> SEQ ID NO 120
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 120
ccgactctag gatcgtggat                                              20

<210> SEQ ID NO 121
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 121
ccggacttag gactatggat                                              20

<210> SEQ ID NO 122
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 122
tatatgctga gtgaccgcgt                                              20

<210> SEQ ID NO 123
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 123
tatcaactag gtgcaacgac                                              20

<210> SEQ ID NO 124
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 124
ccataactag aatcggcgac                                              20

<210> SEQ ID NO 125
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 125
tgatccggtc taatccgacg                                           20

<210> SEQ ID NO 126
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 126
acttaacgtc catgtccggg                                           20

<210> SEQ ID NO 127
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 127
tattgtcgtc caggccggat                                           20

<210> SEQ ID NO 128
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 128
attgtgaggc accgccgaat                                           20

<210> SEQ ID NO 129
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 129
tgatgcagag ttctcggaat                                           20

<210> SEQ ID NO 130
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 130
caggtacgac tagcccgaat                                           20

<210> SEQ ID NO 131
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 131
```
agattcgact gatgcccgtt                                         20

<210> SEQ ID NO 132
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 132
gtcacagact agccacgaag                                         20

<210> SEQ ID NO 133
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 133
tgacacgatg aaccacggac                                         20

<210> SEQ ID NO 134
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 134
ttgactcatg taccgcgtgg                                         20

<210> SEQ ID NO 135
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 135
ttgcgcgagc tattcggact                                         20

<210> SEQ ID NO 136
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 136
ttgatccagc tagacggacg                                         20

<210> SEQ ID NO 137
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 137
catatagact cagggatagg                                         20

<210> SEQ ID NO 138
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 138
agaccgcatc cattggtacg                                               20

<210> SEQ ID NO 139
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 139
aacgcatact cagtcggagg                                               20

<210> SEQ ID NO 140
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 140
atagctgatc cagtccgagg                                               20

<210> SEQ ID NO 141
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 141
taatagcggc ttaaccggcg                                               20

<210> SEQ ID NO 142
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 142
taccggatta cagctcgtgg                                               20

<210> SEQ ID NO 143
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 143
taacaggcga tacaccctag                                               20

<210> SEQ ID NO 144
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 144
tacacgactg tctaacctag                                               20
```

<210> SEQ ID NO 145
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 145
tgaccatcag tctaaccgag                                              20

<210> SEQ ID NO 146
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 146
atgctgtcag tataggtcgt                                              20

<210> SEQ ID NO 147
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 147
atgcagtcgt cacgtctcgt                                              20

<210> SEQ ID NO 148
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 148
gatgtgtcag accgaccact                                              20

<210> SEQ ID NO 149
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 149
gcacgtacta ccaacgagga                                              20

<210> SEQ ID NO 150
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 150
tagagcccta tccatacggg                                              20

<210> SEQ ID NO 151
<211> LENGTH: 20
<212> TYPE: DNA
<213> ORGANISM: Artificial Sequence
<220> FEATURE:

```
<223> OTHER INFORMATION: synthetic oligonucleotide

<400> SEQUENCE: 151
ttagactcac catagcgggc                                               20

<210> SEQ ID NO 152
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 152
tgcatacaga ccaacggcga                                               20

<210> SEQ ID NO 153
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 153
tgagaggaac cataccgcac                                               20

<210> SEQ ID NO 154
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 154
agcagcgaac catacgtgac                                               20

<210> SEQ ID NO 155
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 155
gcatctaaca catgacggac                                               20

<210> SEQ ID NO 156
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 156
agtcgatacc tacgctgcat                                               20

<210> SEQ ID NO 157
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 157
atagacgact ccacagtgag                                               20
```

```
<210> SEQ ID NO 158
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 158
tgagaggact ccacgacatc                                               20

<210> SEQ ID NO 159
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 159
tatgaggacc tacagcactc                                               20

<210> SEQ ID NO 160
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 160
tgtagagaga cagcacgacc                                               20

<210> SEQ ID NO 161
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 161
tagagagagt ccacacacgc                                               20

<210> SEQ ID NO 162
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 162
aatgtagact cacgcacgcg                                               20

<210> SEQ ID NO 163
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 163
tgagagcacc aactcgcaga                                               20

<210> SEQ ID NO 164
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 164
agagatcact gacaccgcag                                              20

<210> SEQ ID NO 165
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 165
tagactcatg tcacacgcgg                                              20

<210> SEQ ID NO 166
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 166
atagaccatg accgcgaagc                                              20

<210> SEQ ID NO 167
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 167
tagtctcatc catcgctggg                                              20

<210> SEQ ID NO 168
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 168
catgaccatc tagtacagag                                              20

<210> SEQ ID NO 169
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 169
actgacgact cattcgcagg                                              20

<210> SEQ ID NO 170
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 170
actatcgaga cattgtgggc                                              20

<210> SEQ ID NO 171
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 171
attacagaca cattcggcgc                                               20

<210> SEQ ID NO 172
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 172
gacgattaca cattcgaggc                                               20

<210> SEQ ID NO 173
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 173
tagcacttca catacgagtc                                               20

<210> SEQ ID NO 174
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 174
cgtagatgtc aatactagcc                                               20

<210> SEQ ID NO 175
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 175
agagttcgtc aatagccgcc                                               20

<210> SEQ ID NO 176
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 176
agatgtagag catataccgg                                               20

<210> SEQ ID NO 177
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 177
```
tatggtcggc aattccctgc                                              20

<210> SEQ ID NO 178
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 178
gcgtatcagc aagacccata                                              20

<210> SEQ ID NO 179
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 179
tctaagtagc aagcaccctc                                              20

<210> SEQ ID NO 180
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 180
aatagcggcc aagacgccta                                              20

<210> SEQ ID NO 181
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 181
aatttgtgcg aagccgctcc                                              20

<210> SEQ ID NO 182
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 182
atattctgag acacgccgcg                                              20

<210> SEQ ID NO 183
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 183
atatacgaga cacgtcgcgc                                              20

<210> SEQ ID NO 184
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 184
tatagacgga cacagtcgcc                                               20

<210> SEQ ID NO 185
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 185
tatatgtgga ccagtatgcg                                               20

<210> SEQ ID NO 186
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 186
tcatgtcgtg gaagtatgtc                                               20

<210> SEQ ID NO 187
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 187
ctatgtagga gcacgctttg                                               20

<210> SEQ ID NO 188
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 188
ctatttagga gacgctcgtg                                               20

<210> SEQ ID NO 189
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 189
attcagcgat gagaccggat                                               20

<210> SEQ ID NO 190
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 190
cattgacgag aatcctagac                                               20
```

<210> SEQ ID NO 191
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 191
acttagcgag gatcgtagat                                              20

<210> SEQ ID NO 192
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 192
actatacgag gtggctgaat                                              20

<210> SEQ ID NO 193
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 193
aaatcctcag gtgcgcgaat                                              20

<210> SEQ ID NO 194
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 194
tatacgcgag tcaggtgaat                                              20

<210> SEQ ID NO 195
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 195
tagactaggt gacggcatat                                              20

<210> SEQ ID NO 196
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 196
agactcacgt aacgcatatc                                              20

<210> SEQ ID NO 197
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 197
ccaggtagtg aactgctatc                                                   20

<210> SEQ ID NO 198
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 198
cgagctagtg gatcagatat                                                   20

<210> SEQ ID NO 199
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 199
aaactacggg tgagcatgat                                                   20

<210> SEQ ID NO 200
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 200
tcagtacgag tgatgcagat                                                   20

<210> SEQ ID NO 201
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 201
cgtatctagg attgagcagt                                                   20

<210> SEQ ID NO 202
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 202
gtacctgcga tgtgagcatt                                                   20

<210> SEQ ID NO 203
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 203
tgacgctcta cgatgctgct                                                   20

<210> SEQ ID NO 204
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 204
catgacgcta ggatgcagct                                                   20

<210> SEQ ID NO 205
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 205
gagcatgagg tactatgact                                                   20

<210> SEQ ID NO 206
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 206
tcagctaggg tagatcacgt                                                   20

<210> SEQ ID NO 207
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 207
tgcactgccg tcattagcgt                                                   20

<210> SEQ ID NO 208
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 208
atgccgacgg tatctcaggt                                                   20

<210> SEQ ID NO 209
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 209
tgcctgacgt tgacgacagt                                                   20

<210> SEQ ID NO 210
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 210
```
agctcgacgt tcggacacat                                               20

<210> SEQ ID NO 211
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 211
attactccgt gaggcgacgt                                               20

<210> SEQ ID NO 212
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 212
actataccta gagggacgcg                                               20

<210> SEQ ID NO 213
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 213
atatgacctg aaccgacggc                                               20

<210> SEQ ID NO 214
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 214
atatgtgcag aacccgcgac                                               20

<210> SEQ ID NO 215
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 215
ctgatagcga tacgtccgtg                                               20

<210> SEQ ID NO 216
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 216
ttatgtccga gagcgtccgt                                               20

<210> SEQ ID NO 217
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 217
atcttgccga gagctacggt                                               20

<210> SEQ ID NO 218
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 218
ctatattcga gacgaggacg                                               20

<210> SEQ ID NO 219
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 219
acatttgcag cactagggcg                                               20

<210> SEQ ID NO 220
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 220
cctcttacga gatagcggtg                                               20

<210> SEQ ID NO 221
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 221
ccgtttacca aagagcgcaa                                               20

<210> SEQ ID NO 222
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 222
ggcctaactc aacagacgga                                               20

<210> SEQ ID NO 223
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 223
gctcacatcc aacgagagga                                               20
```

<210> SEQ ID NO 224
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 224
gggtacatcc aagcaaccga                                         20

<210> SEQ ID NO 225
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 225
aagtaagctg cacgaacgcc                                         20

<210> SEQ ID NO 226
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 226
atgcaaacag caggtacgcg                                         20

<210> SEQ ID NO 227
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 227
attatagatg cagaggaccg                                         20

<210> SEQ ID NO 228
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 228
ctactagaga gagatacgcg                                         20

<210> SEQ ID NO 229
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 229
cgcttagatg gctatatggt                                         20

<210> SEQ ID NO 230
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 230
cacttaggtg gaatatcgag                                            20

<210> SEQ ID NO 231
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 231
ccacttagtt caataggcgc                                            20

<210> SEQ ID NO 232
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 232
agcgatagtc cattcggctg                                            20

<210> SEQ ID NO 233
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 233
cctatccgta catatcgagg                                            20

<210> SEQ ID NO 234
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 234
tatgctcgta catgccgtgg                                            20

<210> SEQ ID NO 235
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 235
tatgctcgtg cagttcggct                                            20

<210> SEQ ID NO 236
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 236
actctcagat cagtgtcggg                                            20

```
<210> SEQ ID NO 237
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 237
acacgcagat gatttaagcg                                                   20

<210> SEQ ID NO 238
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 238
acatggcgat aagctctaag                                                   20

<210> SEQ ID NO 239
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 239
gatgacagta cagttgacag                                                   20

<210> SEQ ID NO 240
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 240
cacatacgct acagttacag                                                   20

<210> SEQ ID NO 241
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 241
cacgagtgct aagatttgag                                                   20

<210> SEQ ID NO 242
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 242
ccgagctgtg aacgcttatc                                                   20

<210> SEQ ID NO 243
<211> LENGTH: 20
<212> TYPE: DNA
<213> ORGANISM: Artificial Sequence
<220> FEATURE:
<223> OTHER INFORMATION: synthetic oligonucleotide
```

-continued

<400> SEQUENCE: 243
gcagctcgtc acaggtattg                                    20

<210> SEQ ID NO 244
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 244
acactgcgta aatcttgcga                                    20

<210> SEQ ID NO 245
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 245
catcactgtc aagtatagcc                                    20

<210> SEQ ID NO 246
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 246
catacatctg aagtaagcgc                                    20

<210> SEQ ID NO 247
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 247
ccatatagcg aagtatcacc                                    20

<210> SEQ ID NO 248
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 248
cgccatagag aagtgaccac                                    20

<210> SEQ ID NO 249
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 249
ctccatagta cattgtcacg                                    20

<210> SEQ ID NO 250
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 250
atccgtactg acattgaccg                                               20

<210> SEQ ID NO 251
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 251
tagtcaccta gatcgacgcg                                               20

<210> SEQ ID NO 252
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 252
atttactcca gaggcgtgcg                                               20

<210> SEQ ID NO 253
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 253
tatttcgcac ggagcactcg                                               20

<210> SEQ ID NO 254
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 254
ttattcgcac gatgaccgcg                                               20

<210> SEQ ID NO 255
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 255
tactactcac gatgactcgg                                               20

<210> SEQ ID NO 256
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 256
```
tgcataacac gacacgttca                                               20

<210> SEQ ID NO 257
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 257
attatagcac gacataccgc                                               20

<210> SEQ ID NO 258
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 258
ttatgagcac gacagacgcc                                               20

<210> SEQ ID NO 259
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 259
tctagcacat cagaggaacc                                               20

<210> SEQ ID NO 260
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 260
tatgcagctc gatggacacg                                               20

<210> SEQ ID NO 261
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 261
gacttgccat cgtagaactg                                               20

<210> SEQ ID NO 262
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 262
caagtgactc gaagtatagc                                               20

<210> SEQ ID NO 263
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 263
acaacgctat cgaagtatcc                                                   20

<210> SEQ ID NO 264
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 264
gagagcctac gacactattc                                                   20

<210> SEQ ID NO 265
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 265
aacagtttag caacgtgccc                                                   20

<210> SEQ ID NO 266
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 266
actaatcttg aattggcggc                                                   20

<210> SEQ ID NO 267
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 267
tattcgatag tacgagctgg                                                   20

<210> SEQ ID NO 268
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 268
tattcgatac gacgatggtg                                                   20

<210> SEQ ID NO 269
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 269
tgactcctac gaggtgcgat                                                   20
```

```
<210> SEQ ID NO 270
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 270
gactatcaac gagtggcaac                                                    20

<210> SEQ ID NO 271
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 271
actatctaac gagcttggtc                                                    20

<210> SEQ ID NO 272
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 272
catctcgtag gatctgggct                                                    20

<210> SEQ ID NO 273
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 273
atcactgtag tcacgtagct                                                    20

<210> SEQ ID NO 274
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 274
tctagcgtac cctatatgct                                                    20

<210> SEQ ID NO 275
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 275
attcgactac gacctggcat                                                    20

<210> SEQ ID NO 276
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 276
gtagacatcc aacctgacta                                               20

<210> SEQ ID NO 277
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 277
ggcatactcc aagtcaacta                                               20

<210> SEQ ID NO 278
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 278
atcgagggac gagtcttcat                                               20

<210> SEQ ID NO 279
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 279
acctgcggac gagtattgat                                               20

<210> SEQ ID NO 280
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 280
tagcaccgac tacagtgttc                                               20

<210> SEQ ID NO 281
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 281
tctacacgag aacgaggcac                                               20

<210> SEQ ID NO 282
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 282
acataccgag aagtgggcac                                               20

<210> SEQ ID NO 283

```
-continued
```

<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 283
cctactcgat aattgaggac                                             20

<210> SEQ ID NO 284
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 284
ccgcgacgat tgattagaat                                             20

<210> SEQ ID NO 285
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 285
caccgcagac gattagtgag                                             20

<210> SEQ ID NO 286
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 286
gcaccgtaac cattagtagc                                             20

<210> SEQ ID NO 287
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 287
acacctacac gattagtcag                                             20

<210> SEQ ID NO 288
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 288
cccgtatcac gatgtattag                                             20

<210> SEQ ID NO 289
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 289

```
ccgtatcgag cattatatcg                                               20

<210> SEQ ID NO 290
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 290
accggacgga gctatatttg                                               20

<210> SEQ ID NO 291
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 291
gcgagactag cctatcattg                                               20

<210> SEQ ID NO 292
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 292
gctgaactac catgtactgc                                               20

<210> SEQ ID NO 293
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 293
agcgtactag gcatctattg                                               20

<210> SEQ ID NO 294
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 294
agcgtactct gaatgccgtc                                               20

<210> SEQ ID NO 295
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 295
acatacgtca taagccgatc                                               20

<210> SEQ ID NO 296
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 296
attgcgctaa gagctgcgtc                                            20

<210> SEQ ID NO 297
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 297
gcttcgataa cagcacatac                                            20

<210> SEQ ID NO 298
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 298
cgttacatac tcagccatag                                            20

<210> SEQ ID NO 299
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 299
agacgactag cacgccatag                                            20

<210> SEQ ID NO 300
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 300
gaggtcatca gacgtatatg                                            20

<210> SEQ ID NO 301
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 301
ccgaccctat tagctgatat                                            20

<210> SEQ ID NO 302
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 302
gcagccctat aacatgatac                                            20
```

```
<210> SEQ ID NO 303
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 303
gtgaccatca tcgacagttc                                            20

<210> SEQ ID NO 304
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 304
acacagctat cgacagagtc                                            20

<210> SEQ ID NO 305
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 305
gcacaccttc tgaatgagtc                                            20

<210> SEQ ID NO 306
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 306
gactgcgtat catataggct                                            20

<210> SEQ ID NO 307
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 307
tgacacgtaa gataggatgc                                            20

<210> SEQ ID NO 308
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 308
ggagcactca cacatagtac                                            20

<210> SEQ ID NO 309
<211> LENGTH: 20
<212> TYPE: DNA
<213> ORGANISM: Artificial Sequence
<220> FEATURE:
```

```
<223> OTHER INFORMATION: synthetic oligonucleotide

<400> SEQUENCE: 309
gcatacatca gcactaaggc                                               20

<210> SEQ ID NO 310
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 310
actccactga gcactatggg                                               20

<210> SEQ ID NO 311
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 311
ccgacactat gctaagagag                                               20

<210> SEQ ID NO 312
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 312
ccgtccatct aatgtatgag                                               20

<210> SEQ ID NO 313
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 313
ccgacgatga tactaatgag                                               20

<210> SEQ ID NO 314
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 314
ggagccacga cctatatcag                                               20

<210> SEQ ID NO 315
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 315
agactcacct cgatatacag                                               20
```

<210> SEQ ID NO 316
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 316
agcgcgacgt tgatccagat                                               20

<210> SEQ ID NO 317
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 317
gacggcactt tgcacatcat                                               20

<210> SEQ ID NO 318
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 318
acgcgcactg tctatacatg                                               20

<210> SEQ ID NO 319
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 319
atcgccgcat cctatatgat                                               20

<210> SEQ ID NO 320
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 320
cgaccgtaac gctatatgag                                               20

<210> SEQ ID NO 321
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 321
ccaccggata cactgttgag                                               20

<210> SEQ ID NO 322
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 322
catccttata cagtacgcag                                              20

<210> SEQ ID NO 323
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 323
accgatgaca gttcacagag                                              20

<210> SEQ ID NO 324
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 324
acactagact cattgatcgg                                              20

<210> SEQ ID NO 325
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 325
tcactcgatc tgaataacgc                                              20

<210> SEQ ID NO 326
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 326
cacactgacg aatcatgtac                                              20

<210> SEQ ID NO 327
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 327
cggcctaact gtaattgatc                                              20

<210> SEQ ID NO 328
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 328
cgacgttact aatgtgtcag                                              20

<210> SEQ ID NO 329
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 329
cgacacgact aagtgcttgc                                              20

<210> SEQ ID NO 330
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 330
agacacgaca cactggctta                                              20

<210> SEQ ID NO 331
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 331
gaatcacaca cagtcgtcta                                              20

<210> SEQ ID NO 332
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 332
cggatgtata aatcgctcga                                              20

<210> SEQ ID NO 333
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 333
gcacactata aacgctgtca                                              20

<210> SEQ ID NO 334
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 334
gataaccaac cagtctgtca                                              20

<210> SEQ ID NO 335
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 335
```
agactccagg tcgatcattg                                            20

<210> SEQ ID NO 336
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 336
acaaggcgtg gtcagatatt                                            20

<210> SEQ ID NO 337
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 337
caagcgcgtg tcatacgatt                                            20

<210> SEQ ID NO 338
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 338
taagctggat tcagtcgtgt                                            20

<210> SEQ ID NO 339
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 339
atatcgcgtt gcagggctct                                            20

<210> SEQ ID NO 340
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 340
atatcggttg cagcgcctgt                                            20

<210> SEQ ID NO 341
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 341
catcgcgtgt cagtgcttgt                                            20

<210> SEQ ID NO 342
<211> LENGTH: 20
<212> TYPE: DNA
<213> ORGANISM: Artificial Sequence -continued

```
<220> FEATURE:
<223> OTHER INFORMATION: synthetic oligonucleotide

<400> SEQUENCE: 342
catcgctggt catggactgt                                              20

<210> SEQ ID NO 343
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 343
gccatcggtg tcatgtactt                                              20

<210> SEQ ID NO 344
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 344
agtacgcggt gagatcattt                                              20

<210> SEQ ID NO 345
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 345
gaccggcttg tagatagatt                                              20

<210> SEQ ID NO 346
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 346
gcgcggatat tagataactc                                              20

<210> SEQ ID NO 347
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 347
aaaggcattg tcgctaagct                                              20

<210> SEQ ID NO 348
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 348
atacgcgatg ggatcagact                                              20
```

<210> SEQ ID NO 349
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 349
atgacggatg tatgacgact    20

<210> SEQ ID NO 350
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 350
tttatcgcac tgggccgaat    20

<210> SEQ ID NO 351
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 351
tatggacgtg tagccagtat    20

<210> SEQ ID NO 352
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 352
ttgtagcggc tcgcacgatt    20

<210> SEQ ID NO 353
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 353
ttcgagcgtc tggcacactt    20

<210> SEQ ID NO 354
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 354
tatagaggag gacagacttc    20

<210> SEQ ID NO 355
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 355
atttagcgtg cagccgacct                                               20

<210> SEQ ID NO 356
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 356
gatgttcgtc catgcgacct                                               20

<210> SEQ ID NO 357
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 357
gagcttcgtg aactgacctc                                               20

<210> SEQ ID NO 358
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 358
aagagtagtg aagcgacctc                                               20

<210> SEQ ID NO 359
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 359 ataccgct aggcgactgt                                                 20

<210> SEQ ID NO 360
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 360
tatggactag gagcgtacct                                               20

<210> SEQ ID NO 361
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 361
atgcgactct tgacgaacgt                                               20

<210> SEQ ID NO 362
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 362
gtcactcgtg tccaggatgt                                                   20

<210> SEQ ID NO 363
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 363
tcggactcgt gacgctattt                                                   20

<210> SEQ ID NO 364
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 364
ttcgacccgg acgactgtat                                                   20

<210> SEQ ID NO 365
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 365
tgatccgcgt cgatgctctt                                                   20

<210> SEQ ID NO 366
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 366
tacgcaggga tcgagcttat                                                   20

<210> SEQ ID NO 367
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 367
ggagcgagcg tcatatttat                                                   20

<210> SEQ ID NO 368
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 368
```
agagcacggt cacattccag　　20

<210> SEQ ID NO 369
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 369
ttgcagggta cgatagtcat　　20

<210> SEQ ID NO 370
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 370
atctcgcgtg acgataggct　　20

<210> SEQ ID NO 371
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 371
attaccggag cacgtagtcg　　20

<210> SEQ ID NO 372
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 372
atactcggag cactaggtcg　　20

<210> SEQ ID NO 373
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 373
gataccggac catgtttcgc　　20

<210> SEQ ID NO 374
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 374
tgacccagac cagttagtgc　　20

<210> SEQ ID NO 375
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 375
actggcagac taggtcgcat                                              20

<210> SEQ ID NO 376
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 376
gcacagagac gcaagtccta                                              20

<210> SEQ ID NO 377
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 377
acatcaagac cacgttgcta                                              20

<210> SEQ ID NO 378
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 378
atagtacgac caggactctc                                              20

<210> SEQ ID NO 379
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 379
actgaccgtc tagcgagtct                                              20

<210> SEQ ID NO 380
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 380
gctatatgta tccagagtgg                                              20

<210> SEQ ID NO 381
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 381
gctgtacgga ttctgagatt                                              20
```

```
<210> SEQ ID NO 382
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 382
catggacgga tgccgatatt                                               20

<210> SEQ ID NO 383
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 383
acgcacaggt tatgaatctc                                               20

<210> SEQ ID NO 384
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 384
agtcacagga tataggatcg                                               20

<210> SEQ ID NO 385
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 385
gcatgacgtg taagctatcg                                               20

<210> SEQ ID NO 386
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 386
tgagcaggcg tcacctatct                                               20

<210> SEQ ID NO 387
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 387
tctcgacgtg tactcatact                                               20

<210> SEQ ID NO 388
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 388
tgtcaccggc tagagctact 20

<210> SEQ ID NO 389
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 389
cacgactgac catagtattc 20

<210> SEQ ID NO 390
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 390
cccgattgag gcatggttat 20

<210> SEQ ID NO 391
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 391
cgaccttgac ccagtagatg 20

<210> SEQ ID NO 392
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 392
agactctgag ccattgtcgg 20

<210> SEQ ID NO 393
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 393
acgctatgag gattgatcgt 20

<210> SEQ ID NO 394
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 394
acgcactgac gatcattcgg 20

```
<210> SEQ ID NO 395
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 395
ccatgctgag aatatacgac                                              20

<210> SEQ ID NO 396
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 396
tcgcatcgca gatactacgg                                              20

<210> SEQ ID NO 397
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 397
aatcgacgct aacgactgag                                              20

<210> SEQ ID NO 398
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 398
caacgaggcg taatgactag                                              20

<210> SEQ ID NO 399
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 399
taggcaggcg tagatactat                                              20

<210> SEQ ID NO 400
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 400
aatgagcgcg aacacctgac                                              20

<210> SEQ ID NO 401
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 401
tatagccgtg aacccgatgc                                              20

<210> SEQ ID NO 402
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 402
tatgatcgga caccacgcag                                              20

<210> SEQ ID NO 403
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 403
tgagagcgga ccatacgatc                                              20

<210> SEQ ID NO 404
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 404
gctcagagaa cactacgtga                                              20

<210> SEQ ID NO 405
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 405
ctatgacgga gcagataccg                                              20

<210> SEQ ID NO 406
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 406
gcatatagag tcgcataagg                                              20

<210> SEQ ID NO 407
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 407
ttacgacgac tcgctaattg                                              20

<210> SEQ ID NO 408
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 408
ttgcgaagac cagcgaacac                                               20

<210> SEQ ID NO 409
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 409
ttggcgggac cagctattct                                               20

<210> SEQ ID NO 410
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 410
tgaggcagac cctatcacag                                               20

<210> SEQ ID NO 411
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 411
ctagcgcgac ttggatcatt                                               20

<210> SEQ ID NO 412
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 412
ctgatgcgac tcctagactt                                               20

<210> SEQ ID NO 413
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 413
cgacgatgct tatagactct                                               20

<210> SEQ ID NO 414
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 414
```
gagcgtcgat gattatctgt                               20

<210> SEQ ID NO 415
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 415
gaggatcgag tctcatagat                               20

<210> SEQ ID NO 416
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 416
tgagcgtgct agacctctgt                               20

<210> SEQ ID NO 417
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 417
tacgatggtc gatctggctt                               20

<210> SEQ ID NO 418
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 418
atacgtggac aagcggtcta                               20

<210> SEQ ID NO 419
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 419
catagcggca aagcgcgtaa                               20

<210> SEQ ID NO 420
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 420
ctacgctgat gacgctgttt                               20

<210> SEQ ID NO 421
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 421
acggacctct gacgtgttgt                                               20

<210> SEQ ID NO 422
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 422
gactgcatct caagtgttac                                               20

<210> SEQ ID NO 423
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 423
gacactctcg aactgtaggc                                               20

<210> SEQ ID NO 424
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 424
tggactctca taacggcgtc                                               20

<210> SEQ ID NO 425
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 425
aacagtctcc aagaggcgta                                               20

<210> SEQ ID NO 426
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 426
atcagtgtcc taagtgcgcg                                               20

<210> SEQ ID NO 427
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 427
aagagtgtct aagtctcgcg                                               20
```

<210> SEQ ID NO 428
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 428
aatcgactgt aagtatcgcg                                           20

<210> SEQ ID NO 429
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 429
catatagtgt aatggagccg                                           20

<210> SEQ ID NO 430
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 430
atagaagtat aagtgcgccg                                           20

<210> SEQ ID NO 431
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 431
atagccttct aagagcggcg                                           20

<210> SEQ ID NO 432
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 432
cactctctct aagatggtag                                           20

<210> SEQ ID NO 433
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 433
tctactatca gagggcgtcg                                           20

<210> SEQ ID NO 434
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 434
gataccgtag cattaggtcg                                                  20

<210> SEQ ID NO 435
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 435
tagacggtag cacttagttg                                                  20

<210> SEQ ID NO 436
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 436
agacctgttg aacgcacttc                                                  20

<210> SEQ ID NO 437
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 437
aagactgttg aaccgcattc                                                  20

<210> SEQ ID NO 438
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 438
agagtctgat aactgcgttc                                                  20

<210> SEQ ID NO 439
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 439
acattctgtc aagcgtgtcc                                                  20

<210> SEQ ID NO 440
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 440
agactcggtg aacctgactc                                                  20

<210> SEQ ID NO 441

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 441
atgacacgcg aagcgatacc                                                     20

<210> SEQ ID NO 442
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 442
gatagacgcg aatcacgacc                                                     20

<210> SEQ ID NO 443
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 443
aatgacggtg aatccgcctc                                                     20

<210> SEQ ID NO 444
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 444
attaggcttg cagtccgcgt                                                     20

<210> SEQ ID NO 445
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 445
ctgagagttc gatgacctgt                                                     20

<210> SEQ ID NO 446
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 446
cagatagttt gagacactcg                                                     20

<210> SEQ ID NO 447
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 447
```
cattataggt gaggacatcg                                              20

<210> SEQ ID NO 448
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 448
caatatagac ggtgacagtg                                              20

<210> SEQ ID NO 449
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 449
agctaatgtc gagtcacgct                                              20

<210> SEQ ID NO 450
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 450
cgctcgatgt agagtattct                                              20

<210> SEQ ID NO 451
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 451
aagccgatgt cgatctacct                                              20

<210> SEQ ID NO 452
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 452
atccagattc gacgatactg                                              20

<210> SEQ ID NO 453
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 453
cagctcgtgt cagtcgtatt                                              20

<210> SEQ ID NO 454
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 454
gcgctgatta tgacgtgatt                                               20

<210> SEQ ID NO 455
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 455
cagccgatgt tccagtctgt                                               20

<210> SEQ ID NO 456
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 456
ggccatgcgt tcacagttgt                                               20

<210> SEQ ID NO 457
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 457
gcagcagcgt gtacgattct                                               20

<210> SEQ ID NO 458
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 458
gcagtcacgt tctcgaatcg                                               20

<210> SEQ ID NO 459
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 459
gcgctaacct ttcagaatac                                               20

<210> SEQ ID NO 460
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 460
gaagcacctt tcacgaagtc                                               20
```

```
<210> SEQ ID NO 461
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 461
agagagacgt tgcccaagtc                                              20

<210> SEQ ID NO 462
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 462
tataacacgg tagccaaggc                                              20

<210> SEQ ID NO 463
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 463
tactcatcgg tagccagtgg                                              20

<210> SEQ ID NO 464
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 464
atcatgtccc aagcgcggta                                              20

<210> SEQ ID NO 465
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 465
atatgcaccg aaggcgctac                                              20

<210> SEQ ID NO 466
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 466
tatatgacgt aagacggcag                                              20

<210> SEQ ID NO 467
<211> LENGTH: 20
<212> TYPE: DNA
<213> ORGANISM: Artificial Sequence
<220> FEATURE:
```

```
<223> OTHER INFORMATION: synthetic oligonucleotide

<400> SEQUENCE: 467
gtttatacga aagaaggcgc                                                      20

<210> SEQ ID NO 468
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 468
gatctaacgc acgggaactc                                                      20

<210> SEQ ID NO 469
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 469
atctcagctc ggaggacact                                                      20

<210> SEQ ID NO 470
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 470
gatcacactt acggaacagc                                                      20

<210> SEQ ID NO 471
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 471
cgccaaccgt actggaaata                                                      20

<210> SEQ ID NO 472
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 472
ccctgcactt tgcgtaatat                                                      20

<210> SEQ ID NO 473
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 473
caaagcacag tccgtaatct                                                      20
```

```
<210> SEQ ID NO 474
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 474
aaatgctcag tgccgtaagt                                               20

<210> SEQ ID NO 475
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 475
aatactacgt cacggaggtg                                               20

<210> SEQ ID NO 476
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 476
attaccgctc cagtgtggtg                                               20

<210> SEQ ID NO 477
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 477
tatcaggcat cacgtagagg                                               20

<210> SEQ ID NO 478
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 478
atgctgtcat aagctaggag                                               20

<210> SEQ ID NO 479
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 479
cagcatactg aacgagaggc                                               20

<210> SEQ ID NO 480
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 480
atcatatcag gcagaggacg                                                    20

<210> SEQ ID NO 481
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 481
aatctagcct aatgtgcgag                                                    20

<210> SEQ ID NO 482
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 482
aatcacgcgg aaggcatagc                                                    20

<210> SEQ ID NO 483
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 483
aactcagcgg aatggatagc                                                    20

<210> SEQ ID NO 484
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 484
atactagcag cacggtgtag                                                    20

<210> SEQ ID NO 485
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 485
atctagcctg acggatgagt                                                    20

<210> SEQ ID NO 486
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 486
ctacttgagt gacggatagt                                                    20

<210> SEQ ID NO 487
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 487
ctactgttga gagcggtatt                                                    20

<210> SEQ ID NO 488
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 488
tatgtcgtag cacggatttg                                                    20

<210> SEQ ID NO 489
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 489
catctgatac caggattgcg                                                    20

<210> SEQ ID NO 490
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 490
gattgcataa cagcgtagcc                                                    20

<210> SEQ ID NO 491
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 491
gatgcgatac cctgcgatct                                                    20

<210> SEQ ID NO 492
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 492
acgacgatac caggtctgtc                                                    20

<210> SEQ ID NO 493
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 493
```
aagcgagtag cacgttcgtc                                              20

<210> SEQ ID NO 494
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 494
actgatgtag caggcccgat                                              20

<210> SEQ ID NO 495
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 495
taagggttac gaacatcgcc                                              20

<210> SEQ ID NO 496
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 496
tcgtaagtaa gaagatcggc                                              20

<210> SEQ ID NO 497
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 497
cgtatgatcg aatagtagcc                                              20

<210> SEQ ID NO 498
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 498
cagttattac cagataggcg                                              20

<210> SEQ ID NO 499
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 499
tagtggctac cagatcaccg                                              20

<210> SEQ ID NO 500
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 500
tatttgctac caggcgcacg                                                    20

<210> SEQ ID NO 501
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 501
atagtgatac cagctcgccg                                                    20

<210> SEQ ID NO 502
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 502
tatgtcgtac cactgagccg                                                    20

<210> SEQ ID NO 503
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 503
ttatgcgaac cactgggcac                                                    20

<210> SEQ ID NO 504
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 504
tatattggac ccagcggcag                                                    20

<210> SEQ ID NO 505
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 505
tatgattgac gactgcgtgt                                                    20

<210> SEQ ID NO 506
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 506
tattgctgac catcggctcg                                                    20
```

```
<210> SEQ ID NO 507
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 507
atagtgtcac cacaggtcgc                                               20

<210> SEQ ID NO 508
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 508
tatattagac cagaggtggc                                               20

<210> SEQ ID NO 509
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 509
attatacgac cacagggcgc                                               20

<210> SEQ ID NO 510
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 510
aatatacgat tacgcgctcg                                               20

<210> SEQ ID NO 511
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 511
gagttacgca cctacagtcg                                               20

<210> SEQ ID NO 512
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 512
gattagagcc acctagtcgc                                               20

<210> SEQ ID NO 513
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 513
tgtgagcgac aaccaacgca                                               20

<210> SEQ ID NO 514
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 514
gggtatcgaa caccagacac                                               20

<210> SEQ ID NO 515
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 515
aagattacgg aacccgatcc                                               20

<210> SEQ ID NO 516
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 516
atgtacggaa cctcgatgcc                                               20

<210> SEQ ID NO 517
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 517
aatgaacgag accgcgtgac                                               20

<210> SEQ ID NO 518
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 518
atgtactgag caccaccgag                                               20

<210> SEQ ID NO 519
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 519
atgtagcgac tcaccactgg                                               20

<210> SEQ ID NO 520
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 520
tttagccgga tcaccgtgtg                                                     20

<210> SEQ ID NO 521
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 521
ttaatacgga tgcccagagg                                                     20

<210> SEQ ID NO 522
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 522
ataagtcgta ggaatgtcgc                                                     20

<210> SEQ ID NO 523
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 523
ttataccgta ggacgtgctg                                                     20

<210> SEQ ID NO 524
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 524
ttagaccgta gcacgccttg                                                     20

<210> SEQ ID NO 525
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 525
atagactgct accagcgtcg                                                     20

<210> SEQ ID NO 526
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 526
```

```
taactcgtac tagcgatctg                                              20

<210> SEQ ID NO 527
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 527
gaaggcgtac taagcatctc                                              20

<210> SEQ ID NO 528
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 528
agcacgagca tcatagattc                                              20

<210> SEQ ID NO 529
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 529
aatccgagtg catcgcagtg                                              20

<210> SEQ ID NO 530
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 530
tacgcgagtg catgtgccat                                              20

<210> SEQ ID NO 531
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 531
actgagcgat gcagcgtcat                                              20

<210> SEQ ID NO 532
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 532
tcacggcgct catggatcat                                              20

<210> SEQ ID NO 533
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 533
atacgaggct catgcgtcat                                            20

<210> SEQ ID NO 534
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 534
aaagacagct catgcactcg                                            20

<210> SEQ ID NO 535
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 535
ctagagcgat gtatcatgtg                                            20

<210> SEQ ID NO 536
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 536
cgagactgtc gcatgatgat                                            20

<210> SEQ ID NO 537
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 537
catagatgct gagctgctgt                                            20

<210> SEQ ID NO 538
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 538
tcctagtgag gcacatgatg                                            20

<210> SEQ ID NO 539
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 539
tctcagagtc gagcatgatg                                            20
```

```
<210> SEQ ID NO 540
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 540
gtcttaatgc tcgatcagtg                                               20

<210> SEQ ID NO 541
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 541
tcagagatca tggcacagag                                               20

<210> SEQ ID NO 542
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 542
ggtacagaca ctgcgacaac                                               20

<210> SEQ ID NO 543
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 543
tatagctcca ccagagtatc                                               20

<210> SEQ ID NO 544
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 544
atttacgcaa cagcggctta                                               20

<210> SEQ ID NO 545
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 545
tcatagggat catgccgttg                                               20

<210> SEQ ID NO 546
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 546
tatcagttag catgacgcgg 20

<210> SEQ ID NO 547
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 547
atcactgttc gagcagcgtg 20

<210> SEQ ID NO 548
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 548
gcatagttat cagtgtgcgt 20

<210> SEQ ID NO 549
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 549
gcatcgtttc aagcgtctgc 20

<210> SEQ ID NO 550
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 550
catactcttg aagcgatgtc 20

<210> SEQ ID NO 551
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 551
atcagtcgtg cattgcggct 20

<210> SEQ ID NO 552
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 552
gactgctgct catatcgagt 20

```
<210> SEQ ID NO 553
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 553
aagcattgcg aatcatagcc                                              20

<210> SEQ ID NO 554
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 554
acgatcagga tacatactgc                                              20

<210> SEQ ID NO 555
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 555
tattatcaga catcgcacgc                                              20

<210> SEQ ID NO 556
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 556
caatacatat catgcgagcg                                              20

<210> SEQ ID NO 557
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 557
atatctccag catctgagcg                                              20

<210> SEQ ID NO 558
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 558
atactgacag cacgcatggc                                              20

<210> SEQ ID NO 559
<211> LENGTH: 20
<212> TYPE: DNA
<213> ORGANISM: Artificial Sequence
<220> FEATURE:
<223> OTHER INFORMATION: synthetic oligonucleotide
```

-continued

```
<400> SEQUENCE: 559
gacatatcag catacatggc                                              20

<210> SEQ ID NO 560
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 560
atagtcacca catagatcgc                                              20

<210> SEQ ID NO 561
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 561
tacgtcatca catggatctc                                              20

<210> SEQ ID NO 562
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 562
gataaggtca cagagactgc                                              20

<210> SEQ ID NO 563
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 563
tataggctca catgcgcgtc                                              20

<210> SEQ ID NO 564
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 564
agagtgctca catcgctgtc                                              20

<210> SEQ ID NO 565
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 565
gatagactga tccgcagatg                                              20

<210> SEQ ID NO 566
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 566
tatcaccgag catcagcgag                                              20

<210> SEQ ID NO 567
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 567
tcactacgtg catcagcgtg                                              20

<210> SEQ ID NO 568
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 568
tatatgcgag cacaggatgc                                              20

<210> SEQ ID NO 569
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 569
tcatatcagt gcagcagcgg                                              20

<210> SEQ ID NO 570
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 570
tatagagcag cagcactggc                                              20

<210> SEQ ID NO 571
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 571
ttatagccga gcacactgcg                                              20

<210> SEQ ID NO 572
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 572
```
tttaggcgta gcactcgctg 20

<210> SEQ ID NO 573
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 573
ctacagtgct agacagccag 20

<210> SEQ ID NO 574
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 574
cagtcgagta catgcaccag 20

<210> SEQ ID NO 575
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 575
tcttatagta gatgcagcgg 20

<210> SEQ ID NO 576
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 576
cctatacgct aatgtcagag 20

<210> SEQ ID NO 577
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 577
catccgagct aatgtatcag 20

<210> SEQ ID NO 578
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 578
aataggcgct aagctgatag 20

<210> SEQ ID NO 579
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 579
agatcccgcg tcaggcatat                                               20

<210> SEQ ID NO 580
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 580
agctaccgag tcgatctgat                                               20

<210> SEQ ID NO 581
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 581
gcaccgtgat ccagtatatg                                               20

<210> SEQ ID NO 582
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 582
acctcgtgta gcatgttgtg                                               20

<210> SEQ ID NO 583
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 583
tccacgggat acagtctgag                                               20

<210> SEQ ID NO 584
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 584
catagcagat gcacgttgag                                               20

<210> SEQ ID NO 585
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 585
gtacacagat acgcgctcag                                               20
```

<210> SEQ ID NO 586
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 586
tagatcagag catcggacag                                               20

<210> SEQ ID NO 587
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 587
atataacgat cacggcagtg                                               20

<210> SEQ ID NO 588
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 588
tatgagcgca cagtctcgtc                                               20

<210> SEQ ID NO 589
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 589
ttatcgagca cagtgtcggc                                               20

<210> SEQ ID NO 590
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 590
tatatccgca cagcgtggtc                                               20

<210> SEQ ID NO 591
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 591
acatcccgat caggtgactg                                               20

<210> SEQ ID NO 592
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 592
agatccggcc aactgagcta                                          20

<210> SEQ ID NO 593
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 593
ttgccgtgca tccgatagct                                          20

<210> SEQ ID NO 594
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 594
ttgtcacgca tctccagagg                                          20

<210> SEQ ID NO 595
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 595
atatcacgct cgacagtgcg                                          20

<210> SEQ ID NO 596
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 596
aattacagcg actcgatgcg                                          20

<210> SEQ ID NO 597
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 597
atgtactgcc acgcatatcg                                          20

<210> SEQ ID NO 598
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 598
tagagacgac tcacatacgc                                          20

<210> SEQ ID NO 599
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 599
gagcagcgac gacattcatc                                                  20

<210> SEQ ID NO 600
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 600
gctaatcgaa cacagctcta                                                  20

<210> SEQ ID NO 601
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 601
gacatacgca cataggctac                                                  20

<210> SEQ ID NO 602
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 602
gggattcgcc acaacataca                                                  20

<210> SEQ ID NO 603
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 603
atggctcgca cctgagtcat                                                  20

<210> SEQ ID NO 604
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 604
taggccagca tccgacatag                                                  20

<210> SEQ ID NO 605
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 605
```

```
gcgcacagct cattacatag                                              20

<210> SEQ ID NO 606
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 606
gagacacgta gagacatcgc                                              20

<210> SEQ ID NO 607
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 607
aagtagcgtc aatgtcagcc                                              20

<210> SEQ ID NO 608
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 608
ccgatacgtg catattgtgg                                              20

<210> SEQ ID NO 609
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 609
ccatcgcgtg aattatgctc                                              20

<210> SEQ ID NO 610
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 610
ccagcgagga gctatgatat                                              20

<210> SEQ ID NO 611
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 611
ctcggatagt gcatgatatg                                              20

<210> SEQ ID NO 612
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 612
cgagatcagt gcatagcatg                                              20

<210> SEQ ID NO 613
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 613
ctcatacgtc gagctggatg                                              20

<210> SEQ ID NO 614
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 614
tccctacgtc tgatgacatt                                              20

<210> SEQ ID NO 615
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 615
gacatacgtc tgaactgatc                                              20

<210> SEQ ID NO 616
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 616
atacaccggc ataatctgtc                                              20

<210> SEQ ID NO 617
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 617
gtgccatgtg cataacgctc                                              20

<210> SEQ ID NO 618
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 618
agtggcagtg catctagcct                                              20
```

<210> SEQ ID NO 619
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 619
aattctggtg cagccgctct                                              20

<210> SEQ ID NO 620
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 620
tattggcgct gcacctgtct                                              20

<210> SEQ ID NO 621
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 621
aatggtcgct cagtcctgct                                              20

<210> SEQ ID NO 622
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 622
tagtgacgct cagatccctg                                              20

<210> SEQ ID NO 623
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 623
tagtaacgtc gatgacagcg                                              20

<210> SEQ ID NO 624
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 624
actacaccgc tataatgcag                                              20

<210> SEQ ID NO 625
<211> LENGTH: 20
<212> TYPE: DNA
<213> ORGANISM: Artificial Sequence
<220> FEATURE:

-continued

<223> OTHER INFORMATION: synthetic oligonucleotide

<400> SEQUENCE: 625
acatacgcga catggagcag                                                    20

<210> SEQ ID NO 626
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 626
tagtacgcag catctggacg                                                    20

<210> SEQ ID NO 627
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 627
ctatacgcag gcatgagacg                                                    20

<210> SEQ ID NO 628
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 628
tagcactgga catagatgag                                                    20

<210> SEQ ID NO 629
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 629
ttagcctgca cactagcgag                                                    20

<210> SEQ ID NO 630
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 630
tgactatgca gatacgctgg                                                    20

<210> SEQ ID NO 631
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 631
cagctatgag cactctgtgg                                                    20

```
<210> SEQ ID NO 632
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 632
atcacctggc agatcggatg                                               20

<210> SEQ ID NO 633
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 633
gatacacgag tcacaggcag                                               20

<210> SEQ ID NO 634
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 634
cagtaacgat gtatccacag                                               20

<210> SEQ ID NO 635
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 635
ggtccacgat aacatgacac                                               20

<210> SEQ ID NO 636
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 636
tgacacggat gcaagaccac                                               20

<210> SEQ ID NO 637
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 637
attgaccgag aactcatcac                                               20

<210> SEQ ID NO 638
<211> LENGTH: 20
<212> TYPE: DNA
<213> ORGANISM: Artificial Sequence
<220> FEATURE:
<223> OTHER INFORMATION: synthetic oligonucleotide
```

-continued

<400> SEQUENCE: 638
atagaccgat aagcagccgc                                           20

<210> SEQ ID NO 639
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 639
aagtagcgat catcacgccg                                           20

<210> SEQ ID NO 640
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 640
aagcgacgag cattgaccag                                           20

<210> SEQ ID NO 641
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 641
atgccacgag gatgcactag                                           20

<210> SEQ ID NO 642
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 642
acctactgag gagacgcatg                                           20

<210> SEQ ID NO 643
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 643
tgcactagga tcagtcgctg                                           20

<210> SEQ ID NO 644
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 644
tagctcaggc tcagacgcat                                           20

<210> SEQ ID NO 645
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 645
caatccaggc tatatcgctg                                              20

<210> SEQ ID NO 646
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 646
tctgacagca aatacgctca                                              20

<210> SEQ ID NO 647
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 647
catacatgat gagctgaggt                                              20

<210> SEQ ID NO 648
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 648
atcgcaggat ggtacagcat                                              20

<210> SEQ ID NO 649
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 649
tatagcggtg catcttcagt                                              20

<210> SEQ ID NO 650
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 650
tttagcggag agcctcgcat                                              20

<210> SEQ ID NO 651
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 651
```
tgagaacgag cagcttccac                                              20

<210> SEQ ID NO 652
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 652
tggattcgac tcgctcgcat                                              20

<210> SEQ ID NO 653
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 653
cgttatcgca gctacggcat                                              20

<210> SEQ ID NO 654
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 654
taccgtagag tcagcggcat                                              20

<210> SEQ ID NO 655
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 655
caatgtagag gatcgtgcat                                              20

<210> SEQ ID NO 656
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 656
cccgttagac tatctgctat                                              20

<210> SEQ ID NO 657
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 657
gagccttgca cctatgctat                                              20

<210> SEQ ID NO 658
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 658
cacctgtgac tacatgctag                                               20

<210> SEQ ID NO 659
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 659
cagcgatgac tatatctgag                                               20

<210> SEQ ID NO 660
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 660
acgagatgac tagctgattg                                               20

<210> SEQ ID NO 661
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 661
acgcagtgag tagcatcctg                                               20

<210> SEQ ID NO 662
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 662
aagtcgtgcg aatcttctgc                                               20

<210> SEQ ID NO 663
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 663
atgacgagtg ccatcctctg                                               20

<210> SEQ ID NO 664
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 664
gatccgagaa catcactcta                                               20
```

<210> SEQ ID NO 665
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 665
attcgcagac cagcagtgtc                                                  20

<210> SEQ ID NO 666
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 666
catgttagtg aatgcgagtc                                                  20

<210> SEQ ID NO 667
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 667
ccctttagat aacgatgctc                                                  20

<210> SEQ ID NO 668
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 668
actcgacgat aacgtgcatc                                                  20

<210> SEQ ID NO 669
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 669
actgaataga catgacggcc                                                  20

<210> SEQ ID NO 670
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 670
gctaatgaga cataggccgc                                                  20

<210> SEQ ID NO 671
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 671
cgacatgata catacgactc                                              20

<210> SEQ ID NO 672
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 672
acgtgtgcaa cattcgagcc                                              20

<210> SEQ ID NO 673
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 673
tagcggtcac cattacgcag                                              20

<210> SEQ ID NO 674
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 674
tacgaagcac catgtgggac                                              20

<210> SEQ ID NO 675
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 675
tacctaacga catttgtggc                                              20

<210> SEQ ID NO 676
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 676
atagcgcgat aacgtcggtc                                              20

<210> SEQ ID NO 677
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 677
tactcgcgtt gacatcgggt                                              20

<210> SEQ ID NO 678
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 678
cactgtggac gatacggtct                                             20

<210> SEQ ID NO 679
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 679
cacgcttgac catcttaggg                                             20

<210> SEQ ID NO 680
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 680
aactgatgct aacgtaggag                                             20

<210> SEQ ID NO 681
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 681
gccacacgta ccaataggga                                             20

<210> SEQ ID NO 682
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 682
ccatcacgtt tcagaagtac                                             20

<210> SEQ ID NO 683
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 683
atatacgggt aaccagccgc                                             20

<210> SEQ ID NO 684
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 684
```
aatagaggtc aaccgagccc                    20

<210> SEQ ID NO 685
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 685
aattagggtc aacgacgccc                    20

<210> SEQ ID NO 686
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 686
atttagcgac gaggataccg                    20

<210> SEQ ID NO 687
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 687
tatagcagac gacgttcgcc                    20

<210> SEQ ID NO 688
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 688
atgaccgaca gacgtttgcc                    20

<210> SEQ ID NO 689
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 689
acacacgagt aacatttgcc                    20

<210> SEQ ID NO 690
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 690
gacagcgagt aatttcttgc                    20

<210> SEQ ID NO 691
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 691
aacacgcagt aattccgagc                                              20

<210> SEQ ID NO 692
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 692
tactagcact catacgacgg                                              20

<210> SEQ ID NO 693
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 693
atagccgact aacgagcgtc                                              20

<210> SEQ ID NO 694
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 694
aagagctatc gaacgacgcc                                              20

<210> SEQ ID NO 695
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 695
aagccaaacg aacttgcggc                                              20

<210> SEQ ID NO 696
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 696
gccctatacg aacatttgac                                              20

<210> SEQ ID NO 697
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 697
ccttgatacg aagcagttac                                              20
```

<210> SEQ ID NO 698
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 698
cacagcgacg aacgtgatac                                          20

<210> SEQ ID NO 699
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 699
ccatgatacc aacgtgtcta                                          20

<210> SEQ ID NO 700
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 700
tgcccgaaga gtaaagttca                                          20

<210> SEQ ID NO 701
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 701
ctccgataag cgaagaggac                                          20

<210> SEQ ID NO 702
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 702
cgcctataac gagagagacc                                          20

<210> SEQ ID NO 703
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 703
cgcccggaca tataaggaac                                          20

<210> SEQ ID NO 704
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 704
ccgcgacatt aagtcaagac                                              20

<210> SEQ ID NO 705
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 705
gctcgacatt aacagactac                                              20

<210> SEQ ID NO 706
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 706
ggcatacgag aatagcccac                                              20

<210> SEQ ID NO 707
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 707
ggatagcacg aagacctcac                                              20

<210> SEQ ID NO 708
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 708
tctgaagacg aagccacgac                                              20

<210> SEQ ID NO 709
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 709
tcgcaggacg aagactagac                                              20

<210> SEQ ID NO 710
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 710
tgcggacacg aataccagac                                              20

```
<210> SEQ ID NO 711
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 711
tcggcgcggt aaacacaaca                                               20

<210> SEQ ID NO 712
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 712
ggctccacta aatagacgca                                               20

<210> SEQ ID NO 713
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 713
ggcctctcat aagacagaac                                               20

<210> SEQ ID NO 714
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 714
gcgctcggat aacataacac                                               20

<210> SEQ ID NO 715
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 715
gccgccggat acagaataac                                               20

<210> SEQ ID NO 716
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 716
gcgcgaagat taggcaacac                                               20

<210> SEQ ID NO 717
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 717
cgcgtaagag tatagtacag                                              20

<210> SEQ ID NO 718
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 718
ctgggccgag aatcaaacga                                              20

<210> SEQ ID NO 719
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 719
ggcggctgcc aacataacaa                                              20

<210> SEQ ID NO 720
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 720
tgcgtccgcc aatcaataaa                                              20

<210> SEQ ID NO 721
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 721
gctgtccgag aagcacaaac                                              20

<210> SEQ ID NO 722
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 722
gcggacagcg aactaatcac                                              20

<210> SEQ ID NO 723
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 723
gcgactatcg aaccatatac                                              20

<210> SEQ ID NO 724
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 724
tgcactagca gaacttacac                                               20

<210> SEQ ID NO 725
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 725
gcactcagag aagtatccac                                               20

<210> SEQ ID NO 726
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 726
cggtcccgaa actatatcaa                                               20

<210> SEQ ID NO 727
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 727
gggccgcgta aaccataaca                                               20

<210> SEQ ID NO 728
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 728
gctctccgta aacgcaaaga                                               20

<210> SEQ ID NO 729
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 729
cgtggcgata atacgaaagc                                               20

<210> SEQ ID NO 730
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 730
```

```
gatcatgtgc tctaagacgg                                              20
```

<210> SEQ ID NO 731
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 731

```
cgagagatcg tattacatgg                                              20
```

<210> SEQ ID NO 732
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 732

```
gcgacgatag tagtacatag                                              20
```

<210> SEQ ID NO 733
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 733

```
ccgtcgctac aaggacaaga                                              20
```

<210> SEQ ID NO 734
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 734

```
cctgtcctac aacgaataga                                              20
```

<210> SEQ ID NO 735
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 735

```
caggtcctag aatcgaatac                                              20
```

<210> SEQ ID NO 736
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 736

```
cggtacgaag aagcgattta                                              20
```

<210> SEQ ID NO 737
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 737
gcgtagcaac taactcgata                                                     20

<210> SEQ ID NO 738
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 738
gggtctcacc tacgctatat                                                     20

<210> SEQ ID NO 739
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 739
gagttacacg aagcctctac                                                     20

<210> SEQ ID NO 740
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 740
agacttcacg aactgcttac                                                     20

<210> SEQ ID NO 741
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 741
acatggcacg aagctattac                                                     20

<210> SEQ ID NO 742
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 742
atacggcacg acaggcttag                                                     20

<210> SEQ ID NO 743
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 743
aattagcact gacggcctcg                                                     20
```

```
<210> SEQ ID NO 744
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 744
agttacccac gagctgtcag                                                     20

<210> SEQ ID NO 745
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 745
taatccgcac gagctgctag                                                     20

<210> SEQ ID NO 746
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 746
atatccgcag cagactggag                                                     20

<210> SEQ ID NO 747
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 747
gatacctctc gatatgcgcg                                                     20

<210> SEQ ID NO 748
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 748
atagcttcac gatgagcgat                                                     20

<210> SEQ ID NO 749
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 749
actacaccac gatgtgaatc                                                     20

<210> SEQ ID NO 750
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 750
tctgaccgac gagctagatg                                              20

<210> SEQ ID NO 751
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 751
ttgcaccata ccagatacag                                              20

<210> SEQ ID NO 752
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 752
tgacgtgaac gagcttctgc                                              20

<210> SEQ ID NO 753
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 753
atgtatagcg acggcctctc                                              20

<210> SEQ ID NO 754
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 754
gaatatagag cacgactccc                                              20

<210> SEQ ID NO 755
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 755
aagcgttacg aagcgttccc                                              20

<210> SEQ ID NO 756
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 756
acacgagagt aacggacctc                                              20

<210> SEQ ID NO 757

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 757
agacgtagcg aactagaccc                                                 20

<210> SEQ ID NO 758
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 758
cagtgcatgt aacctaagtc                                                 20

<210> SEQ ID NO 759
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 759
acagcgatgg aacttacggc                                                 20

<210> SEQ ID NO 760
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 760
aactgtgtgg aattagcccg                                                 20

<210> SEQ ID NO 761
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 761
atacgtcggt aactagcccg                                                 20

<210> SEQ ID NO 762
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 762
atatgtcggg aacctaccgc                                                 20

<210> SEQ ID NO 763
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 763
```
atacttcggg aaccgtaggc                                           20

<210> SEQ ID NO 764
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 764
attctactgg accgcgttgg                                           20

<210> SEQ ID NO 765
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 765
aatcactagg tacggcctgg                                           20

<210> SEQ ID NO 766
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 766
atatgctagt acacggtcgg                                           20

<210> SEQ ID NO 767
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 767
aaagctaggt tcacgttggt                                           20

<210> SEQ ID NO 768
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 768
gcatactcgt caccgttagt                                           20

<210> SEQ ID NO 769
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 769
cgatacctgt acctagttgt                                           20

<210> SEQ ID NO 770
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 770
cgactctagt tcacggaatt                                               20

<210> SEQ ID NO 771
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 771
taacgccagg tcccgtaatg                                               20

<210> SEQ ID NO 772
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 772
taacggcacc ttccgaattg                                               20

<210> SEQ ID NO 773
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 773
tagaccgagt taccgcgttg                                               20

<210> SEQ ID NO 774
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 774
attgcagagt ccacccgttg                                               20

<210> SEQ ID NO 775
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 775
gtgagcgaaa caccgcgtaa                                               20

<210> SEQ ID NO 776
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 776
tgacatgaag aaccggccac                                               20
```

<210> SEQ ID NO 777
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 777
aagtgagacg aaccgcctac                                              20

<210> SEQ ID NO 778
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 778
atcgagcacg taaccgttgc                                              20

<210> SEQ ID NO 779
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 779
catttgcagt aagtcggtag                                              20

<210> SEQ ID NO 780
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 780
cagtctgagt aatccgttag                                              20

<210> SEQ ID NO 781
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 781
cgggtgtaga aaccgactaa                                              20

<210> SEQ ID NO 782
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 782
ccgcttgaaa cacgtactaa                                              20

<210> SEQ ID NO 783
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 783
ccacgcgaag aacggattta                                                    20

<210> SEQ ID NO 784
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 784
ccacgcgaga aatcggttaa                                                    20

<210> SEQ ID NO 785
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 785
cctcaagcga aacggttaca                                                    20

<210> SEQ ID NO 786
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 786
tctcagccga aagagggtaa                                                    20

<210> SEQ ID NO 787
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 787
cactgacttc gaggtcgtgt                                                    20

<210> SEQ ID NO 788
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 788
acagctatta ggacgtgttg                                                    20

<210> SEQ ID NO 789
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 789
cactactgag cagacgttcg                                                    20

```
<210> SEQ ID NO 790
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 790
cctcagcgat cataggtagg                                                  20

<210> SEQ ID NO 791
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 791
catctacgga cacggtatcg                                                  20

<210> SEQ ID NO 792
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 792
atatgcccta cacggtcagg                                                  20

<210> SEQ ID NO 793
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 793
atcactctta ccaggctagg                                                  20

<210> SEQ ID NO 794
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 794
atcactcgta cagcggtagg                                                  20

<210> SEQ ID NO 795
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 795
tcatgctgct aacggtcgag                                                  20

<210> SEQ ID NO 796
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 796
tagtctagta catcggtagg                                                   20

<210> SEQ ID NO 797
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 797
ataatcgggc ttaacgacgg                                                   20

<210> SEQ ID NO 798
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 798
gagacccttg taacgatccg                                                   20

<210> SEQ ID NO 799
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 799
tacctagtag taacggcgag                                                   20

<210> SEQ ID NO 800
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 800
acctagcgtc gatacgtggt                                                   20

<210> SEQ ID NO 801
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 801
aacctatgtg gacacgtcgg                                                   20

<210> SEQ ID NO 802
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 802
aataccggct aaccgtagag                                                   20

<210> SEQ ID NO 803
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 803
agcgttgcta cacggtatat                                          20

<210> SEQ ID NO 804
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 804
tatgctgctg cacccgtagt                                          20

<210> SEQ ID NO 805
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 805
gcatgacaca cacctagtta                                          20

<210> SEQ ID NO 806
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 806
catgcaacga acctagtcga                                          20

<210> SEQ ID NO 807
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 807
ctatgcgcta gacgtagttg                                          20

<210> SEQ ID NO 808
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 808
tacttcgcta gacgggtgct                                          20

<210> SEQ ID NO 809
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 809
```
atcttccgta gagccggtgt 20

<210> SEQ ID NO 810
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 810
aactatcgct tcaggcgttt 20

<210> SEQ ID NO 811
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 811
taggtgagtc cacgtaccct 20

<210> SEQ ID NO 812
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 812
atgcgctgtc gaggtacttt 20

<210> SEQ ID NO 813
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 813
agcgatagtg gtgtccattt 20

<210> SEQ ID NO 814
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 814
agctgacccg tcgtactgtt 20

<210> SEQ ID NO 815
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 815
accgagacgg acgtactttc 20

<210> SEQ ID NO 816
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 816
tagcacacgg tcgaatttcc                                               20

<210> SEQ ID NO 817
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 817
agcacacgta ggaactatcc                                               20

<210> SEQ ID NO 818
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 818
cacacagtat aagacttgcc                                               20

<210> SEQ ID NO 819
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 819
cagcgcgtac tagactggat                                               20

<210> SEQ ID NO 820
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 820
cagcatcgaa catacgtgta                                               20

<210> SEQ ID NO 821
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 821
ccgcagagag tataagagtc                                               20

<210> SEQ ID NO 822
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 822
gcggcaagta aacgcactca                                               20
```

<210> SEQ ID NO 823
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 823
gcatagcgta taagcgattc                                          20

<210> SEQ ID NO 824
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 824
gcacagccta aatagtctca                                          20

<210> SEQ ID NO 825
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 825
acagaccsta aagcgtgtca                                          20

<210> SEQ ID NO 826
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 826
gccacaccta aatgtagtca                                          20

<210> SEQ ID NO 827
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 827
gtcacacctt aacaagtgca                                          20

<210> SEQ ID NO 828
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 828
gctacagcta aagcacgtca                                          20

<210> SEQ ID NO 829
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 829
cacgacgcta aatgtcttca                                              20

<210> SEQ ID NO 830
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 830
cactagcgat aagttctgtc                                              20

<210> SEQ ID NO 831
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 831
cataatggcg aattggcgta                                              20

<210> SEQ ID NO 832
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 832
ataagcctac tgagtcgcat                                              20

<210> SEQ ID NO 833
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 833
tacagcctca cagagtgttc                                              20

<210> SEQ ID NO 834
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 834
cagactatca tacagtggtc                                              20

<210> SEQ ID NO 835
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 835
atagctgtcg aattgcgtgc                                              20

<210> SEQ ID NO 836
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 836
aatcgtgtcg aagctatggc                                               20

<210> SEQ ID NO 837
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 837
atatccgtcg aagtgtgcgc                                               20

<210> SEQ ID NO 838
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 838
agacacctcg aagatgatcc                                               20

<210> SEQ ID NO 839
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 839
tatacccgct gaggctgtgt                                               20

<210> SEQ ID NO 840
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 840
tataccggat ggagctgtct                                               20

<210> SEQ ID NO 841
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 841
actactagcg agagctgtcg                                               20

<210> SEQ ID NO 842
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 842
```
catcttagag caggctgacg                                              20

<210> SEQ ID NO 843
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 843
acgactagat catggtagcg                                              20

<210> SEQ ID NO 844
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 844
tcactatgct cagggatgtg                                              20

<210> SEQ ID NO 845
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 845
aatacgagtt gacgagcatg                                              20

<210> SEQ ID NO 846
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 846
tgacgactta gagctgactg                                              20

<210> SEQ ID NO 847
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 847
actgcacgta gactgagctg                                              20

<210> SEQ ID NO 848
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 848
cacgcacgtc gatctatgtg                                              20

<210> SEQ ID NO 849
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 849
gactgacgtg cattctgttg                                              20

<210> SEQ ID NO 850
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 850
acgcagctat gctcatgtat                                              20

<210> SEQ ID NO 851
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 851
aaacgcctat gagctgtgct                                              20

<210> SEQ ID NO 852
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 852
acacgtctga cagttgcatg                                              20

<210> SEQ ID NO 853
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 853
ttaaccgtct ggagatgctt                                              20

<210> SEQ ID NO 854
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 854
cctccgaaca gagagtctta                                              20

<210> SEQ ID NO 855
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 855
gcgctactaa cacagtctta                                              20
```

```
<210> SEQ ID NO 856
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 856
cgccacgtaa tcaagactta                                              20

<210> SEQ ID NO 857
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 857
cacacgctac caagtatgga                                              20

<210> SEQ ID NO 858
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 858
cagacgcctc aagtagttta                                              20

<210> SEQ ID NO 859
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 859
tctgacgctc cagtcgtttg                                              20

<210> SEQ ID NO 860
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 860
catattacgc aaggccgtta                                              20

<210> SEQ ID NO 861
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 861
tctatcccgc tagggtgtgt                                              20

<210> SEQ ID NO 862
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 862
atattcgcgt cgagtgagtt                                           20

<210> SEQ ID NO 863
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 863
aaatcaccgt ggacgtgcgt                                           20

<210> SEQ ID NO 864
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 864
acttgaccga gtacgtcgtg                                           20

<210> SEQ ID NO 865
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 865
acgatagcgg tacatctcgg                                           20

<210> SEQ ID NO 866
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 866
acacaggcgt taatctctcg                                           20

<210> SEQ ID NO 867
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 867
atcacggcgt tgaatatagg                                           20

<210> SEQ ID NO 868
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 868
atcctcgatg gtaatgtagg                                           20

```
<210> SEQ ID NO 869
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 869
taccactctg gagcagtagg                                              20

<210> SEQ ID NO 870
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 870
tacagctcta gcagcgtagg                                              20

<210> SEQ ID NO 871
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 871
aacacgtcgg aagctagtgc                                              20

<210> SEQ ID NO 872
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 872
caggtcgatg aatgtagatc                                              20

<210> SEQ ID NO 873
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 873
tccagagcta ggaagtaagc                                              20

<210> SEQ ID NO 874
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 874
atactcactg aaggtccggc                                              20

<210> SEQ ID NO 875
<211> LENGTH: 20
<212> TYPE: DNA
<213> ORGANISM: Artificial Sequence
<220> FEATURE:
<223> OTHER INFORMATION: synthetic oligonucleotide
```

-continued

```
<400> SEQUENCE: 875
aattcgccat caggttccgg                                         20

<210> SEQ ID NO 876
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 876
attcaccctg ggagcttcgt                                         20

<210> SEQ ID NO 877
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 877
atcagcctgt catggtccgt                                         20

<210> SEQ ID NO 878
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 878
tcatcgctga gagtgttcgt                                         20

<210> SEQ ID NO 879
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 879
cgactgccaa gacgttcgta                                         20

<210> SEQ ID NO 880
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 880
caactccgag ggatgtcagt                                         20

<210> SEQ ID NO 881
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 881
aattctgtag gacggttcgt                                         20

<210> SEQ ID NO 882
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 882
ctatatgagt acggcctcgg                                               20

<210> SEQ ID NO 883
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 883
ctctcggagt gacgtttcgt                                               20

<210> SEQ ID NO 884
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 884
gcttccgatc aaggtttaac                                               20

<210> SEQ ID NO 885
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 885
atgtccggcc tacgtcgttt                                               20

<210> SEQ ID NO 886
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 886
atttctcgcg tcaccgggtt                                               20

<210> SEQ ID NO 887
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 887
attgcacggt tcccgagtgt                                               20

<210> SEQ ID NO 888
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 888
```

-continued aacttacact agcccggtgg 20

<210> SEQ ID NO 889
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 889
tatttgactc cacgggacgg 20

<210> SEQ ID NO 890
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 890
aatctatcgt acccggtggg 20

<210> SEQ ID NO 891
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 891
ttggtatcca tcccggtctg 20

<210> SEQ ID NO 892
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 892
atttagtctc cacacgggcg 20

<210> SEQ ID NO 893
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 893
tattacttac cacgcgggcg 20

<210> SEQ ID NO 894
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 894
atatcgagta ccacccgagg 20

<210> SEQ ID NO 895
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 895
ataggcggac caccctctaag                                              20

<210> SEQ ID NO 896
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 896
tagtgacatc gctgcatagg                                               20

<210> SEQ ID NO 897
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 897
ggcagctatg tcgatatgct                                               20

<210> SEQ ID NO 898
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 898
ccagcgaatg tcgatcaatc                                               20

<210> SEQ ID NO 899
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 899
gccgcgtaga caatagatca                                               20

<210> SEQ ID NO 900
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 900
gcggcagaac tactatcaac                                               20

<210> SEQ ID NO 901
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 901
ctgcgcgaag tagagacaac                                               20
```

<210> SEQ ID NO 902
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 902
ctgcgcgaat actatacaac                                               20

<210> SEQ ID NO 903
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 903
cgcatatact acgatagacg                                               20

<210> SEQ ID NO 904
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 904
catctcgatt aagtcagacg                                               20

<210> SEQ ID NO 905
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 905
cagcgcgatc tacttaattg                                               20

<210> SEQ ID NO 906
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 906
gacgcgcacc aatctaagga                                               20

<210> SEQ ID NO 907
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 907
gggtcccacg aataaccaga                                               20

<210> SEQ ID NO 908
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 908
gggccgcact tacaaacaga                                           20

<210> SEQ ID NO 909
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 909
cggcccgtca ttaaataaga                                           20

<210> SEQ ID NO 910
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 910
cccgcattat tatacacgag                                           20

<210> SEQ ID NO 911
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 911
ccgctcgtat aatagaagac                                           20

<210> SEQ ID NO 912
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 912
cgactctaat agccgataag                                           20

<210> SEQ ID NO 913
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 913
tcccgtcaca tttcgataag                                           20

<210> SEQ ID NO 914
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 914
cacgagtaag tctcactaag                                           20

<210> SEQ ID NO 915
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 915
tatcaggccg tcacactagg                                              20

<210> SEQ ID NO 916
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 916
ttagtctcac gatacccagg                                              20

<210> SEQ ID NO 917
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 917
tctcgaccac gattacggag                                              20

<210> SEQ ID NO 918
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 918
catgactcac gactattagg                                              20

<210> SEQ ID NO 919
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 919
tctcgtagca gactctaggg                                              20

<210> SEQ ID NO 920
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 920
accttaggcg actatatggg                                              20

<210> SEQ ID NO 921
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 921
```
cctcgtaatc tagcttaacg                                               20

<210> SEQ ID NO 922
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 922
ccggcggata aacgtaacca                                               20

<210> SEQ ID NO 923
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 923
ccgggttcac aattaaacga                                               20

<210> SEQ ID NO 924
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 924
cggcgtttag acgaacaaag                                               20

<210> SEQ ID NO 925
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 925
gcgcgtatag tgccttaatt                                               20

<210> SEQ ID NO 926
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 926
gccagtattg gtaatctagg                                               20

<210> SEQ ID NO 927
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 927
ctcaactgtg gtgaagtacg                                               20

<210> SEQ ID NO 928
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 928
ccgcagtgct ggtaatttcg                                                   20

<210> SEQ ID NO 929
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 929
cggacgtgat ttaagattcg                                                   20

<210> SEQ ID NO 930
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 930
acaccgtatt taagactgcg                                                   20

<210> SEQ ID NO 931
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 931
gcaccggatt taatagatcg                                                   20

<210> SEQ ID NO 932
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 932
atcaggagtc gtaatagtcg                                                   20

<210> SEQ ID NO 933
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 933
cacgcagata cgttaagacg                                                   20

<210> SEQ ID NO 934
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 934
aggcagatac gattagtacg                                                   20
```

```
<210> SEQ ID NO 935
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 935
gggcactaac gataacgacc                                                    20

<210> SEQ ID NO 936
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 936
cgcagtcaac ttacacgtta                                                    20

<210> SEQ ID NO 937
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 937
cagcgtgatt catttacggt                                                    20

<210> SEQ ID NO 938
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 938
cactcgtaac tataccgaag                                                    20

<210> SEQ ID NO 939
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 939
tcaccgtact ttaacgagcg                                                    20

<210> SEQ ID NO 940
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 940
agtacagtgt ttgaacccgg                                                    20

<210> SEQ ID NO 941
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 941
ctcatagttg gtaatacggg 20

<210> SEQ ID NO 942
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 942
ccctctctag gtacgtggtt 20

<210> SEQ ID NO 943
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 943
ccttcgattg gacgggattt 20

<210> SEQ ID NO 944
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 944
ctgcgtgaga tcggcctatt 20

<210> SEQ ID NO 945
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 945
catgacgatt gtccagtagt 20

<210> SEQ ID NO 946
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 946
taaacgcatc gtgtaccagg 20

<210> SEQ ID NO 947
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 947
cagaccgact tagacgagtg 20

<210> SEQ ID NO 948
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 948
atagccgacg taccagagag                                          20

<210> SEQ ID NO 949
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 949
tcaccgttgt aactgctgcg                                          20

<210> SEQ ID NO 950
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 950
atgcaccgtc cctaattggg                                          20

<210> SEQ ID NO 951
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 951
ttaccgcgct tacagtcgtg                                          20

<210> SEQ ID NO 952
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 952
tacacgggtg ctaatgtccg                                          20

<210> SEQ ID NO 953
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 953
catacacgta aagtgcgcga                                          20

<210> SEQ ID NO 954
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 954
cactatcgta aagtctgcga                                               20

<210> SEQ ID NO 955
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 955
acatcttgta aagcgcgtga                                               20

<210> SEQ ID NO 956
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 956
taagctagta taaccgctgc                                               20

<210> SEQ ID NO 957
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 957
atagcgagct tgaacaccgc                                               20

<210> SEQ ID NO 958
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 958
atatcgagtg cgacatcccg                                               20

<210> SEQ ID NO 959
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 959
tatcagggcc tagtgactgt                                               20

<210> SEQ ID NO 960
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 960
atgcggagtc cacgctattg                                               20

<210> SEQ ID NO 961
<211> LENGTH: 20
```

<212> TYPE: DNA
<213> ORGANISM: Artificial Sequence
<220> FEATURE:
<223> OTHER INFORMATION: synthetic oligonucleotide

<400> SEQUENCE: 961
tgcacgagtc tccagtgttg                                          20

<210> SEQ ID NO 962
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 962
accgagcgta tcgcactttg                                          20

<210> SEQ ID NO 963
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 963
tagggacctc tcgccatttg                                          20

<210> SEQ ID NO 964
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 964
ttggtacgtc ctccatgcgt                                          20

<210> SEQ ID NO 965
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 965
gcatacgctg tgccatcagt                                          20

<210> SEQ ID NO 966
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 966
gatagctctg tgcatcaggt                                          20

<210> SEQ ID NO 967
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 967

| | |
|---|---|
| cggtactcag tcatagtgat | 20 |

<210> SEQ ID NO 968
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 968

| | |
|---|---|
| tgtgacccga catagtctgc | 20 |

<210> SEQ ID NO 969
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 969

| | |
|---|---|
| tagatcgcag cactatgccg | 20 |

<210> SEQ ID NO 970
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 970

| | |
|---|---|
| gagatcgcaa catagctcga | 20 |

<210> SEQ ID NO 971
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 971

| | |
|---|---|
| gacatcgcgc aattcatcta | 20 |

<210> SEQ ID NO 972
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 972

| | |
|---|---|
| gatgcgtcac catgctacag | 20 |

<210> SEQ ID NO 973
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 973

| | |
|---|---|
| gatgtctcac cagtgctcag | 20 |

<210> SEQ ID NO 974
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 974
ggcatctata ccaggctcag                                                  20

<210> SEQ ID NO 975
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 975
catgtatcag aacgcatcac                                                  20

<210> SEQ ID NO 976
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 976
gatctaacga cactctgagc                                                  20

<210> SEQ ID NO 977
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 977
catataacgc acgatctagc                                                  20

<210> SEQ ID NO 978
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 978
tagatgacag cagcgaccag                                                  20

<210> SEQ ID NO 979
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 979
attgacgcac cgacagatgc                                                  20

<210> SEQ ID NO 980
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 980
tattagccac catcgtatgc                                                  20
```

<210> SEQ ID NO 981
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 981
tagatgcgac catagcgtgc         20

<210> SEQ ID NO 982
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 982
tatgacggac gacatgcctc         20

<210> SEQ ID NO 983
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 983
tgactagcga catgctgctc         20

<210> SEQ ID NO 984
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 984
gagagagctg catagacatc         20

<210> SEQ ID NO 985
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 985
tagagtacgc acagcgcatc         20

<210> SEQ ID NO 986
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 986
atgatggcac gctcgcagat         20

<210> SEQ ID NO 987
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 987
tatatggcag cagatcgccg                                              20

<210> SEQ ID NO 988
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 988
tatggagcag gatcactatg                                              20

<210> SEQ ID NO 989
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 989
tcgagagcgt gacactcatg                                              20

<210> SEQ ID NO 990
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 990
ataggactcg acacatcagc                                              20

<210> SEQ ID NO 991
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 991
gagagatgct caacagccac                                              20

<210> SEQ ID NO 992
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 992
tagagaggat cacacccagc                                              20

<210> SEQ ID NO 993
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 993
ttcagaggac aacacgcgca                                              20

<210> SEQ ID NO 994
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 994
gtgcagactc aacaccatga                                            20

<210> SEQ ID NO 995
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 995
tccgagacgc aacgacatga                                            20

<210> SEQ ID NO 996
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 996
ttatcgactg ccagcgactg                                            20

<210> SEQ ID NO 997
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 997
ctatcgagga tcacggactg                                            20

<210> SEQ ID NO 998
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 998
atcaggtcct cactggctgt                                            20

<210> SEQ ID NO 999
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 999
atgtacgcct gcacttggct                                            20

<210> SEQ ID NO 1000
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1000
```
agtcgcgctg tccatttgct                    20

<210> SEQ ID NO 1001
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1001
tgagcgcctt cactctgtgt                    20

<210> SEQ ID NO 1002
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1002
ggatgctctc tcacgagtct                    20

<210> SEQ ID NO 1003
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1003
tgcacaccgc tcagtagttg                    20

<210> SEQ ID NO 1004
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1004
gatcagacga cactagagtc                    20

<210> SEQ ID NO 1005
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1005
agatggccgc tcctcagatt                    20

<210> SEQ ID NO 1006
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1006
atgcggacga tcctcgatat                    20

<210> SEQ ID NO 1007
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 1007
gagtgatctg cacctcgtat                                              20

<210> SEQ ID NO 1008
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1008
agagtagcga ccactatctc                                              20

<210> SEQ ID NO 1009
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1009
agatatacga cagacctcgc                                              20

<210> SEQ ID NO 1010
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1010
gcgatctcga aagccataca                                              20

<210> SEQ ID NO 1011
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1011
ggctacacga aatcgctaca                                              20

<210> SEQ ID NO 1012
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1012
atcgcaacta acgcgctata                                              20

<210> SEQ ID NO 1013
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1013
tatggaactc accgcgtagc                                              20
```

```
<210> SEQ ID NO 1014
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1014
aatcggactg gcagccgtat                                                     20

<210> SEQ ID NO 1015
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1015
ttagtggcct gcaccgctat                                                     20

<210> SEQ ID NO 1016
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1016
tagtatgcgt cactcgctct                                                     20

<210> SEQ ID NO 1017
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1017
ggagatgcct cactgcctat                                                     20

<210> SEQ ID NO 1018
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1018
gcagagtccc tatcagctat                                                     20

<210> SEQ ID NO 1019
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1019
gcgcagactc tccagatatg                                                     20

<210> SEQ ID NO 1020
<211> LENGTH: 20
<212> TYPE: DNA
<213> ORGANISM: Artificial Sequence
<220> FEATURE:
```

-continued

```
<223> OTHER INFORMATION: synthetic oligonucleotide

<400> SEQUENCE: 1020
cgcctgacta taatgctatc                                               20

<210> SEQ ID NO 1021
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1021
gcacatggat taacagtagc                                               20

<210> SEQ ID NO 1022
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1022
gccagatgca gtaatacgag                                               20

<210> SEQ ID NO 1023
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1023
gcacgacagt tcataacagc                                               20

<210> SEQ ID NO 1024
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1024
gccgatgaga taatagtagc                                               20

<210> SEQ ID NO 1025
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1025
cccgatgctg aattagtatc                                               20

<210> SEQ ID NO 1026
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1026
ccgcatacgc aataagtgga                                               20
```

```
<210> SEQ ID NO 1027
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1027
actgcatcgt aatgagtgag                                                 20

<210> SEQ ID NO 1028
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1028
cagagattgt aagcagctag                                                 20

<210> SEQ ID NO 1029
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1029
tcagaggcgt aagcactcag                                                 20

<210> SEQ ID NO 1030
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1030
tagactgcgc taactgccag                                                 20

<210> SEQ ID NO 1031
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1031
tttgaggcag ctacgcccat                                                 20

<210> SEQ ID NO 1032
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1032
atttggtcct cacgcgactg                                                 20

<210> SEQ ID NO 1033
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 1033
tattgcgatg cacccggact                                               20

<210> SEQ ID NO 1034
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1034
agtgcgtacc tatcgcgctt                                               20

<210> SEQ ID NO 1035
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1035
ctacgtcggc tcatagtcgt                                               20

<210> SEQ ID NO 1036
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1036
cttcagtggc tacgatgagt                                               20

<210> SEQ ID NO 1037
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1037
acccgtcgtg tcactatgtt                                               20

<210> SEQ ID NO 1038
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1038
ggcgctcgta tgactgattt                                               20

<210> SEQ ID NO 1039
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1039
ggagccggta tatttgcatt                                               20

<210> SEQ ID NO 1040
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1040
tgagccgctt gcactagagt                                         20

<210> SEQ ID NO 1041
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1041
gagacgcctc gattactatg                                         20

<210> SEQ ID NO 1042
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1042
cggaggctca gatgtactat                                         20

<210> SEQ ID NO 1043
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1043
gcgacgtata gattcgtatg                                         20

<210> SEQ ID NO 1044
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1044
ggcacgtctc gattgatgtt                                         20

<210> SEQ ID NO 1045
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1045
ccgcataccg aattgctata                                         20

<210> SEQ ID NO 1046
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1046
```
cagctctcgc aatagtctta 20

<210> SEQ ID NO 1047
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1047
tagctggcgc aacctgctta 20

<210> SEQ ID NO 1048
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1048
gctaacgcgc aacacgtata 20

<210> SEQ ID NO 1049
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1049
agcctgacgc tatctcgatt 20

<210> SEQ ID NO 1050
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1050
aacgctccgc aagtcgatta 20

<210> SEQ ID NO 1051
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1051
acgaggaggc aactctatta 20

<210> SEQ ID NO 1052
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1052
acaggcaggc aatcgttgta 20

<210> SEQ ID NO 1053
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1053
agacagaggc aacttgtgta                                              20

<210> SEQ ID NO 1054
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1054
gagctgagtg aatctttctc                                              20

<210> SEQ ID NO 1055
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1055
gcactctgct gaagttcgtc                                              20

<210> SEQ ID NO 1056
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1056
tcattcggtg aagttgcgtc                                              20

<210> SEQ ID NO 1057
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1057
tatgccggta cacttgcgtg                                              20

<210> SEQ ID NO 1058
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1058
tatgtcagtc cacgccgatg                                              20

<210> SEQ ID NO 1059
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1059
tattgcagtc caccgcgatg                                              20
```

<210> SEQ ID NO 1060
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1060
ttacatagta cactgcgcgg                               20

<210> SEQ ID NO 1061
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1061
tgactcagta gcatcgttgg                               20

<210> SEQ ID NO 1062
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1062
atatctcaca tgcccggaag                               20

<210> SEQ ID NO 1063
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1063
tatctcagca cacgggacag                               20

<210> SEQ ID NO 1064
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1064
atatcttgct cacggcgcgt                               20

<210> SEQ ID NO 1065
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1065
atacgatgct cacgttggcg                               20

<210> SEQ ID NO 1066
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1066
tatacctgac cagtgcggag                                               20

<210> SEQ ID NO 1067
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1067
tattcgtgac cactcgcagg                                               20

<210> SEQ ID NO 1068
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1068
gagaccagac caacctgtga                                               20

<210> SEQ ID NO 1069
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1069
gatacgcgaa cataccgtga                                               20

<210> SEQ ID NO 1070
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1070
gagacggtta cattccgatg                                               20

<210> SEQ ID NO 1071
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1071
tattggctta cacgccgctg                                               20

<210> SEQ ID NO 1072
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1072
ctgacgatta gactgagttg                                               20

<210> SEQ ID NO 1073

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1073
atactcgcgt cagggatgct                                               20

<210> SEQ ID NO 1074
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1074
tacgcagcga cagtagactc                                               20

<210> SEQ ID NO 1075
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1075
tctaagccga caggagtctc                                               20

<210> SEQ ID NO 1076
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1076
cacagaccga cagtaggatc                                               20

<210> SEQ ID NO 1077
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1077
cgacagacta cattaagtgc                                               20

<210> SEQ ID NO 1078
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1078
ccgcatactc gatattagtc                                               20

<210> SEQ ID NO 1079
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1079
```
cgcctgacag tagtataatc                                          20

<210> SEQ ID NO 1080
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1080
caggcgtcag tagtattcat                                          20

<210> SEQ ID NO 1081
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1081
gccatgacag tcgtatcaag                                          20

<210> SEQ ID NO 1082
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1082
gagcatacac cagtcttagc                                          20

<210> SEQ ID NO 1083
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1083
agcagagcac cagtctaatc                                          20

<210> SEQ ID NO 1084
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1084
gagcagacta cagttatgtc                                          20

<210> SEQ ID NO 1085
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1085
gagcaggcta cagactcttc                                          20

<210> SEQ ID NO 1086
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 1086
acgagcgatt aagtgtcacg                                               20

<210> SEQ ID NO 1087
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1087
tcagacggtt aaggcatccg                                               20

<210> SEQ ID NO 1088
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1088
cgcacacgat taaggtccag                                               20

<210> SEQ ID NO 1089
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1089
tacaggcgat taagcgtccg                                               20

<210> SEQ ID NO 1090
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1090
catgtgtagt aatcgtagcg                                               20

<210> SEQ ID NO 1091
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1091
acaggtgagt aatctgcccg                                               20

<210> SEQ ID NO 1092
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1092
aaggcagact actcgatccg                                               20
```

```
<210> SEQ ID NO 1093
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1093
aagagcatcc tacaggtacg                                               20

<210> SEQ ID NO 1094
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1094
tatagtgtcg aaccgtccgc                                               20

<210> SEQ ID NO 1095
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1095
atagatgact accgcgtccg                                               20

<210> SEQ ID NO 1096
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1096
atagctcatt aaccggcacg                                               20

<210> SEQ ID NO 1097
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1097
catagtgtac cagagcgacg                                               20

<210> SEQ ID NO 1098
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1098
ttgctagtca cacgacgacg                                               20

<210> SEQ ID NO 1099
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 1099
agagcgatta cacgacccag                                                  20

<210> SEQ ID NO 1100
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1100
ataggcgtgt aacgtcctcg                                                  20

<210> SEQ ID NO 1101
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1101
tgcacgatgt taagtccgcg                                                  20

<210> SEQ ID NO 1102
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1102
taagagaggt tacgacaccg                                                  20

<210> SEQ ID NO 1103
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1103
aatgataggt aatcggaccg                                                  20

<210> SEQ ID NO 1104
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1104
tacagaaagt aagcgtcccg                                                  20

<210> SEQ ID NO 1105
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1105
catatagatt aagggcgacg                                                  20

```
<210> SEQ ID NO 1106
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1106
ccatcttagt aacgtggacg                                                    20

<210> SEQ ID NO 1107
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1107
agacttcact aacgggccag                                                    20

<210> SEQ ID NO 1108
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1108
tatacttgcg taacgggccg                                                    20

<210> SEQ ID NO 1109
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1109
aatactagcg aacgggaccc                                                    20

<210> SEQ ID NO 1110
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1110
attatacggg acggacaccg                                                    20

<210> SEQ ID NO 1111
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1111
agtcacaggg tcctaatccg                                                    20

<210> SEQ ID NO 1112
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 1112
gtaccggatc tagctctgct                                            20

<210> SEQ ID NO 1113
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1113
atatccgact cagctctgtg                                            20

<210> SEQ ID NO 1114
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1114
cctctgtact aatgatgcag                                            20

<210> SEQ ID NO 1115
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1115
ccagcgtact gcatattcag                                            20

<210> SEQ ID NO 1116
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1116
gccagcgaca caatgtagca                                            20

<210> SEQ ID NO 1117
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1117
acagtgtacc aatgtgctga                                            20

<210> SEQ ID NO 1118
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1118
ctcatgtagt gacagtgctg                                            20

<210> SEQ ID NO 1119
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1119
aatctctatg cagtgaggtg                                              20

<210> SEQ ID NO 1120
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1120
tcacctgatg cagtggagat                                              20

<210> SEQ ID NO 1121
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1121
attctcgata gagcgtgctg                                              20

<210> SEQ ID NO 1122
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1122
cgctacgata tagagatgtg                                              20

<210> SEQ ID NO 1123
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1123
cttagcgata gagtgctgat                                              20

<210> SEQ ID NO 1124
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1124
gaagcataag catgtgtgac                                              20

<210> SEQ ID NO 1125
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1125
```

```
atacaccata cactgtgagc                                           20

<210> SEQ ID NO 1126
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1126
taacgcgaca gacgatatgc                                           20

<210> SEQ ID NO 1127
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1127
ataccggaca gcagctacag                                           20

<210> SEQ ID NO 1128
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1128
gaactgaatg cactcgaagc                                           20

<210> SEQ ID NO 1129
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1129
tgacccgatg cactcgtgat                                           20

<210> SEQ ID NO 1130
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1130
tttgatcgag tggcacccgt                                           20

<210> SEQ ID NO 1131
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1131
atcttgcgag gaccgtcgat                                           20

<210> SEQ ID NO 1132
<211> LENGTH: 20
<212> TYPE: DNA
<213> ORGANISM: Artificial Sequence
```

```
<220> FEATURE:
<223> OTHER INFORMATION: synthetic oligonucleotide

<400> SEQUENCE: 1132
attacgtgtc gcatccggct                                               20

<210> SEQ ID NO 1133
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1133
ctcacgagta gtcatgggat                                               20

<210> SEQ ID NO 1134
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1134
accacgattg gaagggcatc                                               20

<210> SEQ ID NO 1135
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1135
atccgcgtgt ccatagtggt                                               20

<210> SEQ ID NO 1136
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1136
acaccgtcac catagattag                                               20

<210> SEQ ID NO 1137
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1137
cacctagctc catagtgagg                                               20

<210> SEQ ID NO 1138
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1138
cacacttcta aagcagtcga                                               20
```

```
<210> SEQ ID NO 1139
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1139
catcactggt aatagaggag                                                 20

<210> SEQ ID NO 1140
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1140
gctcctacat aataaggcac                                                 20

<210> SEQ ID NO 1141
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1141
tgccgagctg aacaacgaca                                                 20

<210> SEQ ID NO 1142
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1142
ctcccgacta aagagaggca                                                 20

<210> SEQ ID NO 1143
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1143
ccgtcggcat aatagagaac                                                 20

<210> SEQ ID NO 1144
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1144
gcatcgacag aatcctgaac                                                 20

<210> SEQ ID NO 1145
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 1145
ctgcggacag aacgcgaata                                          20

<210> SEQ ID NO 1146
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1146
gcaggatcaa cacgagtcta                                          20

<210> SEQ ID NO 1147
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1147
tcgaggacag aatcggacac                                          20

<210> SEQ ID NO 1148
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1148
cgacgaaccg aatgcgatac                                          20

<210> SEQ ID NO 1149
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1149
gactacaccg aatctgatac                                          20

<210> SEQ ID NO 1150
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1150
cgactaaccg tacatgacag                                          20

<210> SEQ ID NO 1151
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1151
aaactacgtg gctaatggcg                                          20

<210> SEQ ID NO 1152

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1152
actaccagtc gatatgaggg                                          20

<210> SEQ ID NO 1153
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1153
ttccctagtc cagacggatg                                          20

<210> SEQ ID NO 1154
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1154
ttagttcgca ccagaccgag                                          20

<210> SEQ ID NO 1155
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1155
ttagaccgat cactacgcgg                                          20

<210> SEQ ID NO 1156
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1156
tttgaccgcc tacatcgagg                                          20

<210> SEQ ID NO 1157
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1157
tttacgggac ccatctgagg                                          20

<210> SEQ ID NO 1158
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1158
```
ataggtagca catctcgcgc                                                 20

<210> SEQ ID NO 1159
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1159
tatgaggttc cacaccgtgc                                                 20

<210> SEQ ID NO 1160
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1160
tatgacttga cacacggcgc                                                 20

<210> SEQ ID NO 1161
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1161
tattgcgtga cacctgctcg                                                 20

<210> SEQ ID NO 1162
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1162
attgacctga gacgcagtcg                                                 20

<210> SEQ ID NO 1163
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1163
attcgactaa cagcgatgcc                                                 20

<210> SEQ ID NO 1164
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1164
tagcgagtga aagccacgca                                                 20

<210> SEQ ID NO 1165
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 1165
acagacgtga aactcctgca                                              20

<210> SEQ ID NO 1166
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1166
cctatactga aactgacgca                                              20

<210> SEQ ID NO 1167
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1167
gcaccactag aatctgagac                                              20

<210> SEQ ID NO 1168
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1168
gcacacatag aatctgtcac                                              20

<210> SEQ ID NO 1169
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1169
cgacatatcg aacatgcgac                                              20

<210> SEQ ID NO 1170
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1170
gacagcatgt aacagcagcc                                              20

<210> SEQ ID NO 1171
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1171
cgagtaatct aagcgatcag                                              20
```

```
<210> SEQ ID NO 1172
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1172
cagtaagtat aacgagctgc                                                    20

<210> SEQ ID NO 1173
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1173
aggatacttc acgcgctgtc                                                    20

<210> SEQ ID NO 1174
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1174
taagagatag caccagcgcc                                                    20

<210> SEQ ID NO 1175
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1175
aataggctct gcacacacgg                                                    20

<210> SEQ ID NO 1176
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1176
acatacgttg cagcagacgg                                                    20

<210> SEQ ID NO 1177
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1177
tactagctga cacagggtgc                                                    20

<210> SEQ ID NO 1178
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 1178
aatgtgctac aagagcgtga 20

<210> SEQ ID NO 1179
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1179
tagcatgttc gacacgacgg 20

<210> SEQ ID NO 1180
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1180
cgagctgtat aagttaccag 20

<210> SEQ ID NO 1181
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1181
acgaccgatt tatacgcatg 20

<210> SEQ ID NO 1182
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1182
aaccagcact tgtctaacgg 20

<210> SEQ ID NO 1183
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1183
gacagatcgt taatcagtcg 20

<210> SEQ ID NO 1184
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1184
gcacgtatgt taatctgtgg 20

```
<210> SEQ ID NO 1185
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1185
cgacgattgt tacacagttg                                              20

<210> SEQ ID NO 1186
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1186
cgccgtctga ttagagaatt                                              20

<210> SEQ ID NO 1187
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1187
cgccgattgt ttaatgcact                                              20

<210> SEQ ID NO 1188
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1188
ctctaggctc gatagtgagt                                              20

<210> SEQ ID NO 1189
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1189
cccgtgcatc aatagtagta                                              20

<210> SEQ ID NO 1190
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1190
ccgcagtatc aataagcgta                                              20

<210> SEQ ID NO 1191
<211> LENGTH: 20
<212> TYPE: DNA
<213> ORGANISM: Artificial Sequence
<220> FEATURE:
<223> OTHER INFORMATION: synthetic oligonucleotide
```

-continued

<400> SEQUENCE: 1191
cccacgtatc aatagaggta                                          20

<210> SEQ ID NO 1192
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1192
gatgcgtatc cagcgttgct                                          20

<210> SEQ ID NO 1193
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1193
gatcgtcatc cacgcttgat                                          20

<210> SEQ ID NO 1194
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1194
aatcgtcacc aacgtgcata                                          20

<210> SEQ ID NO 1195
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1195
catcgtctcc aatagctgta                                          20

<210> SEQ ID NO 1196
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1196
catcgagtcc aactgatcta                                          20

<210> SEQ ID NO 1197
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1197
gctcaactcc aacgatatga                                          20

<210> SEQ ID NO 1198
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 1198
gctcgtctca aatcacagaa                                              20

<210> SEQ ID NO 1199
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1199
gctcctcgac aataatagca                                              20

<210> SEQ ID NO 1200
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1200
ccgcgcagtc aatatagata                                              20

<210> SEQ ID NO 1201
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1201
gctccgaacc aataatgtca                                              20

<210> SEQ ID NO 1202
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1202
gcgcgacacc aagatagtca                                              20

<210> SEQ ID NO 1203
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1203
gcgacataca cacagcggta                                              20

<210> SEQ ID NO 1204
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1204
```

|  |  |
|---|---|
| ccgtagcata aagagcggca | 20 |

<210> SEQ ID NO 1205
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1205

|  |  |
|---|---|
| atgatgtaac tagagcgcag | 20 |

<210> SEQ ID NO 1206
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1206

|  |  |
|---|---|
| gcctactaac taatgagagc | 20 |

<210> SEQ ID NO 1207
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1207

|  |  |
|---|---|
| cgtctacata cataacgagc | 20 |

<210> SEQ ID NO 1208
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1208

|  |  |
|---|---|
| gtcgcacaca ttgatacaac | 20 |

<210> SEQ ID NO 1209
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1209

|  |  |
|---|---|
| ctcacacaga gatattcgac | 20 |

<210> SEQ ID NO 1210
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1210

|  |  |
|---|---|
| gctccacaga tgaagatacc | 20 |

<210> SEQ ID NO 1211
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1211
agctcacagt acagagactc                                              20

<210> SEQ ID NO 1212
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1212
gccactaatc aactggacta                                              20

<210> SEQ ID NO 1213
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1213
cgattcgata aatgacgcga                                              20

<210> SEQ ID NO 1214
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1214
cgttagtaca aagcacctca                                              20

<210> SEQ ID NO 1215
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1215
ccgtagcaca gatataactc                                              20

<210> SEQ ID NO 1216
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1216
gagctagaca gagattacgc                                              20

<210> SEQ ID NO 1217
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1217
gcacgagata cagtacacgc                                              20
```

<210> SEQ ID NO 1218
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1218
cggagagaca gattacacgc                                                     20

<210> SEQ ID NO 1219
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1219
gcgagagacg taatcagatc                                                     20

<210> SEQ ID NO 1220
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1220
cctagagacg tagatatgcg                                                     20

<210> SEQ ID NO 1221
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1221
cgagataagg tgcgatcact                                                     20

<210> SEQ ID NO 1222
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1222
ccatgtaact caagtcagac                                                     20

<210> SEQ ID NO 1223
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1223
ccatgtagat caagtagcac                                                     20

<210> SEQ ID NO 1224
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1224
cggcagtatg aatagtaagc                                           20

<210> SEQ ID NO 1225
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1225
ccatgatatg aacgtagagc                                           20

<210> SEQ ID NO 1226
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1226
cccagatata gagcgatagg                                           20

<210> SEQ ID NO 1227
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1227
ctagcaggta gcacgatacg                                           20

<210> SEQ ID NO 1228
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1228
ggctaacgta caggacactc                                           20

<210> SEQ ID NO 1229
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1229
gccactagct tcgtacatat                                           20

<210> SEQ ID NO 1230
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1230
ccgcagcgtc aataactata                                           20

<210> SEQ ID NO 1231

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1231
gcccggcgta gaaagcataa                                              20

<210> SEQ ID NO 1232
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1232
gcccgctgta aacatagaca                                              20

<210> SEQ ID NO 1233
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1233
cgccggtgta aagataagca                                              20

<210> SEQ ID NO 1234
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1234
ccagcgtgga aatcattaca                                              20

<210> SEQ ID NO 1235
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1235
ccgcgtcgta aatgattaga                                              20

<210> SEQ ID NO 1236
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1236
gcccgacgac aatagtatca                                              20

<210> SEQ ID NO 1237
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1237
```
ccgcgacctc aataagtata                                                    20

<210> SEQ ID NO 1238
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1238
gcccgacatc taaagtcaga                                                    20

<210> SEQ ID NO 1239
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1239
ccgctaggtt aatagtcatg                                                    20

<210> SEQ ID NO 1240
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1240
tcacagacgt tggcaagacc                                                    20

<210> SEQ ID NO 1241
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1241
tcggacccag gttgataacg                                                    20

<210> SEQ ID NO 1242
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1242
actcactcag gtggataagg                                                    20

<210> SEQ ID NO 1243
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1243
agctacgcgc tttgaacacg                                                    20

<210> SEQ ID NO 1244
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 1244
tctacgacgt gtctaaggcg                                              20

<210> SEQ ID NO 1245
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1245
tctacagtgg tataagagcg                                              20

<210> SEQ ID NO 1246
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1246
cctcaggtga ttaactggcg                                              20

<210> SEQ ID NO 1247
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1247
gtcacagtgg taacatcctc                                              20

<210> SEQ ID NO 1248
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1248
gcccgtatgg taacattatc                                              20

<210> SEQ ID NO 1249
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1249
cgccgtgtga aacatactaa                                              20

<210> SEQ ID NO 1250
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1250
ccgatgtgag aatctagtac                                              20
```

```
<210> SEQ ID NO 1251
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1251
ccgtgcgtag aatgaagaac                                            20

<210> SEQ ID NO 1252
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1252
ccaggtgtag aatagtgtac                                            20

<210> SEQ ID NO 1253
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1253
ccgcgattca aacgattcaa                                            20

<210> SEQ ID NO 1254
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1254
gctgcgatag tatagcttct                                            20

<210> SEQ ID NO 1255
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1255
cgcagagtag ttaattgcag                                            20

<210> SEQ ID NO 1256
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1256
tacacgattg ttgaagtgcg                                            20

<210> SEQ ID NO 1257
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 1257
tagcacgtcg tacatagccg					20

<210> SEQ ID NO 1258
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1258
tacagcgtcg aattagccgc					20

<210> SEQ ID NO 1259
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1259
cacgcgattg aatttactgc					20

<210> SEQ ID NO 1260
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1260
catagcgtgg aatctacctc					20

<210> SEQ ID NO 1261
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1261
ccagacgtgg aactattcgc					20

<210> SEQ ID NO 1262
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1262
gactcagtgt aactcagtag					20

<210> SEQ ID NO 1263
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1263
cgtgtattaa cagtgatcgc					20

```
<210> SEQ ID NO 1264
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1264
tatcgtatga cagtggatcg                                                     20

<210> SEQ ID NO 1265
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1265
acagttgcag catcgtgtcg                                                     20

<210> SEQ ID NO 1266
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1266
accgtagcca gatgagatcg                                                     20

<210> SEQ ID NO 1267
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1267
gcggatacta gagctatatg                                                     20

<210> SEQ ID NO 1268
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1268
cgcgagcata tcaggttctg                                                     20

<210> SEQ ID NO 1269
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1269
agcgagcgat agatgttcat                                                     20

<210> SEQ ID NO 1270
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 1270
acgcttagta cagtctcatg                                           20

<210> SEQ ID NO 1271
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1271
cacggctatt ccagtcatat                                           20

<210> SEQ ID NO 1272
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1272
caggtgtata gagttctgct                                           20

<210> SEQ ID NO 1273
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1273
agagcgtatg gcattgtact                                           20

<210> SEQ ID NO 1274
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1274
aactgctatg cacgtctact                                           20

<210> SEQ ID NO 1275
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1275
atacgttaga caggtcagcg                                           20

<210> SEQ ID NO 1276
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1276
tacacttatg aagcgcgggc                                           20

<210> SEQ ID NO 1277
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1277
ataccttatg cacgggtgtg                                          20

<210> SEQ ID NO 1278
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1278
atatactgtg gcacgggcct                                          20

<210> SEQ ID NO 1279
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1279
aattctcggt catcgcgggt                                          20

<210> SEQ ID NO 1280
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1280
atattgtctg accgccgcgt                                          20

<210> SEQ ID NO 1281
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1281
tcacgtctga gattgccggt                                          20

<210> SEQ ID NO 1282
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1282
atactgtccc aacgcgggta                                          20

<210> SEQ ID NO 1283
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1283
```
atagcgtcag aagtcccgac 20

<210> SEQ ID NO 1284
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1284
atagtatcgg aactcgccgc 20

<210> SEQ ID NO 1285
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1285
aattgatggg aagtcctcgc 20

<210> SEQ ID NO 1286
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1286
tattatcgtg gacagcccgg 20

<210> SEQ ID NO 1287
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1287
tattcacgta gacggatagg 20

<210> SEQ ID NO 1288
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1288
atcgaccagt tgcagacagg 20

<210> SEQ ID NO 1289
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1289
acgattgagt tacagcgatg 20

<210> SEQ ID NO 1290
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1290
gcatacgagt taagcatcag                                                    20

<210> SEQ ID NO 1291
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1291
acgacgacgt taatcacatc                                                    20

<210> SEQ ID NO 1292
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1292
aagacgacgt aagcccatgc                                                    20

<210> SEQ ID NO 1293
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1293
aaagtcgcag taatccgcag                                                    20

<210> SEQ ID NO 1294
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1294
cagtcagcgt catgttcgat                                                    20

<210> SEQ ID NO 1295
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1295
cagctaccgt aatctcatag                                                    20

<210> SEQ ID NO 1296
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1296
aagataccgt aacatgcggc                                                    20
```

```
<210> SEQ ID NO 1297
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1297
aacgtatcgg aagcataggc                                               20

<210> SEQ ID NO 1298
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1298
ccgatatgga aagctaggca                                               20

<210> SEQ ID NO 1299
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1299
aatactgcga aagcgcggca                                               20

<210> SEQ ID NO 1300
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1300
actactgcat aagggagtgc                                               20

<210> SEQ ID NO 1301
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1301
cactacgcag aaggtgacac                                               20

<210> SEQ ID NO 1302
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1302
ctacatgcag tacagtggag                                               20

<210> SEQ ID NO 1303
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 1303
accgactcgt aagcgatgag                                          20

<210> SEQ ID NO 1304
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1304
aacgacctgt gacacgatat                                          20

<210> SEQ ID NO 1305
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1305
atagtccggg aactgtatgc                                          20

<210> SEQ ID NO 1306
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1306
acatttaggg aacgcagagc                                          20

<210> SEQ ID NO 1307
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1307
gcattaagtg taacgcagag                                          20

<210> SEQ ID NO 1308
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1308
actatgcgag gacacgctag                                          20

<210> SEQ ID NO 1309
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1309
aacgagtatg cgagacccgt                                          20

<210> SEQ ID NO 1310

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1310
actatctatc gagcgggagt                                                 20

<210> SEQ ID NO 1311
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1311
catcgctatg gatcggtgtt                                                 20

<210> SEQ ID NO 1312
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1312
tcctagtatg gacgattggt                                                 20

<210> SEQ ID NO 1313
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1313
tcagggtagg aacgtcactc                                                 20

<210> SEQ ID NO 1314
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1314
ggcgtatccc tagatgtcct                                                 20

<210> SEQ ID NO 1315
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1315
cgagttatac gactgttgct                                                 20

<210> SEQ ID NO 1316
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1316
```

```
ccggttatcc aagtgtacta                                              20

<210> SEQ ID NO 1317
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1317
acgggtatcc agggtcacat                                              20

<210> SEQ ID NO 1318
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1318
cagtcgatac gagggtccat                                              20

<210> SEQ ID NO 1319
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1319
tatgggatac gacgcccgat                                              20

<210> SEQ ID NO 1320
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1320
gaaggcatcg taactccgag                                              20

<210> SEQ ID NO 1321
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1321
aagccggtcg taacttgtag                                              20

<210> SEQ ID NO 1322
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1322
ccgtgtctat aagtgttcag                                              20

<210> SEQ ID NO 1323
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 1323
aacgagttat taagccgccg                                              20

<210> SEQ ID NO 1324
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1324
caacggatag ttagtcaggt                                              20

<210> SEQ ID NO 1325
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1325
aacttatgtg gctagacggt                                              20

<210> SEQ ID NO 1326
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1326
accttgtggg taatgcgtat                                              20

<210> SEQ ID NO 1327
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1327
cgctgatagt tagctggatt                                              20

<210> SEQ ID NO 1328
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1328
accgatgcgt catttcgtct                                              20

<210> SEQ ID NO 1329
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1329
ctcgtgacgt ttgagcagtt                                              20
```

<210> SEQ ID NO 1330
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1330
cgcatgtcgt gaattagttc                                              20

<210> SEQ ID NO 1331
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1331
tgccattcgg aactaggctc                                              20

<210> SEQ ID NO 1332
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1332
aatgtttcgc aactcgggcc                                              20

<210> SEQ ID NO 1333
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1333
ttgtgtactc gacccgctgt                                              20

<210> SEQ ID NO 1334
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1334
taggtatcga cacccaggtc                                              20

<210> SEQ ID NO 1335
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1335
ccatatagag aaccgggcac                                              20

<210> SEQ ID NO 1336
<211> LENGTH: 20
<212> TYPE: DNA
<213> ORGANISM: Artificial Sequence
<220> FEATURE:

```
<223> OTHER INFORMATION: synthetic oligonucleotide

<400> SEQUENCE: 1336
atatgtagtg aaccgcccgc                                          20

<210> SEQ ID NO 1337
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1337
tagataggta caccgaccgc                                          20

<210> SEQ ID NO 1338
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1338
gattagcgta cataggcccg                                          20

<210> SEQ ID NO 1339
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1339
agtatgccta catccggtcg                                          20

<210> SEQ ID NO 1340
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1340
gatatgccta aagcggtaga                                          20

<210> SEQ ID NO 1341
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1341
tgactagcat tacagggacg                                          20

<210> SEQ ID NO 1342
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1342
catcatgcta aagtggacga                                          20
```

<210> SEQ ID NO 1343
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1343
agcatgtctc taactggacg                                               20

<210> SEQ ID NO 1344
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1344
gaactggctt gaatgttacg                                               20

<210> SEQ ID NO 1345
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1345
gcatcgactt aatggtcacg                                               20

<210> SEQ ID NO 1346
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1346
ggtcgaaccc aatactacga                                               20

<210> SEQ ID NO 1347
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1347
gctgatacga aacctgacca                                               20

<210> SEQ ID NO 1348
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1348
ccagtgacgc aactttacta                                               20

<210> SEQ ID NO 1349
<211> LENGTH: 20
<212> TYPE: DNA
<213> ORGANISM: Artificial Sequence
<220> FEATURE:
<223> OTHER INFORMATION: synthetic oligonucleotide -continued

<400> SEQUENCE: 1349
tgtaggacgc tatcccgact                                              20

<210> SEQ ID NO 1350
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1350
attagtgccg accacgactg                                              20

<210> SEQ ID NO 1351
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1351
agttcgaccc acgcattaag                                              20

<210> SEQ ID NO 1352
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1352
atatcgacca tccgcgtaag                                              20

<210> SEQ ID NO 1353
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1353
atacatgcga cagcggtaag                                              20

<210> SEQ ID NO 1354
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1354
aaacactcag caccgttagg                                              20

<210> SEQ ID NO 1355
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1355
tatcgcgtca cagttactcg                                              20

<210> SEQ ID NO 1356
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 1356
atatcggcac caggtacgag                                              20

<210> SEQ ID NO 1357
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1357
cgtccgacag acaggtaaac                                              20

<210> SEQ ID NO 1358
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1358
gcactaacac gaagtttcac                                              20

<210> SEQ ID NO 1359
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1359
atctacgcag gacgttgtcg                                              20

<210> SEQ ID NO 1360
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1360
tatagcgcag tacggtccat                                              20

<210> SEQ ID NO 1361
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1361
atctaggcgt tcaggtgctt                                              20

<210> SEQ ID NO 1362
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1362
```
tttgcggcga tagcgtcctt                                              20

<210> SEQ ID NO 1363
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1363
ctctgggcga tagtctagtt                                              20

<210> SEQ ID NO 1364
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1364
cagtctgcga tacgctagtt                                              20

<210> SEQ ID NO 1365
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1365
cctctaggtg tacggagctt                                              20

<210> SEQ ID NO 1366
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1366
ctttagcgga tcggcgactt                                              20

<210> SEQ ID NO 1367
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1367
tttgagcggc tagacgacct                                              20

<210> SEQ ID NO 1368
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1368
tatagccgtc tagccgactt                                              20

<210> SEQ ID NO 1369
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1369
tgccgactgt acgctatctt                                          20

<210> SEQ ID NO 1370
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1370
atgccgaccg tccgtaatgt                                          20

<210> SEQ ID NO 1371
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1371
aggtcaacac gtccgttaat                                          20

<210> SEQ ID NO 1372
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1372
gcgacggcag ttaccttaat                                          20

<210> SEQ ID NO 1373
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1373
cgcagcgcga taccgttatt                                          20

<210> SEQ ID NO 1374
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1374
gccagtccga aactttaaca                                          20

<210> SEQ ID NO 1375
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1375
tggatcacga aacccggaca                                          20
```

-continued

<210> SEQ ID NO 1376
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1376
aatcgaccgg aaccgtaagc                                               20

<210> SEQ ID NO 1377
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1377
acaggtccgt aacttggtag                                               20

<210> SEQ ID NO 1378
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1378
acagagtctt gaaccgggtc                                               20

<210> SEQ ID NO 1379
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1379
taagttgaca taacgggtgc                                               20

<210> SEQ ID NO 1380
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1380
aattatggct aagcgtcgag                                               20

<210> SEQ ID NO 1381
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1381
aatacgagct aagcggccag                                               20

<210> SEQ ID NO 1382
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1382
atgcacggct aacgcttcag                                           20

<210> SEQ ID NO 1383
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1383
atatcgtgct aaccgcgcag                                           20

<210> SEQ ID NO 1384
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1384
aatgcgtgct aagtcgctag                                           20

<210> SEQ ID NO 1385
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1385
aatgcagcgt aagtcactag                                           20

<210> SEQ ID NO 1386
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1386
acattggagt aacgtgctag                                           20

<210> SEQ ID NO 1387
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1387
cacgtagagt taatcaggag                                           20

<210> SEQ ID NO 1388
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1388
ccgtatagct taatagccag                                           20

<210> SEQ ID NO 1389

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1389
cactgtaccc tagttacgat                                              20

<210> SEQ ID NO 1390
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1390
gcgctgaccg tattcgactt                                              20

<210> SEQ ID NO 1391
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1391
agcctatacg ttccggcagt                                              20

<210> SEQ ID NO 1392
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1392
agaactacat tccgcgcaag                                              20

<210> SEQ ID NO 1393
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1393
gacctcacat tgaccataag                                              20

<210> SEQ ID NO 1394
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1394
cgctacacat tgtcaagaac                                              20

<210> SEQ ID NO 1395
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1395
```

-continued

```
tgcacatcag gtaagagcag                                              20

<210> SEQ ID NO 1396
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1396
ctagatacgt tcgcagacat                                              20

<210> SEQ ID NO 1397
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1397
tgggcagcga ttccagcaat                                              20

<210> SEQ ID NO 1398
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1398 aggaacccttt tcgcagcaat                                             20

<210> SEQ ID NO 1399
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1399
atgcccgagt tgtcgccatt                                              20

<210> SEQ ID NO 1400
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1400
gactgcgagc tatgtacctt                                              20

<210> SEQ ID NO 1401
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1401
gggctagact tcccgcatat                                              20

<210> SEQ ID NO 1402
<211> LENGTH: 20
<212> TYPE: DNA
```

```
-continued

<213> ORGANISM: Artificial Sequence
<220> FEATURE:
<223> OTHER INFORMATION: synthetic oligonucleotide

<400> SEQUENCE: 1402
cgctataacg tatccgaatc                                           20

<210> SEQ ID NO 1403
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1403
ccgttatacg aatatcgacc                                           20

<210> SEQ ID NO 1404
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1404
ctcaggtact gttacgacat                                           20

<210> SEQ ID NO 1405
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1405
cgggttacag gttatcgaat                                           20

<210> SEQ ID NO 1406
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1406
cgggatactg tcctacgatt                                           20

<210> SEQ ID NO 1407
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1407
accgatactt tcgacgatct                                           20

<210> SEQ ID NO 1408
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1408
taggagcctt tcgcactact                                           20
```

```
<210> SEQ ID NO 1409
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1409
tcgagagcag gttacatacg                                               20

<210> SEQ ID NO 1410
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1410
cgtggtacga tttacgatct                                               20

<210> SEQ ID NO 1411
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1411
gcggagtcta gttcagtatt                                               20

<210> SEQ ID NO 1412
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1412
ctcgattcgg tcacgcttgt                                               20

<210> SEQ ID NO 1413
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1413
ctcgatagac gtaagttgag                                               20

<210> SEQ ID NO 1414
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1414
tatcgtagac gctcggacgt                                               20

<210> SEQ ID NO 1415
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 1415
taattcgatg tcaggagcgt                20

<210> SEQ ID NO 1416
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1416
tttgatccgc tctcacgggt                20

<210> SEQ ID NO 1417
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1417
ttggatcagc tccgcgaagt                20

<210> SEQ ID NO 1418
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1418
actcgatagt cacggctact                20

<210> SEQ ID NO 1419
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1419
tgaccgaggt acggactact                20

<210> SEQ ID NO 1420
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1420
acgcctgcat tgcgactaat                20

<210> SEQ ID NO 1421
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1421
cagtctgaac gcagtgtaag                20

<210> SEQ ID NO 1422
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1422
gcgcaataga cacgtttaga                                              20

<210> SEQ ID NO 1423
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1423
gagctacgac cagtcattag                                              20

<210> SEQ ID NO 1424
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1424
gggaccgcca aagctatcaa                                              20

<210> SEQ ID NO 1425
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1425
gccgcgctga gaacataata                                              20

<210> SEQ ID NO 1426
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1426
gcgcagctcc aatactaata                                              20

<210> SEQ ID NO 1427
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1427
gcggacggaa catactatta                                              20

<210> SEQ ID NO 1428
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 1428
actggacgac taggctatat                                              20

<210> SEQ ID NO 1429
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1429
gagggacgca tcgctttaat                                              20

<210> SEQ ID NO 1430
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1430
cggaggcgca ttgtcctaat                                              20

<210> SEQ ID NO 1431
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1431
gtgtgacgca cctcgatttc                                              20

<210> SEQ ID NO 1432
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1432
gtttgacgcc tgccgatctt                                              20

<210> SEQ ID NO 1433
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1433
ttctgacgac gagcgtactg                                              20

<210> SEQ ID NO 1434
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1434
ttctactgac gagcttgcgg                                              20

<210> SEQ ID NO 1435
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1435
attgagcgac tgaccgccat                                              20

<210> SEQ ID NO 1436
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1436
tggttacgac gatccgccat                                              20

<210> SEQ ID NO 1437
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1437
tggactgtac gtcacgccat                                              20

<210> SEQ ID NO 1438
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1438
tgatctggac gtagctctgt                                              20

<210> SEQ ID NO 1439
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1439
catataggag cagtacgccg                                              20

<210> SEQ ID NO 1440
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1440
ttcttaggac ggagcgccat                                              20

<210> SEQ ID NO 1441
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1441
```
attccgggac gtgacgacat                                           20

<210> SEQ ID NO 1442
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1442
actatgagac gagatcgacg                                           20

<210> SEQ ID NO 1443
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1443
cctcagagac tagacgacag                                           20

<210> SEQ ID NO 1444
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1444
cagtcgagat ttgcacgaat                                           20

<210> SEQ ID NO 1445
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1445
taggctagac gtgtgccaat                                           20

<210> SEQ ID NO 1446
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1446
catctaggtc caggcgtcat                                           20

<210> SEQ ID NO 1447
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1447
aaggttagct catcgggact                                           20

<210> SEQ ID NO 1448
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1448
gcattgcgat tcagacgcct                                               20

<210> SEQ ID NO 1449
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1449
gatcattgca tccgacgagt                                               20

<210> SEQ ID NO 1450
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1450
cgtatatgcg tagactgcgt                                               20

<210> SEQ ID NO 1451
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1451
acttgaggcg tagacctgct                                               20

<210> SEQ ID NO 1452
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1452
tcctagaccg tatatcggct                                               20

<210> SEQ ID NO 1453
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1453
ctctgcgcga gaaacaggaa                                               20

<210> SEQ ID NO 1454
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1454
attcgagcgg tagccacgat                                               20
```

<210> SEQ ID NO 1455
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1455
tataacgccg tggcacctgt                                              20

<210> SEQ ID NO 1456
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1456
atcatcgtcg tcagcctggt                                              20

<210> SEQ ID NO 1457
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1457
tattctgccg tcagccgtgt                                              20

<210> SEQ ID NO 1458
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1458
tatggctagg tatgacgctt                                              20

<210> SEQ ID NO 1459
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1459
tcgaggtacg ttgacgcatt                                              20

<210> SEQ ID NO 1460
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1460
cgcaggcgtc gattagtctt                                              20

<210> SEQ ID NO 1461
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1461
cgagagcgtt tcatattggt                                                     20

<210> SEQ ID NO 1462
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1462
ccgacgggct tcgattgttt                                                     20

<210> SEQ ID NO 1463
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1463
catacgggcc tagtctggtt                                                     20

<210> SEQ ID NO 1464
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1464
attagcggcc tcaggttcgt                                                     20

<210> SEQ ID NO 1465
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1465
attgaccgac caggttcgtc                                                     20

<210> SEQ ID NO 1466
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1466
tccacacgca aagggtcgaa                                                     20

<210> SEQ ID NO 1467
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1467
tcgtatagca aacgggcgaa                                                     20

<210> SEQ ID NO 1468

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1468
tgctctacca aagccgtaaa                                               20

<210> SEQ ID NO 1469
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1469
tagctcagcg aaggcttacc                                               20

<210> SEQ ID NO 1470
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1470
aacgcaagag tcgggtacat                                               20

<210> SEQ ID NO 1471
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1471
tatccgcgag cacgggttat                                               20

<210> SEQ ID NO 1472
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1472
acacgatgag aagggcctac                                               20

<210> SEQ ID NO 1473
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1473
cgcacgatac acgtacttta                                               20

<210> SEQ ID NO 1474
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1474
```
tcagaccgaa cacgacgtta    20

<210> SEQ ID NO 1475
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1475
tagccctgac tcggatcgtt    20

<210> SEQ ID NO 1476
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1476
tactcttgcg tcgagcggtt    20

<210> SEQ ID NO 1477
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1477
atcgtcagcg tagagaccct    20

<210> SEQ ID NO 1478
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1478
tctgtacggc taggtcgctt    20

<210> SEQ ID NO 1479
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1479
tagtgcgctc gatcctcgtt    20

<210> SEQ ID NO 1480
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1480
cggatgacct gatcgtcgtt    20

<210> SEQ ID NO 1481
<211> LENGTH: 20
<212> TYPE: DNA

```
-continued

<213> ORGANISM: Artificial Sequence
<220> FEATURE:
<223> OTHER INFORMATION: synthetic oligonucleotide

<400> SEQUENCE: 1481
ccagagagct gacgaattac                                               20

<210> SEQ ID NO 1482
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1482
actaagagcg acgtaattgc                                               20

<210> SEQ ID NO 1483
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1483
cattaagacg actcgaacgc                                               20

<210> SEQ ID NO 1484
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1484
catacttacg aagctgtacc                                               20

<210> SEQ ID NO 1485
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1485
ccgtgctact aatgtaagtc                                               20

<210> SEQ ID NO 1486
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1486
caccgtcact aagtagattc                                               20

<210> SEQ ID NO 1487
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1487
acacggatct aaggcacttc                                               20
```

<210> SEQ ID NO 1488
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1488
acacgaatcg aagttctcac                                      20

<210> SEQ ID NO 1489
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1489
acacagttgt acgaatctcc                                      20

<210> SEQ ID NO 1490
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1490
acatgcgtag aaggccgtac                                      20

<210> SEQ ID NO 1491
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1491
cagcatgtag aacgacggac                                      20

<210> SEQ ID NO 1492
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1492
cttagaatag aacgggtgac                                      20

<210> SEQ ID NO 1493
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1493
atagtgatcg aacccgtgcc                                      20

<210> SEQ ID NO 1494
<211> LENGTH: 20
<212> TYPE: DNA
<213> ORGANISM: Artificial Sequence
<220> FEATURE:

-continued

<223> OTHER INFORMATION: synthetic oligonucleotide

<400> SEQUENCE: 1494
tcatgcgtct aacgggctag                                               20

<210> SEQ ID NO 1495
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1495
ggcgtgatat tacgtgactt                                               20

<210> SEQ ID NO 1496
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1496
gctggatgag tacgtctatt                                               20

<210> SEQ ID NO 1497
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1497
gcgcgatgtt tctaatagct                                               20

<210> SEQ ID NO 1498
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1498
gagggacgtt tcgacattct                                               20

<210> SEQ ID NO 1499
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1499
gagggcaccg tttacatcct                                               20

<210> SEQ ID NO 1500
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1500
agcgcggagt gactacttct                                               20

```
<210> SEQ ID NO 1501
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1501
cgagcgtatg taggatcttt                                            20

<210> SEQ ID NO 1502
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1502
agagcgtcat tacgacctat                                            20

<210> SEQ ID NO 1503
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1503
aggcacgcac gactcttatt                                            20

<210> SEQ ID NO 1504
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1504
aatcggcgct cacgcttagt                                            20

<210> SEQ ID NO 1505
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1505
aagcctcgct gagtatgttt                                            20

<210> SEQ ID NO 1506
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1506
aaacgtagct gactagcctt                                            20

<210> SEQ ID NO 1507
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 1507
ccacgtagtc taactgctag                                              20

<210> SEQ ID NO 1508
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1508
cccaggagta aatcgctaga                                              20

<210> SEQ ID NO 1509
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1509
ccggtatgct aatatcgtag                                              20

<210> SEQ ID NO 1510
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1510
ccgactatta aatgcgagga                                              20

<210> SEQ ID NO 1511
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1511
aagtctatat cagtagcggg                                              20

<210> SEQ ID NO 1512
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1512
catacgatca cagttaggtc                                              20

<210> SEQ ID NO 1513
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1513
caacagatac cataggcgtc                                              20

<210> SEQ ID NO 1514
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1514
gcgcctatac aataacgtca                                              20

<210> SEQ ID NO 1515
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1515
cccgtcgtga aatacagtaa                                              20

<210> SEQ ID NO 1516
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1516
cgcctgatga aagacgtaca                                              20

<210> SEQ ID NO 1517
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1517
gcccatgtaa caagcggaca                                              20

<210> SEQ ID NO 1518
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1518
tgtcatctga aacacgacca                                              20

<210> SEQ ID NO 1519
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1519
cctgtcagta aaccgagaga                                              20

<210> SEQ ID NO 1520
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1520
```

```
cccgttcgtt aatacgtgat                                          20
```

<210> SEQ ID NO 1521
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1521

```
cgggcttatg atatacgagt                                          20
```

<210> SEQ ID NO 1522
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1522

```
cctagttcga gattgcgagt                                          20
```

<210> SEQ ID NO 1523
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1523

```
tattgctcag gatcgcggat                                          20
```

<210> SEQ ID NO 1524
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1524

```
cactgtgtag cagccggtat                                          20
```

<210> SEQ ID NO 1525
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1525

```
tcacgcgatg cagtcggtat                                          20
```

<210> SEQ ID NO 1526
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1526

```
tcaggtgagt cattggctct                                          20
```

<210> SEQ ID NO 1527
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1527
tcgtcgaaga cagggcaata                                                 20

<210> SEQ ID NO 1528
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1528
ctcgccgata actcaagata                                                 20

<210> SEQ ID NO 1529
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1529
gcgtcgcata cacataatac                                                 20

<210> SEQ ID NO 1530
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1530
ccgatagacg aacgcatgac                                                 20

<210> SEQ ID NO 1531
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1531
ccttgaatag aagcgcagac                                                 20

<210> SEQ ID NO 1532
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1532
gctcatacga tagaaccgac                                                 20

<210> SEQ ID NO 1533
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1533
ggtcgctcga tagataccct                                                 20
```

```
<210> SEQ ID NO 1534
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1534
catgagtcgt gagtacgctt                                                   20

<210> SEQ ID NO 1535
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1535
gacggctggt catataccttt                                                  20

<210> SEQ ID NO 1536
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1536
aggcgctgcg tatagtattt                                                   20

<210> SEQ ID NO 1537
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1537
ggcgagcgcg tatattcttt                                                   20

<210> SEQ ID NO 1538
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1538
gctcggcgat tatacgttgt                                                   20

<210> SEQ ID NO 1539
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1539
gcccgttctc tacagtatat                                                   20

<210> SEQ ID NO 1540
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 1540
agcctcgcgt ttacactgtt                                              20

<210> SEQ ID NO 1541
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1541
tcagcagcgt taagcctacg                                              20

<210> SEQ ID NO 1542
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1542
accagcgcgt taagtctagg                                              20

<210> SEQ ID NO 1543
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1543
cactacgctt taagtatcgg                                              20

<210> SEQ ID NO 1544
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1544
cccgatgttt aacgtatagg                                              20

<210> SEQ ID NO 1545
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1545
taggtagaac gatatgcgac                                              20

<210> SEQ ID NO 1546
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1546
gagctgaact aatagcgagc                                              20

<210> SEQ ID NO 1547
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1547
gactcataca cagtaggcgc                                               20

<210> SEQ ID NO 1548
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1548
agagcttaac cacgagcagc                                               20

<210> SEQ ID NO 1549
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1549
cagacgtaac cagtgatgcc                                               20

<210> SEQ ID NO 1550
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1550
caggcttact acatatagcg                                               20

<210> SEQ ID NO 1551
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1551
catgctcact aatctgacag                                               20

<210> SEQ ID NO 1552
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1552
cgtgtggaat catattgacg                                               20

<210> SEQ ID NO 1553
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1553
```
cactgtgagt aatgatgacg 20

<210> SEQ ID NO 1554
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1554
tctgtgaagc tgatgtaacg 20

<210> SEQ ID NO 1555
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1555
gcgcttacca tagatatacg 20

<210> SEQ ID NO 1556
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1556
gcgttacaca gatcataagc 20

<210> SEQ ID NO 1557
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1557
gtgcgacaca tgacatcaac 20

<210> SEQ ID NO 1558
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1558
gtgcgccatc aagacacaga 20

<210> SEQ ID NO 1559
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1559
gccgcagatg caacacgata 20

<210> SEQ ID NO 1560
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 1560
gcgctacatc aactgacata                                              20

<210> SEQ ID NO 1561
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1561
cggcctaaga tccaacatga                                              20

<210> SEQ ID NO 1562
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1562
cgcgcataga tcatcagaag                                              20

<210> SEQ ID NO 1563
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1563
gcctcagaca tcataatagc                                              20

<210> SEQ ID NO 1564
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1564
actagataca catgcgtgcc                                              20

<210> SEQ ID NO 1565
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1565
tcctagtaca cagcgagtgc                                              20

<210> SEQ ID NO 1566
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1566
gcgagatata cagtgatgtc                                              20
```

<210> SEQ ID NO 1567
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1567
gcataagaca cactgctgta                                              20

<210> SEQ ID NO 1568
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1568
gctaaccatc aagcatcgta                                              20

<210> SEQ ID NO 1569
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1569
cgtccacaca tgcaatagta                                              20

<210> SEQ ID NO 1570
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1570
tgactcgtct gcatctggct                                              20

<210> SEQ ID NO 1571
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1571
attggtcacc tagcactcgg                                              20

<210> SEQ ID NO 1572
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1572
cagtaggttc catagtccgt                                              20

<210> SEQ ID NO 1573
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 1573
cagatactat taagtgccgg 20

<210> SEQ ID NO 1574
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1574
caatagttac gcaggttcgg 20

<210> SEQ ID NO 1575
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1575
aaatgtgtac gaagctaccc 20

<210> SEQ ID NO 1576
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1576
atacttgcgg aagctacggc 20

<210> SEQ ID NO 1577
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1577
gagtcttcac cagttgaccg 20

<210> SEQ ID NO 1578
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1578
cgaggtgtac cgattacgct 20

<210> SEQ ID NO 1579
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1579
cgcggtaatc tgatctaacg 20

```
<210> SEQ ID NO 1580
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1580
cccgctaatc ttgtagaatc                                                   20

<210> SEQ ID NO 1581
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1581
ccgggtaatg aatgataacc                                                   20

<210> SEQ ID NO 1582
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1582
cccggtagtc tcatattact                                                   20

<210> SEQ ID NO 1583
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1583
cccgctagtc aataatcgta                                                   20

<210> SEQ ID NO 1584
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1584
ccaagtagta ccaactgtga                                                   20

<210> SEQ ID NO 1585
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1585
cccggtacta caatacgaga                                                   20

<210> SEQ ID NO 1586
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 1586
gccgtagcga caatctaaga                                           20

<210> SEQ ID NO 1587
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1587
ccggtagctg aacagattta                                           20

<210> SEQ ID NO 1588
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1588
ccggcggatg aagaattata                                           20

<210> SEQ ID NO 1589
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1589
ccggtagcat aagactatac                                           20

<210> SEQ ID NO 1590
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1590
cgcggtatta ggacatatag                                           20

<210> SEQ ID NO 1591
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1591
cgccacactt ggttaaatac                                           20

<210> SEQ ID NO 1592
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1592
caggcgactt aacctcaaag                                           20

<210> SEQ ID NO 1593
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1593
ccggcgattt aagtaacaag                                              20

<210> SEQ ID NO 1594
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1594
cccgtagtgt agattacctt                                              20

<210> SEQ ID NO 1595
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1595
cccggagtct actatactat                                              20

<210> SEQ ID NO 1596
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1596
cctgcacgtc aagaagacta                                              20

<210> SEQ ID NO 1597
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1597
gtcgcgcatc aagaacacga                                              20

<210> SEQ ID NO 1598
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1598
tgcgccgtac caagaaacga                                              20

<210> SEQ ID NO 1599
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1599
```

-continued catgcggtgt aacgagaaat        20

<210> SEQ ID NO 1600
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1600
aaatgcgagt tacgggactt        20

<210> SEQ ID NO 1601
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1601
ctatgcgagt tcgggtaatt        20

<210> SEQ ID NO 1602
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1602
cagctagagt tggcgtaatt        20

<210> SEQ ID NO 1603
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1603
ctacatagac gatagggacg        20

<210> SEQ ID NO 1604
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1604
actacgctac ggagaggact        20

<210> SEQ ID NO 1605
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1605
ctaggcgtag ggattctatt        20

<210> SEQ ID NO 1606
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1606
gagcctactg gatctcgtgt                                              20

<210> SEQ ID NO 1607
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1607
aacggagcgt gatctatgtt                                              20

<210> SEQ ID NO 1608
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1608
cggcgcgtat gatctattat                                              20

<210> SEQ ID NO 1609
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1609
gcgtcagtga gactattgat                                              20

<210> SEQ ID NO 1610
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1610
gcgccactga tactagattg                                              20

<210> SEQ ID NO 1611
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1611
cagccggtta gatatgattg                                              20

<210> SEQ ID NO 1612
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1612
gcacgagttg catatttgtg                                              20
```

<210> SEQ ID NO 1613
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1613
cggagctact gatgtctatt                                               20

<210> SEQ ID NO 1614
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1614
tcgagcgatt gagtcatagt                                               20

<210> SEQ ID NO 1615
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1615
ttcgacgcga gactctagtg                                               20

<210> SEQ ID NO 1616
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1616
tcaggcgcag aactgtagac                                               20

<210> SEQ ID NO 1617
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1617
tctaaggcga cagactggtc                                               20

<210> SEQ ID NO 1618
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1618
tatagatcga cagacggtgc                                               20

<210> SEQ ID NO 1619
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 1619
attgtcacct cagagccgtg                                               20

<210> SEQ ID NO 1620
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1620
tatgatcctc tcgacaggcg                                               20

<210> SEQ ID NO 1621
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1621
gtccgaacta tcaacacgta                                               20

<210> SEQ ID NO 1622
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1622
accgaggcga tcatttcgtg                                               20

<210> SEQ ID NO 1623
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1623
gcggcggata tgctataaat                                               20

<210> SEQ ID NO 1624
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1624
cgggcgcata tcatcttaat                                               20

<210> SEQ ID NO 1625
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1625
cgcgacgatg tatgctaaat                                               20

<210> SEQ ID NO 1626
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1626
cggatcggat gtcacttcct                                              20

<210> SEQ ID NO 1627
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1627
ctcagccgag tatattgact                                              20

<210> SEQ ID NO 1628
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1628
cagcctcagt tatatgcact                                              20

<210> SEQ ID NO 1629
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1629
acagcggagc ttatgccact                                              20

<210> SEQ ID NO 1630
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1630
tagtggcagt tagtcatgct                                              20

<210> SEQ ID NO 1631
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1631
tcattggagc tggcgacact                                              20

<210> SEQ ID NO 1632
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1632
```

```
tctatgacgc tggcgcactt                                                    20

<210> SEQ ID NO 1633
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1633
gctacgtcag tgcagttcat                                                    20

<210> SEQ ID NO 1634
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1634
catacgacag gagacactgc                                                    20

<210> SEQ ID NO 1635
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1635
tgtcgagctg cgagatcact                                                    20

<210> SEQ ID NO 1636
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1636
agtgagactg tgtgacatct                                                    20

<210> SEQ ID NO 1637
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1637
gagacgacag ctaatccatc                                                    20

<210> SEQ ID NO 1638
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1638
gggacgacat caatagccac                                                    20

<210> SEQ ID NO 1639
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 1639
gacggaacag gatctgcaac                                                    20

<210> SEQ ID NO 1640
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1640
gagcagacag actcgatcac                                                    20

<210> SEQ ID NO 1641
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1641
cgactagcat gacatttcag                                                    20

<210> SEQ ID NO 1642
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1642
agagctacag tcagtcacag                                                    20

<210> SEQ ID NO 1643
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1643
taactagcga gctgacagag                                                    20

<210> SEQ ID NO 1644
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1644
gactgacctg catgttcacg                                                    20

<210> SEQ ID NO 1645
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1645
atacgaccgt caggcacatg                                                    20
```

<210> SEQ ID NO 1646
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1646
cagacgacta tcgcataatg                                           20

<210> SEQ ID NO 1647
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1647
gcactcacta cagatagatc                                           20

<210> SEQ ID NO 1648
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1648
atgccgacta gctctcagat                                           20

<210> SEQ ID NO 1649
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1649
aagccgacat gcacgttcag                                           20

<210> SEQ ID NO 1650
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1650
agctcgatca cagcgtattc                                           20

<210> SEQ ID NO 1651
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1651
acacggatca catcgtagtc                                           20

<210> SEQ ID NO 1652
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 1652
catatactat cacgcagacg                                               20

<210> SEQ ID NO 1653
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1653
agcactcttc acagatgacg                                               20

<210> SEQ ID NO 1654
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1654
atcagccagt cacatggacg                                               20

<210> SEQ ID NO 1655
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1655
agatagcacg tcactacacg                                               20

<210> SEQ ID NO 1656
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1656
agacctcagc ttcagtaacg                                               20

<210> SEQ ID NO 1657
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1657
agcggacatt tactgaacag                                               20

<210> SEQ ID NO 1658
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1658
gcgtgacagt ttgttcaatg                                               20

```
<210> SEQ ID NO 1659
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1659
atgcgacagg tacgtcacag                                               20

<210> SEQ ID NO 1660
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1660
ttcgtacaga gtcaggaacg                                               20

<210> SEQ ID NO 1661
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1661
ctctatattg gatggagcgt                                               20

<210> SEQ ID NO 1662
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1662
cttcatatag tgagaggcgt                                               20

<210> SEQ ID NO 1663
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1663
tctatattac gagagtgcgg                                               20

<210> SEQ ID NO 1664
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1664
tctattatga gagcgtcgtg                                               20

<210> SEQ ID NO 1665
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 1665
cataatatac catgtgcgcc                                                    20

<210> SEQ ID NO 1666
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1666
tcacatatag caggtgcgag                                                    20

<210> SEQ ID NO 1667
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1667
tcagtattag catgtgccgg                                                    20

<210> SEQ ID NO 1668
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1668
tcagtcgtag cagttcgatg                                                    20

<210> SEQ ID NO 1669
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1669
tctcgtcgat catggtcgtg                                                    20

<210> SEQ ID NO 1670
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1670
ctcagccgat gcagtgtaat                                                    20

<210> SEQ ID NO 1671
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1671
actcgtagag cgtgagccat                                                    20

<210> SEQ ID NO 1672
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1672
acctagatag ctgtagccat                                              20

<210> SEQ ID NO 1673
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1673
caacgagtag gatatgctct                                              20

<210> SEQ ID NO 1674
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1674
actttcgtag gatgagtgct                                              20

<210> SEQ ID NO 1675
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1675
tcgctagtag tagagtgcat                                              20

<210> SEQ ID NO 1676
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1676
atctgagtac gatggctgat                                              20

<210> SEQ ID NO 1677
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1677
ctactgatga ggagcttgat                                              20

<210> SEQ ID NO 1678
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1678
```

-continued tcataggtcg tgacatggat   20

<210> SEQ ID NO 1679
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1679
taagatgtgt gaactgcgtc   20

<210> SEQ ID NO 1680
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1680
tcctgtctga gatcgcgtgt   20

<210> SEQ ID NO 1681
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1681
tatcctctag cactgcgtgg   20

<210> SEQ ID NO 1682
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1682
actaccgtat catgggtgtg   20

<210> SEQ ID NO 1683
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1683
ccatacctat catgtagtcg   20

<210> SEQ ID NO 1684
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1684
catggactag cagtagatcg   20

<210> SEQ ID NO 1685
<211> LENGTH: 20
<212> TYPE: DNA
<213> ORGANISM: Artificial Sequence -continued

```
<220> FEATURE:
<223> OTHER INFORMATION: synthetic oligonucleotide

<400> SEQUENCE: 1685
acgactctag catgtctacg                                               20

<210> SEQ ID NO 1686
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1686
agactattag cagcactacg                                               20

<210> SEQ ID NO 1687
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1687
agacgtgtac cattgcatcg                                               20

<210> SEQ ID NO 1688
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1688
acactcgtac cattgatgcg                                               20

<210> SEQ ID NO 1689
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1689
gactatctca cacgagtgcg                                               20

<210> SEQ ID NO 1690
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1690
gactatgtat taagcgtgcg                                               20

<210> SEQ ID NO 1691
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1691
cggatattct tcacaggtgt                                               20
```

<210> SEQ ID NO 1692
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1692
gcatcagttt aatgagtgcg                                                   20

<210> SEQ ID NO 1693
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1693
gtatcgtaaa catgcgtgga                                                   20

<210> SEQ ID NO 1694
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1694
atatcgcatg aagccgacgc                                                   20

<210> SEQ ID NO 1695
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1695
acatgcgagg aatcgtcagc                                                   20

<210> SEQ ID NO 1696
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1696
tcacgccaga cagttgtagc                                                   20

<210> SEQ ID NO 1697
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1697
cacactcagt caagatgtac                                                   20

<210> SEQ ID NO 1698
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1698
acactctagg aatggcgagc                                               20

<210> SEQ ID NO 1699
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1699
ccgcatgaga aagtcgcaca                                               20

<210> SEQ ID NO 1700
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1700
catagcgatg gacagtctag                                               20

<210> SEQ ID NO 1701
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1701
actgtcgatg gacgtgctct                                               20

<210> SEQ ID NO 1702
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1702
actatggcta gacaggctcg                                               20

<210> SEQ ID NO 1703
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1703
cgtatagctc gatatggccg                                               20

<210> SEQ ID NO 1704
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1704
cagatagctt gacatagtcg                                               20

<210> SEQ ID NO 1705

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1705
gagatagctc gaatcagtcc                                              20

<210> SEQ ID NO 1706
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1706
cgatgatcta gcattagtcg                                              20

<210> SEQ ID NO 1707
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1707
cgatgagcag cactcgtaag                                              20

<210> SEQ ID NO 1708
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1708
gagtaagcag tcctgtcaag                                              20

<210> SEQ ID NO 1709
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1709
agcctagcgt atctgtcatt                                              20

<210> SEQ ID NO 1710
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1710
ccttagacgc tactgtattg                                              20

<210> SEQ ID NO 1711
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1711
```

```
ctgcgaacga actatatcga                                              20

<210> SEQ ID NO 1712
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1712
gagatgacgt gacatattcg                                              20

<210> SEQ ID NO 1713
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1713
ctccggtcga tggatgaatt                                              20

<210> SEQ ID NO 1714
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1714
cccggaacgt caatgagaac                                              20

<210> SEQ ID NO 1715
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1715
ggcgacacgt acagaatcac                                              20

<210> SEQ ID NO 1716
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1716
tagtacacca gacgtgatcc                                              20

<210> SEQ ID NO 1717
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1717
tggataccgc tgcacgtact                                              20

<210> SEQ ID NO 1718
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 1718
aggaacgtgc tcgcatatct                                               20

<210> SEQ ID NO 1719
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1719
atttgagccg agcccgaact                                               20

<210> SEQ ID NO 1720
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1720
tggtacttac gaccgcgact                                               20

<210> SEQ ID NO 1721
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1721
atagctgaac caggcgtacc                                               20

<210> SEQ ID NO 1722
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1722
tcctagtaac gagccgtaag                                               20

<210> SEQ ID NO 1723
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1723
ctgtcataac gacggctaag                                               20

<210> SEQ ID NO 1724
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1724
tatggtgaat cgacccgaag                                               20
```

```
<210> SEQ ID NO 1725
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1725
tggtaggcca aacccgacaa                                              20

<210> SEQ ID NO 1726
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1726
agataggacg ttccacgaat                                              20

<210> SEQ ID NO 1727
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1727
ttatgggacc tagcccgact                                              20

<210> SEQ ID NO 1728
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1728
atttcggagg acccgcgtat                                              20

<210> SEQ ID NO 1729
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1729
tattaggctg gacgacccgt                                              20

<210> SEQ ID NO 1730
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1730
aggcagtcac tacgctcgat                                              20

<210> SEQ ID NO 1731
<211> LENGTH: 20
<212> TYPE: DNA
<213> ORGANISM: Artificial Sequence
<220> FEATURE:
```

```
<223> OTHER INFORMATION: synthetic oligonucleotide

<400> SEQUENCE: 1731
atacggtgag catacctgg                                           20

<210> SEQ ID NO 1732
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1732
tggaggcgac aacccaatca                                          20

<210> SEQ ID NO 1733
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1733
aggacacgac gaatctcgac                                          20

<210> SEQ ID NO 1734
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1734
tgaccataca cgaactggac                                          20

<210> SEQ ID NO 1735
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1735
agagaccgca ctaacgtgtc                                          20

<210> SEQ ID NO 1736
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1736
agacactgta ataacgcggc                                          20

<210> SEQ ID NO 1737
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1737
tgacacagtt aatacagggc                                          20
```

<210> SEQ ID NO 1738
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1738
tgccacataa cagaccggga                                           20

<210> SEQ ID NO 1739
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1739
cacatcgttt aacactggag                                           20

<210> SEQ ID NO 1740
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1740
gcacgagtta gaacacggac                                           20

<210> SEQ ID NO 1741
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1741
ggccgtcata aacgcgaaca                                           20

<210> SEQ ID NO 1742
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1742
cggcgcgata aagtctaaca                                           20

<210> SEQ ID NO 1743
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1743
gctcgataag aacccagcta                                           20

<210> SEQ ID NO 1744
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 1744
tggcgcgacg aacacgaata                                              20

<210> SEQ ID NO 1745
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1745
gtgggagcca aacctcacaa                                              20

<210> SEQ ID NO 1746
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1746
ccggcagcga aactatctaa                                              20

<210> SEQ ID NO 1747
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1747
caggaggcgc aataccctta                                              20

<210> SEQ ID NO 1748
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1748
aagatcgcgc aacgaccgta                                              20

<210> SEQ ID NO 1749
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1749
gagagcaccg aacactcgta                                              20

<210> SEQ ID NO 1750
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1750
gcatacatag caacctcgta                                              20

<210> SEQ ID NO 1751
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1751
gcatacatga gaacttcgac                                              20

<210> SEQ ID NO 1752
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1752
cagatacggg aacactgtac                                              20

<210> SEQ ID NO 1753
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1753
agacatcccg aatctggtac                                              20

<210> SEQ ID NO 1754
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1754
tgcaccacga aagcggtaca                                              20

<210> SEQ ID NO 1755
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1755
gcacgcacgt aacttgattc                                              20

<210> SEQ ID NO 1756
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1756
gacagcacgt aattgaccgc                                              20

<210> SEQ ID NO 1757
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1757
```

| | |
|---|---|
| gagatcagct caacgacgac | 20 |

<210> SEQ ID NO 1758
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1758

| | |
|---|---|
| agatcgcgtc aactgaagcc | 20 |

<210> SEQ ID NO 1759
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1759

| | |
|---|---|
| tgcagagaat aactgtgacc | 20 |

<210> SEQ ID NO 1760
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1760

| | |
|---|---|
| aaatgctagt caagcggacc | 20 |

<210> SEQ ID NO 1761
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1761

| | |
|---|---|
| aacgatgact aacatggtcc | 20 |

<210> SEQ ID NO 1762
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1762

| | |
|---|---|
| acagactact aacggtgatc | 20 |

<210> SEQ ID NO 1763
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1763

| | |
|---|---|
| gcagatcact caagcgtaac | 20 |

<210> SEQ ID NO 1764
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1764
gatccataac catgcggtac                                              20

<210> SEQ ID NO 1765
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1765
ccgtcaataa acccggtgaa                                              20

<210> SEQ ID NO 1766
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1766
tgggacacat aacccggaac                                              20

<210> SEQ ID NO 1767
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1767
atagcgccgt aaccgtctag                                              20

<210> SEQ ID NO 1768
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1768
aatcgcgtgt aaccgcttag                                              20

<210> SEQ ID NO 1769
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1769
agatcactgt aaccgccgag                                              20

<210> SEQ ID NO 1770
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1770
tatatgctgt aaggcccgcg                                              20
```

```
<210> SEQ ID NO 1771
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1771
attgcattgt aaccgcgccg                                                    20

<210> SEQ ID NO 1772
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1772
aaggatgcgt aacccgcttc                                                    20

<210> SEQ ID NO 1773
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1773
gagcagtcgc tagtaccctt                                                    20

<210> SEQ ID NO 1774
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1774
aattctccgt cgagggcgtt                                                    20

<210> SEQ ID NO 1775
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1775
atgtcgccga taggcccttt                                                    20

<210> SEQ ID NO 1776
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1776
actcgcgtat gaggtcgttt                                                    20

<210> SEQ ID NO 1777
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 1777
gacggcgttc gactcttgtt 20

<210> SEQ ID NO 1778
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1778
cacttgattc gacggtgtgt 20

<210> SEQ ID NO 1779
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1779
cactgtctac gatgggttct 20

<210> SEQ ID NO 1780
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1780
acgcatctac gactgtgggt 20

<210> SEQ ID NO 1781
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1781
aacctcgtat ggacggtgtt 20

<210> SEQ ID NO 1782
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1782
atatctctag gcacgggttg 20

<210> SEQ ID NO 1783
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1783
atattcgtac cacggagccg 20

<210> SEQ ID NO 1784

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1784
tatgcgctaa cagggttcgc                                              20

<210> SEQ ID NO 1785
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1785
atacgacttc aagggacgcc                                              20

<210> SEQ ID NO 1786
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1786
aatactctct gacgggaggt                                              20

<210> SEQ ID NO 1787
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1787
aactatgttg aacgtgggtc                                              20

<210> SEQ ID NO 1788
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1788
aatactgtgg tacacgcggt                                              20

<210> SEQ ID NO 1789
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1789
taaggcgtcg tcactacggt                                              20

<210> SEQ ID NO 1790
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1790
```
tgtgcgatcc tactgaccgt                                              20

<210> SEQ ID NO 1791
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1791
ctattcgtca ggaccggact                                              20

<210> SEQ ID NO 1792
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1792
atcttcgtga ggatacggtt                                              20

<210> SEQ ID NO 1793
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1793
atatcgtgtg gcagacgttt                                              20

<210> SEQ ID NO 1794
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1794
tcaacccgtg ggactgagtt                                              20

<210> SEQ ID NO 1795
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1795
cgagcccgtt gctataattt                                              20

<210> SEQ ID NO 1796
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1796
catgtacgag tagtaggact                                              20

<210> SEQ ID NO 1797
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 1797
atgacaagag ggtcgaactc                                              20

<210> SEQ ID NO 1798
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1798
atactaggtc ggtgaagact                                              20

<210> SEQ ID NO 1799
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1799
ttacgaggtc ggtacactct                                              20

<210> SEQ ID NO 1800
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1800
agggaccagt cacagtcatc                                              20

<210> SEQ ID NO 1801
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1801
ttggacctct cagcgatgct                                              20

<210> SEQ ID NO 1802
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1802
gagctgctat cactgtgcat                                              20

<210> SEQ ID NO 1803
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1803
cgcacgctct gcattgatat                                              20
```

```
<210> SEQ ID NO 1804
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1804
gagactcgct gcattgccat                                              20

<210> SEQ ID NO 1805
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1805
gagacatcgt gcaacatcac                                              20

<210> SEQ ID NO 1806
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1806
cgcatgacgc aatatggata                                              20

<210> SEQ ID NO 1807
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1807
cctgatacgc aatgacgata                                              20

<210> SEQ ID NO 1808
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1808
gcagccacgc aatgctaata                                              20

<210> SEQ ID NO 1809
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1809
acagctccgc aatgtgagta                                              20

<210> SEQ ID NO 1810
<211> LENGTH: 20
<212> TYPE: DNA
<213> ORGANISM: Artificial Sequence
<220> FEATURE:
```

-continued

<223> OTHER INFORMATION: synthetic oligonucleotide

<400> SEQUENCE: 1810
acactcatgc aagcgatgta                                               20

<210> SEQ ID NO 1811
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1811
ctatcaaggc aagcgatcta                                               20

<210> SEQ ID NO 1812
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1812
catgacgtag cactgagatg                                               20

<210> SEQ ID NO 1813
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1813
catgacgatg cagtatgatg                                               20

<210> SEQ ID NO 1814
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1814
tcgctagatc gagctgcatg                                               20

<210> SEQ ID NO 1815
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1815
tactatggag catgtctgag                                               20

<210> SEQ ID NO 1816
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1816
tacatcacga cattctgtgc                                               20

<210> SEQ ID NO 1817
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1817
ttactgacga catcgcgtgc                                              20

<210> SEQ ID NO 1818
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1818
atgctgacgc agatccgatg                                              20

<210> SEQ ID NO 1819
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1819
atatgcgctg aacgctctgc                                              20

<210> SEQ ID NO 1820
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1820
tatgcaacga cacgcgctga                                              20

<210> SEQ ID NO 1821
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1821
catataccgc aatggagcta                                              20

<210> SEQ ID NO 1822
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1822
tagataccga tacagtgctc                                              20

<210> SEQ ID NO 1823
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 1823 ataggcgc aagcagcgta                                              20

<210> SEQ ID NO 1824
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1824
catacagcgt cagacagatc                                            20

<210> SEQ ID NO 1825
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1825
actatcgcgg agatgctgat                                            20

<210> SEQ ID NO 1826
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1826
caaagtgcgc tgaagctatc                                            20

<210> SEQ ID NO 1827
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1827
cctaactaga gatatgcgtc                                            20

<210> SEQ ID NO 1828
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1828
agtatagaca gatatgcgcc                                            20

<210> SEQ ID NO 1829
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1829
aggtcagaca gcattcgctc                                            20

<210> SEQ ID NO 1830
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1830
attcgataca gagcacgcgc                                                    20

<210> SEQ ID NO 1831
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1831
ggtcagaaca cacactgcga                                                    20

<210> SEQ ID NO 1832
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1832
ggacagtaca cagagcatcc                                                    20

<210> SEQ ID NO 1833
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1833
tagacgtaca catgagccgc                                                    20

<210> SEQ ID NO 1834
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1834
tagactcaga catagctgcc                                                    20

<210> SEQ ID NO 1835
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1835
ttaggcgaga cagactgctc                                                    20

<210> SEQ ID NO 1836
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1836
```

| ttaggctatg caccgctctg | 20 |

<210> SEQ ID NO 1837
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1837

| actacggatt catgcgctct | 20 |

<210> SEQ ID NO 1838
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1838

| aacgatgtag catggctctg | 20 |

<210> SEQ ID NO 1839
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1839

| tatacgatga cagagtgtgc | 20 |

<210> SEQ ID NO 1840
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1840

| ttagcagcga cacgatgtgc | 20 |

<210> SEQ ID NO 1841
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1841

| actacgactg actcgatgtg | 20 |

<210> SEQ ID NO 1842
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1842

| cctagatcgc aatagatgga | 20 |

<210> SEQ ID NO 1843
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1843
cctaagtcta cagagatgtc                                              20

<210> SEQ ID NO 1844
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1844
ccgtattctg aagcatagtc                                              20

<210> SEQ ID NO 1845
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1845
cagtaatcag aagctcgcac                                              20

<210> SEQ ID NO 1846
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1846
cgatatgcag aatagcgcac                                              20

<210> SEQ ID NO 1847
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1847
cacgtatctg aatgacgatc                                              20

<210> SEQ ID NO 1848
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1848
acagctactg aagttgatgc                                              20

<210> SEQ ID NO 1849
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1849
tacaggactg aagatagcgc                                              20
```

<210> SEQ ID NO 1850
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1850
tacgagtcta cagcaggcag                                              20

<210> SEQ ID NO 1851
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1851
cgggcgacat aagcagatac                                              20

<210> SEQ ID NO 1852
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1852
ggacgatcat ccagcactag                                              20

<210> SEQ ID NO 1853
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1853
gcgctctcaa gcaatataga                                              20

<210> SEQ ID NO 1854
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1854
ccggagtcat cagatattag                                              20

<210> SEQ ID NO 1855
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1855
gccgtgacat catatttgag                                              20

<210> SEQ ID NO 1856
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 1856
agacggactc gcattcactg                                               20

<210> SEQ ID NO 1857
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1857
atacggtctc gcagatcgct                                               20

<210> SEQ ID NO 1858
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1858
ttacggtcac gactcgcatg                                               20

<210> SEQ ID NO 1859
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1859
acactgtcat aatcgcgcag                                               20

<210> SEQ ID NO 1860
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1860
ataccgtcag catacgtgcg                                               20

<210> SEQ ID NO 1861
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1861
actggtacgt gatctgatgt                                               20

<210> SEQ ID NO 1862
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1862
ccacggtcga gactgatatg                                               20

<210> SEQ ID NO 1863
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1863
acacggtatg aactgactgc                                               20

<210> SEQ ID NO 1864
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1864
ccgtcgtata aatgagagca                                               20

<210> SEQ ID NO 1865
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1865
cgttgatagc aagcgagata                                               20

<210> SEQ ID NO 1866
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1866
ccgtagtagc aatcagtcta                                               20

<210> SEQ ID NO 1867
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1867
ctctagtatg caggatgttg                                               20

<210> SEQ ID NO 1868
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1868
cccgagtatc tgagctgatt                                               20

<210> SEQ ID NO 1869
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1869
```
cgatctaatg acatagcagc                                          20

<210> SEQ ID NO 1870
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1870
ctacagatac ggacatagtc                                          20

<210> SEQ ID NO 1871
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1871
tatcaggatc gagactatgg                                          20

<210> SEQ ID NO 1872
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1872
agctggcatc gactctatct                                          20

<210> SEQ ID NO 1873
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1873
gatcggcatc tagcttgact                                          20

<210> SEQ ID NO 1874
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1874
agcatggact cagcgtgact                                          20

<210> SEQ ID NO 1875
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1875
agatggcact cacgtcactg                                          20

<210> SEQ ID NO 1876
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 1876
atgcacgact tctgagcaat                                                    20

<210> SEQ ID NO 1877
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1877
atccgataca tccgctgaag                                                    20

<210> SEQ ID NO 1878
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1878
taccagtaca ttgcctgaag                                                    20

<210> SEQ ID NO 1879
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1879
ttcaccgagc taggagactg                                                    20

<210> SEQ ID NO 1880
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1880
taacatgact ggacagagcg                                                    20

<210> SEQ ID NO 1881
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1881
atacacgctc ggaagactgc                                                    20

<210> SEQ ID NO 1882
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1882
tccgcagcat tggacatacg                                                    20
```

<210> SEQ ID NO 1883
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1883
atagagactt ggacatagcg                                                    20

<210> SEQ ID NO 1884
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1884
tatgacgctc gatacgcagg                                                    20

<210> SEQ ID NO 1885
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1885
tatacgacgc tagacgcagg                                                    20

<210> SEQ ID NO 1886
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1886
caagagacgc taattgcggc                                                    20

<210> SEQ ID NO 1887
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1887
ataggcacgg aatcttgcgc                                                    20

<210> SEQ ID NO 1888
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1888
atattgtcgg aacgctgcgc                                                    20

<210> SEQ ID NO 1889
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 1889
acagcatcgg aacgcatagc                                               20

<210> SEQ ID NO 1890
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1890
gtcacatcac aggaatctac                                               20

<210> SEQ ID NO 1891
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1891
cgtgactcag gagctactat                                               20

<210> SEQ ID NO 1892
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1892
gtacagtcag aacgagccac                                               20

<210> SEQ ID NO 1893
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1893
atagagactg aagcccacgc                                               20

<210> SEQ ID NO 1894
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1894
aatacgactg aaggatcggc                                               20

<210> SEQ ID NO 1895
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1895
aataccgcgc aagcgtcgta                                               20

<210> SEQ ID NO 1896
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1896
atacttgtgc aacgtgcgcc                                              20

<210> SEQ ID NO 1897
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1897
gactctacga tacgtcgctg                                              20

<210> SEQ ID NO 1898
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1898
tactgcgaga tacgtgtctg                                              20

<210> SEQ ID NO 1899
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1899
actgcatagt cactgtggtg                                              20

<210> SEQ ID NO 1900
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1900
tcacgctaga tcacgattgg                                              20

<210> SEQ ID NO 1901
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1901
gatactacga catctagggc                                              20

<210> SEQ ID NO 1902
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 1902
acactcacga catataggtc                                            20

<210> SEQ ID NO 1903
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1903
aatactccgc aatcggcgta                                            20

<210> SEQ ID NO 1904
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1904
atattgtctc acgcggcgct                                            20

<210> SEQ ID NO 1905
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1905
tatgtcaccg tcatcgtgct                                            20

<210> SEQ ID NO 1906
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1906
gtatcaccgc ttcacaggat                                            20

<210> SEQ ID NO 1907
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1907
gccatcgcgc ttgacagtat                                            20

<210> SEQ ID NO 1908
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1908
tgtatcccga ttgacgcgct                                            20

<210> SEQ ID NO 1909
<211> LENGTH: 20
```

```
<212> TYPE: DNA
<213> ORGANISM: Artificial Sequence
<220> FEATURE:
<223> OTHER INFORMATION: synthetic oligonucleotide

<400> SEQUENCE: 1909
tgctagtcga tgccaccgat                                                 20

<210> SEQ ID NO 1910
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1910
agctagacta tcgcccaatg                                                 20

<210> SEQ ID NO 1911
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1911
tgttacacca caacgcgaga                                                 20

<210> SEQ ID NO 1912
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1912
gctcacacgc aagaatcgga                                                 20

<210> SEQ ID NO 1913
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1913
catacttcga cagatccgag                                                 20

<210> SEQ ID NO 1914
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1914
tacagctcag cacttgacgg                                                 20

<210> SEQ ID NO 1915
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1915
```

-continued atacgctcag cagattccgg　　　　　　　　　　　　　　　　　　　　20

<210> SEQ ID NO 1916
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1916
catacgtcac gactagctgg　　　　　　　　　　　　　　　　　　　　20

<210> SEQ ID NO 1917
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1917
atcctgacac gactgagagg　　　　　　　　　　　　　　　　　　　　20

<210> SEQ ID NO 1918
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1918
tactcggcac gacggatatg　　　　　　　　　　　　　　　　　　　　20

<210> SEQ ID NO 1919
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1919
attctatcac gagcggcacg　　　　　　　　　　　　　　　　　　　　20

<210> SEQ ID NO 1920
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1920
tgtctagcac gtcctgcaat　　　　　　　　　　　　　　　　　　　　20

<210> SEQ ID NO 1921
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1921
tagtctacac gatccgcagg　　　　　　　　　　　　　　　　　　　　20

<210> SEQ ID NO 1922
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 1922
ttaggtacac tacacgtcgc                                              20

<210> SEQ ID NO 1923
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1923
tgacgtacac gagctacacg                                              20

<210> SEQ ID NO 1924
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1924
taggattctc gaccagcacg                                              20

<210> SEQ ID NO 1925
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1925
tggagataga cagaccaccc                                              20

<210> SEQ ID NO 1926
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1926
gatagataag cacgcagccc                                              20

<210> SEQ ID NO 1927
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1927
tgagtacata gacagcaccc                                              20

<210> SEQ ID NO 1928
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1928
tagatacatc gacgcgcttc                                              20
```

<210> SEQ ID NO 1929
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1929
taatagcgtc gaagcctcgc                                              20

<210> SEQ ID NO 1930
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1930
ttaaacaacg aatgcgccgc                                              20

<210> SEQ ID NO 1931
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1931
aatactcagg aactcgcagc                                              20

<210> SEQ ID NO 1932
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1932
cattactagg aatcacacgc                                              20

<210> SEQ ID NO 1933
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1933
tcggtcgaag aacgcacaga                                              20

<210> SEQ ID NO 1934
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1934
tctaggagac gatacgcacg                                              20

<210> SEQ ID NO 1935
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 1935
taggacgagt cactgcatcg                                          20

<210> SEQ ID NO 1936
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1936
cgagacgagt gctctacatg                                          20

<210> SEQ ID NO 1937
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1937
gaagcagagt tcagcacatc                                          20

<210> SEQ ID NO 1938
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1938
ggaacgaacg tgcatgaatc                                          20

<210> SEQ ID NO 1939
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1939
cgtatcgaca ggatgcacag                                          20

<210> SEQ ID NO 1940
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1940
gcactctaca gatgatacag                                          20

<210> SEQ ID NO 1941
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1941
gactgctaca gatgcgacag                                          20

<210> SEQ ID NO 1942
```

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1942
gcgacttaca gcactatcag                                          20

<210> SEQ ID NO 1943
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1943
ggtgaccatc gcacatctag                                          20

<210> SEQ ID NO 1944
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1944
gactagatag gcatcattcg                                          20

<210> SEQ ID NO 1945
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1945
acgatgaggt aatctatgcg                                          20

<210> SEQ ID NO 1946
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1946
cagcgagtga catttatgcg                                          20

<210> SEQ ID NO 1947
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1947
cgtgagttaa gctatatgcg                                          20

<210> SEQ ID NO 1948
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1948
```

```
tagcacctga gacacttgcg                                              20

<210> SEQ ID NO 1949
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1949
acagcactgg aactatgcgc                                              20

<210> SEQ ID NO 1950
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1950
cagagactgt gacattatcg                                              20

<210> SEQ ID NO 1951
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1951
cattgagtgg aatagactgc                                              20

<210> SEQ ID NO 1952
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1952
aatcgactgg aagtgtctgc                                              20

<210> SEQ ID NO 1953
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1953
cgacgactgc tcacgattat                                              20

<210> SEQ ID NO 1954
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1954
cagcgactgc aactattgta                                              20

<210> SEQ ID NO 1955
<211> LENGTH: 20
<212> TYPE: DNA
```

```
<213> ORGANISM: Artificial Sequence
<220> FEATURE:
<223> OTHER INFORMATION: synthetic oligonucleotide

<400> SEQUENCE: 1955
tagcgactga gatcatacgg                                             20

<210> SEQ ID NO 1956
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1956
gcgagcataa catagcgtga                                             20

<210> SEQ ID NO 1957
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1957
tgcgacatga gacacacgac                                             20

<210> SEQ ID NO 1958
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1958
ccacgactgg aatacgatgc                                             20

<210> SEQ ID NO 1959
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1959
accatagttg cagatacctg                                             20

<210> SEQ ID NO 1960
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1960
gcaccgagta gatagcatcg                                             20

<210> SEQ ID NO 1961
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1961
agacctagac cacatgaggc                                             20
```

```
<210> SEQ ID NO 1962
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1962
caacctagag gatatgcgag                                                20

<210> SEQ ID NO 1963
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1963
acctagcaga gagatgtcag                                                20

<210> SEQ ID NO 1964
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1964
aactagcgtg aaggatgatc                                                20

<210> SEQ ID NO 1965
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1965
actcatagtg aaggagatgc                                                20

<210> SEQ ID NO 1966
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1966
actatgagtg aaggctatgc                                                20

<210> SEQ ID NO 1967
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1967
catgagagtg aagcagtatc                                                20

<210> SEQ ID NO 1968
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 1968
actgctagta gagatgcttg                        20

<210> SEQ ID NO 1969
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1969
cgacgtatga tagactcttg                        20

<210> SEQ ID NO 1970
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1970
ccgcgtatag aattgtctga                        20

<210> SEQ ID NO 1971
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1971
tcccgaatga caaggcacga                        20

<210> SEQ ID NO 1972
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1972
cctagagtgc aagagaccta                        20

<210> SEQ ID NO 1973
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1973
ccaggagtat aatgtgacag                        20

<210> SEQ ID NO 1974
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1974
ccgagcttag aagatgatac                        20

```
<210> SEQ ID NO 1975
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1975
accggcgtat gatatagagt                                           20

<210> SEQ ID NO 1976
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1976
cgcgccatat catacaagta                                           20

<210> SEQ ID NO 1977
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1977
aggcgcgtgc tatatctctt                                           20

<210> SEQ ID NO 1978
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1978
cacggtatgt gcatttgagt                                           20

<210> SEQ ID NO 1979
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1979
catacgttga aactacggca                                           20

<210> SEQ ID NO 1980
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1980
gatagtatga aactcgggca                                           20

<210> SEQ ID NO 1981
<211> LENGTH: 20
<212> TYPE: DNA
<213> ORGANISM: Artificial Sequence
<220> FEATURE:
<223> OTHER INFORMATION: synthetic oligonucleotide
```

-continued

<400> SEQUENCE: 1981
cataggtgta aattcgcgga                                              20

<210> SEQ ID NO 1982
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1982
tacaggcggt aattgccgtc                                              20

<210> SEQ ID NO 1983
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1983
ttcacgcgga taaccgagtc                                              20

<210> SEQ ID NO 1984
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1984
ctatcgagag tagtacggat                                              20

<210> SEQ ID NO 1985
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1985
caagtatgag gagtatccgt                                              20

<210> SEQ ID NO 1986
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1986
tcagttcgag taatatcggg                                              20

<210> SEQ ID NO 1987
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1987
gactatcgac tacttcggat                                              20

<210> SEQ ID NO 1988
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 1988
cattacgggc aacttcgtta                                              20

<210> SEQ ID NO 1989
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1989
aggctcagcg tacctagtat                                              20

<210> SEQ ID NO 1990
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1990
gtgacccggc tacctatgtt                                              20

<210> SEQ ID NO 1991
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1991
gatgaccgcc aacggaacta                                              20

<210> SEQ ID NO 1992
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1992
ggatagtgcc taccgactct                                              20

<210> SEQ ID NO 1993
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1993
gatacgagcc tacggactat                                              20

<210> SEQ ID NO 1994
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1994
```

-continued tgtacctgac tcctcgaatt                                              20

<210> SEQ ID NO 1995
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1995
tctatccgag tagcgggaat                                              20

<210> SEQ ID NO 1996
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1996
tactttcgag gagccggaat                                              20

<210> SEQ ID NO 1997
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1997
atctcccgag gtgacggaat                                              20

<210> SEQ ID NO 1998
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1998
atatctcgcg tcggacaggt                                              20

<210> SEQ ID NO 1999
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1999
taaaccagcg tccgaaggtc                                              20

<210> SEQ ID NO 2000
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2000
agagcccgag tcacgtaact                                              20

<210> SEQ ID NO 2001
<211> LENGTH: 20
<212> TYPE: DNA
<213> ORGANISM: Artificial Sequence

```
<220> FEATURE:
<223> OTHER INFORMATION: synthetic oligonucleotide

<400> SEQUENCE: 2001
atgtacccag tcacacttag                                                 20

<210> SEQ ID NO 2002
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2002
cgcgcagagg ttagataaat                                                 20

<210> SEQ ID NO 2003
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2003
atcaggtctg gaagattacg                                                 20

<210> SEQ ID NO 2004
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2004
cgcgttatgc aatacggtta                                                 20

<210> SEQ ID NO 2005
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2005
catgagctag aagtcaggac                                                 20

<210> SEQ ID NO 2006
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2006
agctcgatac tgactgagat                                                 20

<210> SEQ ID NO 2007
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2007
cccgtcggtc gatgctattt                                                 20
```

```
<210> SEQ ID NO 2008
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2008
ccacgcatcc aagattagga                                              20

<210> SEQ ID NO 2009
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2009
atcatgtcac cagagtgccg                                              20

<210> SEQ ID NO 2010
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2010
acagttatcc taagtcgcag                                              20

<210> SEQ ID NO 2011
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2011
atgaagtgct aggaatccgc                                              20

<210> SEQ ID NO 2012
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2012
aagtacgtcg aagcagcagc                                              20

<210> SEQ ID NO 2013
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2013
gctctacgac aataagctca                                              20

<210> SEQ ID NO 2014
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 2014
tagacacggt acgaatgccc                                               20

<210> SEQ ID NO 2015
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2015
ctccggcatt agaacataac                                               20

<210> SEQ ID NO 2016
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2016
cgcatggtat ctaagactag                                               20

<210> SEQ ID NO 2017
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2017
taaccgctcg tcatgtgtct                                               20

<210> SEQ ID NO 2018
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2018
cactcgacgc aaggtttata                                               20

<210> SEQ ID NO 2019
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2019
tcttggcgac gctatgacgt                                               20

<210> SEQ ID NO 2020
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2020
agacacctat ttgtaacggg                                               20

<210> SEQ ID NO 2021

```
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2021
agagacgacc taagccagtc                                              20

<210> SEQ ID NO 2022
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2022
atcacgcgcc taagtgctag                                              20

<210> SEQ ID NO 2023
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2023
atagcgagcc taatgccgag                                              20

<210> SEQ ID NO 2024
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2024
acggattcag cagtcctcat                                              20

<210> SEQ ID NO 2025
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2025
tatctgcggc tcactgtcgt                                              20

<210> SEQ ID NO 2026
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2026
gcagctacta tacgatcatg                                              20

<210> SEQ ID NO 2027
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2027
```
cgagtgacta gatacgctat                    20

<210> SEQ ID NO 2028
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2028
tttcatggac cgacgggcat                    20

<210> SEQ ID NO 2029
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2029
agatgcgtga gcactacttg                    20

<210> SEQ ID NO 2030
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2030
cagtcggtag aactatgtac                    20

<210> SEQ ID NO 2031
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2031
atacgacctt acgcgctgg                     19

<210> SEQ ID NO 2032
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2032
tctacagcga tctatacacg                    20

<210> SEQ ID NO 2033
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2033
catagatgga aatcggcgca                    20

<210> SEQ ID NO 2034
<211> LENGTH: 20
<212> TYPE: DNA

```
<213> ORGANISM: Artificial Sequence
<220> FEATURE:
<223> OTHER INFORMATION: synthetic oligonucleotide

<400> SEQUENCE: 2034
agatgtagaa cacccgtcac                                               20

<210> SEQ ID NO 2035
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2035
aacgatccgg tacatttagg                                               20

<210> SEQ ID NO 2036
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2036
tgccagctaa gacacagtac                                               20

<210> SEQ ID NO 2037
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2037
cctctgagta aatacggaga                                               20

<210> SEQ ID NO 2038
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2038
gtccgcattg catgatgagt                                               20

<210> SEQ ID NO 2039
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2039
acacctgagg aagcgatagc                                               20

<210> SEQ ID NO 2040
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2040
gcagcgcaga aagtctcaca                                               20
```

<210> SEQ ID NO 2041
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2041
gcaacgggtt gtaattctg                                              19

<210> SEQ ID NO 2042
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2042
tcatgtcgca tcagctattg                                             20

<210> SEQ ID NO 2043
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2043
atgactgctg ccagagtgct                                             20

<210> SEQ ID NO 2044
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2044
taatggacat gacgcgacag                                             20

<210> SEQ ID NO 2045
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2045
ccgtagtatg aatgacatgc                                             20

<210> SEQ ID NO 2046
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2046
agtatcgcag tctacgagat                                             20

<210> SEQ ID NO 2047
<211> LENGTH: 19
<212> TYPE: DNA
<213> ORGANISM: Artificial Sequence
<220> FEATURE:

```
<223> OTHER INFORMATION: synthetic oligonucleotide

<400> SEQUENCE: 2047
gcacggatga ttagcactg                                              19

<210> SEQ ID NO 2048
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2048
gcgcgactta tgtccatgct                                             20

<210> SEQ ID NO 2049
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2049
aaacccgatg tcgcctaatt                                             20

<210> SEQ ID NO 2050
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2050
cgacctcgct tcagttaatt                                             20
```